(12) United States Patent
Kanno et al.

(10) Patent No.: US 8,685,981 B2
(45) Date of Patent: Apr. 1, 2014

(54) CYCLIC COMPOUND HAVING HETERO ATOM

(75) Inventors: Osamu Kanno, Kanagawa (JP); Katsuyoshi Nakajima, Tokyo (JP); Kazumasa Aoki, Tokyo (JP); Ryoichi Tanaka, Tokyo (JP); Shimpei Hirano, Chiba (JP); Kiyoshi Oizumi, Kanagawa (JP); Daigo Asano, Tokyo (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 13/182,777

(22) Filed: Jul. 14, 2011

(65) Prior Publication Data

US 2011/0269746 A1    Nov. 3, 2011

Related U.S. Application Data

(63) Continuation of application No. PCT/JP2010/050221, filed on Jan. 12, 2010.

(30) Foreign Application Priority Data

Jan. 19, 2009   (JP) .................. 2009-008635

(51) Int. Cl.
A61K 31/497   (2006.01)

(52) U.S. Cl.
USPC ............. 514/253.04; 514/217.07; 514/235.2; 514/253.05; 514/300; 514/310; 514/218; 540/575; 540/597; 544/121; 544/128; 544/362; 544/363; 546/122; 546/143

(58) Field of Classification Search
USPC ............... 514/217.07, 235.2, 253.04, 253.05, 514/300, 310; 540/575, 597; 544/121, 128, 544/362, 363; 546/122, 143
See application file for complete search history.

(56) References Cited

U.S. PATENT DOCUMENTS

2006/0030584 A1*   2/2006   Hanson et al. ............... 514/300

FOREIGN PATENT DOCUMENTS

| EP | 1 389 468 A1 | 2/2004 |
|---|---|---|
| EP | 1 481 977 A1 | 12/2004 |
| WO | 02/094321 A1 | 11/2002 |
| WO | 02/100405 A1 | 12/2002 |
| WO | 03/074525 A1 | 9/2003 |
| WO | 2006/017672 A2 | 2/2006 |
| WO | 2007/020046 A1 | 2/2007 |

OTHER PUBLICATIONS

Silverman, The Organic Chemistry of Drug Design and Drug Action, Second Edition, Copyright 2004.*
International Search Report mailed Feb. 16, 2010, issued in corresponding International Application No. PCT/JP2010/050221, filed Jan. 12, 2010, 5 pages.
Kitaura, H., "Analysis of TNF-α-Induced Osteoclastogenesis In Vivo," The Bone 21(6):75-78, Nov. 2007 (English translation, 7 pages).
Tanaka, Y., "Paradigm Shift of Treatments of Osteoporosis and Rheumatoid Arthritis," The Bone 22(3):153-157, Jun. 2008 (English translation, 8 pages).

* cited by examiner

*Primary Examiner* — Brandon Fetterolf
*Assistant Examiner* — Jean Cornet
(74) *Attorney, Agent, or Firm* — Christensen O'Connor Johnson Kindness PLLC

(57) ABSTRACT

Compounds exhibiting an osteogenesis-promoting action having the general formula (I) or a pharmacologically acceptable salt thereof:

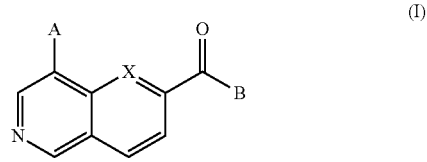

wherein A is selected from among a 3- to 10-membered heterocyclyl group, B is selected from among an amino group, and X is selected from N and CH.

12 Claims, No Drawings

CYCLIC COMPOUND HAVING HETERO ATOM

TECHNICAL FIELD

The present invention relates to a heteroatom-containing cyclic compound or a pharmacologically acceptable salt thereof useful for the prevention or treatment of diseases associated with bone metabolism, for example, osteoporosis, osteitis fibrosa (hyperparathyroidism), osteomalacia, and Paget's disease.

BACKGROUND ART

Generally in normal bone metabolism, bone resorption by osteoclasts and osteogenesis by osteoblasts are balanced, whereby homeostasis is maintained. It is presumed that diseases associated with bone metabolism develop when the balance between bone resorption and osteogenesis is disrupted. Such diseases include osteoporosis, osteitis fibrosa (hyperparathyroidism), osteomalacia, Paget's disease, and the like. Particularly, osteoporosis often develops in postmenopausal women and elderly people with accompanying symptoms of pain such as low back pain, bone fracture, etc. Particularly, bone fracture in elderly people is serious because it leads to generalized weakness and dementia. For such diseases associated with bone metabolism, hormone replacement therapies with estrogen and therapeutic agents such as bisphosphonates and calcitonins, both of which inhibit the activity of osteoclasts, have been employed.

However, although many of these therapeutic agents are reported to have a bone resorption-inhibiting action, etc., none of them has yet been clearly shown to have an osteogenesis-promoting action. Particularly, impaired osteogenic ability due to reduced bone turnover is reported to be the main cause of senile osteoporosis (Non Patent Literature 1), and thus a medicinal agent promoting osteogenesis is considered to be effective.

In view of the above, development of a highly clinically effective, orally administrable osteogenesis promoter is demanded.

Recently, benzothiepine derivatives having an alkaline phosphatase-inducing activity (Patent Literatures 1 and 2), N-quinolinylanthranilic acid derivatives (Patent Literature 3), triazolopyridazine derivatives (Patent Literature 4), and thienopyridine derivatives (Patent Literature 5) are reported to be useful for promotion of osteogenesis and for the treatment of diseases associated with bone metabolism. However, their clinical utility remains unknown.

CITATION LIST

Patent Literature

Patent Literature 1: U.S. Pat. No. 6,346,521
Patent Literature 2: U.S. Pat. No. 6,632,807
Patent Literature 3: Japanese Patent Laid-Open No. 9-188665
Patent Literature 4: U.S. Pat. No. 7,173,033
Patent Literature 5: Japanese Patent Laid-Open No. 2007-131617

Non Patent Literature

Non Patent Literature 1: New Eng. J. Med. 314, 1976 (1986)

SUMMARY OF INVENTION

Technical Problem

In order to reduce pain and risk of bone fracture in diseases associated with bone metabolism such as osteoporosis, bone mass and bone strength need to be increased. As means of increasing bone mass and bone strength, it is considered to be important to promote osteogenesis by osteoblasts as this is considered to be definitely effective. Accordingly, an object of the present invention is to provide a highly safe, orally administrable novel low molecular weight compound exhibiting an osteogenesis-promoting action.

Solution to Problem

The present inventors conducted an intensive study in order to develop a therapeutic medication with an osteogenesis-promoting action. As a result, they have found an excellent compound of the present invention that exhibits a potent osteogenesis-promoting action and is potentially capable of serving as a therapeutic medication for the prevention or treatment of diseases associated with bone metabolism, thereby completing the present invention.

That is, the present invention is as follows.

(1) A compound having the general formula (I) or a pharmacologically acceptable salt thereof:

[Chemical formula 1]

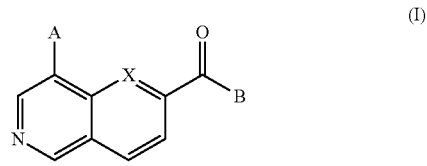

wherein each substituent is defined as follows: A represents a 3- to 10-membered heterocyclyl group optionally substituted with group(s) selected from A1, and the 3- to 10-membered heterocyclyl group represents a group selected from the group consisting of an azetidinyl group, a pyrrolidinyl group, a piperidinyl group, a morpholinyl group, a 1,4-dioxanyl group, a piperazinyl group, an azepanyl group, a 1,4-diazepanyl group, a pyrrolyl group, a thiazoyl group, a pyridyl group, a tetrahydropyridyl group, a tetrahydropyranyl group, a tetrahydrofuranyl group, a tetrahydroisoquinolinyl group, and a decahydroisoquinolinyl group, A1:
a hydroxyl group, a halogen atom, a cyano group, a nitro group, a carbamoyl group, a di C1-C6 alkylcarbamoyl group, a C1-C6 alkyl group optionally substituted with group(s) selected from A2,
a C1-C6 alkoxy group optionally substituted with group(s) selected from A2,
a C1-C6 alkylcarbonyl group optionally substituted with group(s) selected from A2,
a C1-C6 alkoxycarbonyl group optionally substituted with group(s) selected from A2,
a C3-C6 cycloalkyl group optionally substituted with group(s) selected from A2,
a C6-C10 aryl group optionally substituted with group(s) selected from A2,
a C6-C10 aryloxy group optionally substituted with group(s) selected from A2, a C6-C10 arylcarbonyl group optionally substituted with group(s) selected from A2,
a 3- to 10-membered heterocyclyl group optionally substituted with group(s) selected from A2,
a 3- to 10-membered heterocyclyloxy group optionally substituted with group(s) selected from A2, and
a 3- to 10-membered heterocyclylcarbonyl group optionally substituted with group(s) selected from A2.

A2:
a hydroxyl group, a halogen atom, a cyano group, a nitro group, a carbamoyl group, a di C1-C6 alkylcarbamoyl group, a di C1-C6 alkylaminosulfonyl group,
a carbamoyloxy group optionally substituted with group(s) selected from A3,
a C1-C6 alkylamino group optionally substituted with group(s) selected from A3,
a C1-C6 alkyl group optionally substituted with group(s) selected from A3,
a C1-C6 cycloalkyl group optionally substituted with group(s) selected from A3,
a C1-C6 alkoxy group optionally substituted with group(s) selected from A3,
a C3-C6 cycloalkoxy group optionally substituted with group(s) selected from A3,
a C1-C6 alkylcarbonyl group optionally substituted with group(s) selected from A3,
a halogeno C1-C6 alkyl group,
a halogeno C1-C6 alkoxy group,
a 3- to 10-membered heterocyclyl group optionally substituted with group(s) selected from A3,
a 3- to 10-membered heterocyclyloxy group optionally substituted with group(s) selected from A3,
a 3- to 10-membered heterocyclylcarbonyl group optionally substituted with group(s) selected from A3, and
a 3- to 10-membered heterocyclylsulfonyl group optionally substituted with group(s) selected from A3.

A3:
a halogen atom, an amino group, a hydroxyl group, a cyano group, a C1-C6 alkyl group, a C1-C6 alkoxy group, a halogeno C1-C6 alkoxy group, a C1-C6 alkoxycarbonylamino group, a 3- to 10-membered heterocyclyl group, a 3- to 10-membered heterocyclyloxy group, a carbamoyl group, a di C1-C6 alkylcarbamoyl group, and a C1-C6 alkylsulfonyl group.

B represents any one substituent selected from the following group of substituents:
an amino group optionally substituted with group(s) selected from B1 and
a 3- to 10-membered heterocyclyl group optionally substituted with group(s) selected from B1.

B1:
a hydroxyl group, an amino group, a C1-C6 alkyl group, a C1-C6 alkoxy group, a hydroxy C1-C6 alkyl group, and
X represents —N═ or —CH═.

Further, preferred examples of the present invention are as follows:

(2) The compound or the pharmacologically acceptable salt thereof according to (1), wherein A is a piperidinyl group optionally substituted with group(s) selected from A1, a piperazinyl group optionally substituted with group(s) selected from A1, or a morpholinyl group optionally substituted with group(s) selected from A1.

(3) The compound or the pharmacologically acceptable salt thereof according to (1) or (2) wherein A1 is the following group of substituents:
a hydroxyl group, a halogen atom, a cyano group, a dimethylcarbamoyl group, a diethylcarbamoyl group, an ethylmethylcarbamoyl group,
a C1-C3 alkyl group optionally substituted with group(s) selected from A2,
a C1-C3 alkoxy group optionally substituted with group(s) selected from A2,
a C1-C3 alkylcarbonyl group optionally substituted with group(s) selected from A2,
a C1-C3 alkoxycarbonyl group optionally substituted with group(s) selected from A2,
a cyclohexyl group optionally substituted with group(s) selected from A2,
a phenyl group optionally substituted with group(s) selected from A2,
a phenoxy group optionally substituted with group(s) selected from A2,
a benzoyl group optionally substituted with group(s) selected from A2,
a 3- to 10-membered heterocyclyl group optionally substituted with group(s) selected from A2,
a 3- to 10-membered heterocyclyloxy group optionally substituted with group(s) selected from A2, and
a 3- to 10-membered heterocyclylcarbonyl group optionally substituted with group(s) selected from A2.

(4) The compound or the pharmacologically acceptable salt thereof according to any one selected from (1) to (3), wherein A2 is the following group of substituents:
a hydroxyl group, a halogen atom, a cyano group, a nitro group, a dimethylcarbamoyl group, a diethylcarbamoyl group, an ethylmethylcarbamoyl group, a dimethylaminosulfonyl group,
a carbamoyloxy group optionally substituted with group(s) selected from A3,
a C1-C3 alkylamino group optionally substituted with group(s) selected from A3,
a C1-C3 alkyl group optionally substituted with group(s) selected from A3,
a C1-C3 alkoxy group optionally substituted with group(s) selected from A3,
a cyclopropyloxy group optionally substituted with group(s) selected from A3,
a cyclohexyloxy group optionally substituted with group(s) selected from A3,
a C1-C3 alkylcarbonyl group optionally substituted with group(s) selected from A3,
a halogeno C1-C6 alkyl group,
a halogeno C1-C6 alkoxy group,
a 3- to 10-membered heterocyclyl group optionally substituted with group(s) selected from A3,
a 3- to 10-membered heterocyclyloxy group optionally substituted with group(s) selected from A3,
a 3- to 10-membered heterocyclylcarbonyl group optionally substituted with group(s) selected from A3, and
a 3- to 10-membered heterocyclylsulfonyl group optionally substituted with group(s) selected from A3.

(5) The compound or the pharmacologically acceptable salt thereof according to any one selected from (1) to (4), wherein A3 represents the following group of substituents:
a halogen atom, an amino group, a hydroxyl group, a t-butoxycarbonylamino group, a C1-C6 alkyl group, a C1-C3 alkoxy group, a halogeno C1-C3 alkoxy group, a 3- to 10-membered heterocyclyl group, a 3- to 10-membered heterocyclyloxy group, a dimethylcarbamoyl group, a diethylcarbamoyl group, an ethylmethylcarbamoyl group, and a methylsulfonyl group.

(6) The compound or the pharmacologically acceptable salt thereof according to any one selected from (1) to (5), wherein B is an amino group optionally substituted with C1-C6 alkyl group(s).

(7) The compound or the pharmacologically acceptable salt thereof according to any one selected from (1) to (5), wherein B is an amino group, a methylamino group, or an ethylamino group.

(8) The compound or the pharmacologically acceptable salt thereof according to any one selected from (1) to (7), wherein X is —N=.

(9) The compound or the pharmacologically acceptable salt thereof according to any one selected from (1) to (7), wherein the general formula (I) is the general formula (I-a):

[Chemical formula 2]

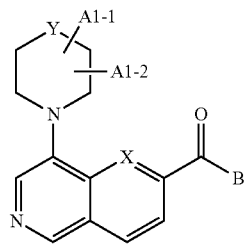

(I-a)

wherein each substituent represents the same meaning as in the general formula (I), A1-1 and A1-2 are the same or different and represent a hydrogen atom or a group selected from the group of substituents A1, and Y represents —CH—, —CH$_2$—, —NH—, —N—, or —O—.

(10) The compound or the pharmacologically acceptable salt thereof according to (9), wherein A1-2 is a hydrogen atom.

(11) The compound or the pharmacologically acceptable salt thereof according to (9) or (10), wherein A1-1 is a group selected from the following group of substituents:
a hydroxyl group, a halogen atom, a cyano group, a dimethylcarbamoyl group,
a C1-C3 alkyl group optionally substituted with group(s) selected from A2,
a C1-C3 alkoxy group optionally substituted with group(s) selected from A2,
a C1-C3 alkylcarbonyl group optionally substituted with group(s) selected from A2,
a C1-C3 alkoxycarbonyl group optionally substituted with group(s) selected from A2,
a cyclohexyl group optionally substituted with group(s) selected from A2,
a phenyl group optionally substituted with group(s) selected from A2,
a phenoxy group optionally substituted with group(s) selected from A2,
a benzoyl group optionally substituted with group(s) selected from A2,
a 3- to 10-membered heterocyclyl group optionally substituted with group(s) selected from A2,
a 3- to 10-membered heterocyclyloxy group optionally substituted with group(s) selected from A2, and
a 3- to 10-membered heterocyclylcarbonyl group optionally substituted with group(s) selected from A2.

(12) The compound or the pharmacologically acceptable salt thereof according to (9) or (10), wherein A1-1 is a group selected from the following group of substituents:
a dimethylcarbamoyl group,
a C1-C3 alkoxy group optionally substituted with group(s) selected from A2,
a C1-C3 alkoxycarbonyl group optionally substituted with group(s) selected from A2,
a phenyl group optionally substituted with group(s) selected from A2,
a phenoxy group optionally substituted with group(s) selected from A2, and
a 3- to 10-membered heterocyclyl group optionally substituted with group(s) selected from A2.

(13) The compound or the pharmacologically acceptable salt thereof according to any one selected from (9) to (12), wherein A2 is the following group of substituents:
a hydroxyl group, a halogen atom, a cyano group, a nitro group, a dimethylcarbamoyl group, a dimethylaminosulfonyl group,
a carbamoyloxy group optionally substituted with group(s) selected from A3,
a C1-C3 alkylamino group optionally substituted with group(s) selected from A3,
a C1-C3 alkyl group optionally substituted with group(s) selected from A3,
a C1-C3 alkoxy group optionally substituted with group(s) selected from A3,
a cyclopropyloxy group optionally substituted with group(s) selected from A3,
a cyclohexyloxy group optionally substituted with group(s) selected from A3,
a C1-C3 alkylcarbonyl group optionally substituted with group(s) selected from A3,
a 3- to 10-membered heterocyclyl group optionally substituted with group(s) selected from A3,
a 3- to 10-membered heterocyclyloxy group optionally substituted with group(s) selected from A3,
a 3- to 10-membered heterocyclylcarbonyl group optionally substituted with group(s) selected from A3, and
a 3- to 10-membered heterocyclylsulfonyl group optionally substituted with group(s) selected from A3.

(14) The compound or the pharmacologically acceptable salt thereof according to any one selected from (9) to (12), wherein A2 represents the following group of substituents:
a dimethylcarbamoyl group, a dimethylaminosulfonyl group,
a carbamoyloxy group optionally substituted with group(s) selected from A3,
a C1-C3 alkylamino group optionally substituted with group(s) selected from A3,
a C1-C3 alkyl group optionally substituted with group(s) selected from A3,
a C1-C3 alkoxy group optionally substituted with group(s) selected from A3,
a cyclopropyloxy group optionally substituted with group(s) selected from A3, and
a cyclohexyloxy group optionally substituted with group(s) selected from A3.

(15) The compound or the pharmacologically acceptable salt thereof according to any one selected from (9) to (14), wherein A3 is the following group of substituents:
a halogen atom, an amino group, a hydroxyl group, a t-butoxycarbonylamino group, a C1-C6 alkyl group, a C1-C3 alkoxy group, a halogeno C1-C3 alkoxy group, a 3- to 10-membered heterocyclyl group, a 3- to 10-membered heterocyclyloxy group, a dimethylcarbamoyl group, a diethylcarbamoyl group, an ethylmethylcarbamoyl group, and a methylsulfonyl group.

(16) The compound or the pharmacologically acceptable salt thereof according to any one selected from (9) to (14), wherein A3 is the following group of substituents:
a halogen atom, an amino group, a hydroxyl group, a methyl group, a methoxy group, a difluoromethoxy group, a t-butoxycarbonylamino group, a 3- to 10-membered heterocyclyl group, a 3- to 10-membered heterocyclyloxy group, a dimethylcarbamoyl group, and a methylsulfonyl group.

(17) The compound or the pharmacologically acceptable salt thereof according to any one selected from (9) to (14), wherein A3 is the following group of substituents:
a 3- to 10-membered heterocyclyl group, a 3- to 10-membered heterocyclyloxy group, a methylsulfonyl group, a methoxy group, and a difluoromethoxy group.

(18) The compound or the pharmacologically acceptable salt thereof according to any one selected from (9) to (16), wherein Y is —CH—, —CH$_2$—, —NH—, or —N—.

(19) The compound or the pharmacologically acceptable salt thereof according to (9) or (10), wherein A1-1 is a group selected from the following group of substituents:
a phenyl group, a methoxy group, a methoxymethyl group, a 2-(tetrahydro-2H-pyran-4-yloxy)ethoxy group, a 2-(cyclopropyloxy)ethoxy group, a 2-(dimethylamino)-2-oxoethoxy group, a dimethylcarbamoyl group, a 2-[methyl(methylsulfonyl)amino]ethoxy group, a 2-ethoxyethoxy group, a 2-[(3R)-tetrahydrofuran-3-yloxy]ethoxy group, a 2-[(3S)-tetrahydrofuran-3-yloxy]ethoxy group, a 2-(tetrahydrofuran-3-ylmethoxy)ethoxy group, a thiazoyl group, a 2-[(4-methoxytetrahydrofuran-3-yl)oxy]ethoxy group, and a 2-(tetrahydro-2H-pyran-4-yloxy)ethoxycarbonyl group.

(20) The compound or the pharmacologically acceptable salt thereof according to any one selected from (9) to (19), wherein B is an amino group optionally substituted with C1-C6 alkyl group(s).

(21) The compound or the pharmacologically acceptable salt thereof according to any one selected from (9) to (19), wherein B is an amino group, a methylamino group, or an ethylamino group.

(22) The compound or the pharmacologically acceptable salt thereof according to any one selected from (9) to (21), wherein X is —N=.

(23) A compound selected from the following group of compounds or a pharmacologically acceptable salt thereof:
8-piperidin-1-yl-1,6-naphthyridine-2-carboxamide,
8-morpholin-4-yl-1,6-naphthyridine-2-carboxamide,
8-(4-phenylpiperazin-1-yl)-1,6-naphthyridine-2-carboxamide,
8-(4-methoxypiperidin-1-yl)-1,6-naphthyridine-2-carboxamide,
8-[3-(methoxymethyl)piperidin-1-yl]-1,6-naphthyridine-2-carboxamide,
8-{4-[2-(tetrahydro-2H-pyran-4-yloxy)ethoxy]piperidin-1-yl}-1,6-naphthyridine-2-carboxamide,
N-ethyl-8-{4-[2-(tetrahydro-2H-pyran-4-yloxy)ethoxy]piperidin-1-yl}-1,6-naphthyridine-2-carboxamide,
8-{4-[2-(cyclopropyloxy)ethoxy]piperidin-1-yl}-1,6-naphthyridine-2-carboxamide,
8-{4-[2-(dimethylamino)-2-oxoethoxy]piperidin-1-yl}-1,6-naphthyridine-2-carboxamide,
8-[4-(dimethylcarbamoyl)piperazin-1-yl]-1,6-naphthyridine-2-carboxamide,
8-(4-{2-[methyl(methylsulfonyl)amino]ethoxy}piperidin-1-yl)-1,6-naphthyridine-2-carboxamide,
8-[4-(2-ethoxyethoxy)piperidin-1-yl]-1,6-naphthyridine-2-carboxamide,
8-(4-{2-[(3R)-tetrahydrofuran-3-yloxy]ethoxy}piperidin-1-yl)-1,6-naphthyridine-2-carboxamide,
N-ethyl-8-(4-{2-[(3R)-tetrahydrofuran-3-yloxy]ethoxy}piperidin-1-yl}-1,6-naphthyridine-2-carboxamide,
8-(4-{2-[(3S)-tetrahydrofuran-3-yloxy]ethoxy}piperidin-1-yl)-1,6-naphthyridine-2-carboxamide,
N-ethyl-8-(4-{2-[(3S)-tetrahydrofuran-3-yloxy]ethoxy}piperidin-1-yl)-1,6-naphthyridine-2-carboxamide,
8-{4-[2-(tetrahydrofuran-3-ylmethoxy)ethoxy]piperidin-1-yl}-1,6-naphthyridine-2-carboxamide,
N-ethyl-8-{4-[2-(tetrahydrofuran-3-ylmethoxy)ethoxy]piperidin-1-yl}-1,6-naphthyridine-2-carboxamide
4-piperidin-1-yl-isoquinoline-6-carboxamide,
4-(4-phenylpiperazin-1-yl)isoquinoline-6-carboxamide,
4-morpholin-4-ylisoquinoline-6-carboxamide,
4-[(3S)-3-(methoxymethyl)piperidin-1-yl]isoquinoline-6-carboxamide,
4-[(3R)-3-(methoxymethyl)piperidin-1-yl]isoquinoline-6-carboxamide,
4-[4-(1,3-thiazol-2-yl)piperazin-1-yl]isoquinoline-6-carboxamide,
4-{4-[2-(tetrahydro-2H-pyran-4-yloxy)ethoxy]piperidin-1-yl}isoquinoline-6-carboxamide,
4-{4-[2-(cyclopropyloxy)ethoxy]piperidin-1-yl}isoquinoline-6-carboxamide,
trans-8-(4-{2-[(4-methoxytetrahydrofuran-3-yl)oxy]ethoxy}piperidin-1-yl)-1,6-naphthyridine-2-carboxamide, and
2-(tetrahydro-2H-pyran-4-yloxy)ethyl 4-(2-carbamoyl-1,6-naphthyridin-8-yl)piperazine-1-carboxylate.

(24) A pharmaceutical composition comprising the compound or the pharmacologically acceptable salt thereof according to any one selected from (1) to (23) as an active ingredient.

(25) The pharmaceutical composition according to (24), wherein the pharmaceutical composition is used for promoting osteogenesis.

(26) The pharmaceutical composition according to (24), wherein the pharmaceutical composition is used for improving bone metabolism.

(27) The pharmaceutical composition according to (24), wherein the pharmaceutical composition is used for the prevention or treatment of a disease associated with bone metabolism.

(28) The pharmaceutical composition according to (27), wherein the disease associated with bone metabolism is osteoporosis.

(29) A method for improving bone metabolism, comprising administering an effective amount of the pharmaceutical composition according to (24) to a mammal.

(30) A method for preventing or treating a disease associated with bone metabolism, comprising administering an effective amount of the pharmaceutical composition according to (24) to a mammal.

(31) A method for preventing or treating osteoporosis, comprising administering an effective amount of the pharmaceutical composition according to (24) to a mammal.

Advantageous Effects of Invention

The compound of the present invention is highly safe and exhibits favorable disposition. Also, it has an excellent osteogenesis-promoting action, and thus is useful for the prevention or treatment of metabolic bone disease associated with reduced osteogenic ability relative to bone resorption ability. Examples of such metabolic bone disease include osteoporosis, osteitis fibrosa (hyperparathyroidism), osteomalacia, and further, Paget's disease, which affects systemic parameters of bone metabolism. Particularly, the compound of the present invention is useful for senile osteoporosis associated with impaired osteogenic ability. Further, application of the osteogenesis promoter of the present invention in the field of orthopedics to promotion of healing of bone fracture, a bone defect, and bone diseases such as osteoarthritis as well as in the field of dentistry to treatment of periodontal disease, stabilization of artificial tooth root, etc. is anticipated.

DESCRIPTION OF EMBODIMENTS

The present invention will be described in detail hereinbelow.

The substituents in the aforementioned general formula (I) will be explained.

A represents a 3- to 10-membered heterocyclyl group optionally substituted with group(s) selected from A1, and the 3- to 10-membered heterocyclyl group represents a group selected from the group consisting of an azetidinyl group, a pyrrolidinyl group, a piperidinyl group, a morpholinyl group, a 1,4-dioxanyl group, a piperazinyl group, an azepanyl group, a 1,4-diazepanyl group, a pyrrolyl group, a thiazoyl group, a pyridyl group, a tetrahydropyridyl group, a tetrahydropyranyl group, a tetrahydrofuranyl group, a tetrahydroisoquinolinyl group, and a decahydroisoquinolinyl group.

Preferably, A is a piperidinyl group optionally substituted with group(s) selected from A1, a piperazinyl group optionally substituted with group(s) selected from A1, or a morpholinyl group optionally substituted with group(s) selected from A1.

A1 represents the following group of substituents:
a hydroxyl group, a halogen atom, a cyano group, a nitro group, a carbamoyl group, a di C1-C6 alkylcarbamoyl group,
a C1-C6 alkyl group optionally substituted with group(s) selected from A2,
a C1-C6 alkoxy group optionally substituted with group(s) selected from A2,
a C1-C6 alkylcarbonyl group optionally substituted with group(s) selected from A2,
a C1-C6 alkoxycarbonyl group optionally substituted with group(s) selected from A2,
a C3-C6 cycloalkyl group optionally substituted with group(s) selected from A2,
a C6-C10 aryl group optionally substituted with group(s) selected from A2,
a C6-C10 aryloxy group optionally substituted with group(s) selected from A2,
a C6-C10 arylcarbonyl group optionally substituted with group(s) selected from A2,
a 3- to 10-membered heterocyclyl group optionally substituted with group(s) selected from A2,
a 3- to 10-membered heterocyclyloxy group optionally substituted with group(s) selected from A2, and
a 3- to 10-membered heterocyclylcarbonyl group optionally substituted with group(s) selected from A2.

Preferably, A1 is the following group of substituents:
a hydroxyl group, a halogen atom, a cyano group, a dimethylcarbamoyl group,
a C1-C3 alkyl group optionally substituted with group(s) selected from A2,
a C1-C3 alkoxy group optionally substituted with group(s) selected from A2,
a C1-C3 alkylcarbonyl group optionally substituted with group(s) selected from A2,
a C1-C3 alkoxycarbonyl group optionally substituted with group(s) selected from A2,
a cyclohexyl group optionally substituted with group(s) selected from A2,
a phenyl group optionally substituted with group(s) selected from A2,
a phenoxy group optionally substituted with group(s) selected from A2,
a benzoyl group optionally substituted with group(s) selected from A2,
a 3- to 10-membered heterocyclyl group optionally substituted with group(s) selected from A2,
a 3- to 10-membered heterocyclyloxy group optionally substituted with group(s) selected from A2, and
a 3- to 10-membered heterocyclylcarbonyl group optionally substituted with group(s) selected from A2.

More preferably, A1 represents the following group of substituents:
a dimethylcarbamoyl group,
a C1-C3 alkoxy group optionally substituted with group(s) selected from A2,
a C1-C3 alkoxycarbonyl group optionally substituted with group(s) selected from A2,
a phenyl group optionally substituted with group(s) selected from A2,
a phenoxy group optionally substituted with group(s) selected from A2, and
a 3- to 10-membered heterocyclyl group optionally substituted with group(s) selected from A2.

A2 represents the following group of substituents:
a hydroxyl group, a halogen atom, a cyano group, a nitro group, a carbamoyloxy group, a di C1-C6 alkylcarbamoyl group, a di C1-C6 alkylaminosulfonyl group,
a carbamoyloxy group optionally substituted with group(s) selected from A3,
a C1-C6 alkylamino group optionally substituted with group(s) selected from A3,
a C1-C6 alkyl group optionally substituted with group(s) selected from A3,
a C1-C6 cycloalkyl group optionally substituted with group(s) selected from A3,
a C1-C6 alkoxy group optionally substituted with group(s) selected from A3,
a C3-C6 cycloalkoxy group optionally substituted with group(s) selected from A3,
a C1-C6 alkylcarbonyl group optionally substituted with group(s) selected from A3,
a halogeno C1-C6 alkyl group,
a halogeno C1-C6 alkoxy group,
a 3- to 10-membered heterocyclyl group optionally substituted with group(s) selected from A3,
a 3- to 10-membered heterocyclyloxy group optionally substituted with group(s) selected from A3,
a 3- to 10-membered heterocyclylcarbonyl group optionally substituted with group(s) selected from A3, and
a 3- to 10-membered heterocyclylsulfonyl group optionally substituted with group(s) selected from A3.

Preferably, A2 is the following group of substituents:
a hydroxyl group, a halogen atom, a cyano group, a nitro group, a dimethylcarbamoyl group, a diethylcarbamoyl group, an ethylmethylcarbamoyl group, a dimethylaminosulfonyl group, a carbamoyloxy group optionally substituted with group(s) selected from A3,
a C1-C3 alkylamino group optionally substituted with group(s) selected from A3,
a C1-C3 alkyl group optionally substituted with group(s) selected from A3,
a C1-C3 alkoxy group optionally substituted with group(s) selected from A3,
a cyclopropyloxy group optionally substituted with group(s) selected from A3,
a cyclohexyloxy group optionally substituted with group(s) selected from A3,
a C1-C3 alkylcarbonyl group optionally substituted with group(s) selected from A3,
a halogeno C1-C6 alkyl group,
a halogeno C1-C6 alkoxy group,
a 3- to 10-membered heterocyclyl group optionally substituted with group(s) selected from A3,
a 3- to 10-membered heterocyclyloxy group optionally substituted with group(s) selected from A3,
a 3- to 10-membered heterocyclylcarbonyl group optionally substituted with group(s) selected from A3, and
a 3- to 10-membered heterocyclylsulfonyl group optionally substituted with group(s) selected from A3.
More preferably, A2 is the following group of substituents:
a dimethylcarbamoyl group, a dimethylaminosulfonyl group,
a carbamoyloxy group optionally substituted with group(s) selected from A3,
a C1-C3 alkylamino group optionally substituted with group(s) selected from A3,
a C1-C3 alkyl group optionally substituted with group(s) selected from A3,
a C1-C3 alkoxy group optionally substituted with group(s) selected from A3,
a cyclopropyloxy group optionally substituted with group(s) selected from A3, and
a cyclohexyloxy group optionally substituted with group(s) selected from A3.
A3 represents the following group of substituents:
a halogen atom, an amino group, a hydroxyl group, a cyano group, a C1-C6 alkyl group, a C1-C6 alkoxy group, a halogeno C1-C6 alkoxy group, a C1-C6 alkoxycarbonylamino group, a 3- to 10-membered heterocyclyl group, a 3- to 10-membered heterocyclyloxy group, a carbamoyl group, a di C1-C6 alkylcarbamoyl group, and a C1-C6 alkylsulfonyl group.
Preferably, A3 is the following group of substituents:
a halogen atom, an amino group, a hydroxyl group, a t-butoxycarbonylamino group, a C1-C6 alkyl group, a C1-C3 alkoxy group, a halogeno C1-C3 alkoxy group, a 3- to 10-membered heterocyclyl group, a 3- to 10-membered heterocyclyloxy group, a dimethylcarbamoyl group, a diethylcarbamoyl group, an ethylmethylcarbamoyl group, and a methylsulfonyl group.
More preferably, A3 is the following group of substituents:
a 3- to 10-membered heterocyclyloxy group, a methylsulfonyl group, a methyl group, and a difluoromethoxy group.
B represents the following group of substituents:
an amino group optionally substituted with group(s) selected from B1 and
a 3- to 10-membered heterocyclyl group optionally substituted with group(s) selected from B1.
Preferably, B is an amino group optionally substituted with group(s) selected from B1.
More preferably, B is an amino group, a methylamino group, or an ethylamino group.

B1 represents the following group of substituents:
a hydroxyl group, an amino group, a C1-C6 alkyl group, a C1-C6 alkoxy group, a hydroxy C1-C6 alkyl group.
Preferably, B1 is a C1-C6 alkyl group.
The substituents in the aforementioned general formula (Ia) will be explained.
In the formula, each substituent represents the same meaning as in the general formula (I).
A1-1 and A1-2 are the same or different and represent a hydrogen atom or a group selected from A1.
Preferably, A1-2 is a hydrogen atom.
Preferably, A1-1 is a group selected from the following group of substituents:
a hydroxyl group, a halogen atom, a cyano group, a dimethylcarbamoyl group,
a C1-C3 alkyl group optionally substituted with group(s) selected from A2,
a C1-C3 alkoxy group optionally substituted with group(s) selected from A2,
a C1-C3 alkylcarbonyl group optionally substituted with group(s) selected from A2,
a C1-C3 alkoxycarbonyl group optionally substituted with group(s) selected from A2,
a cyclohexyl group optionally substituted with group(s) selected from A2,
a phenyl group optionally substituted with group(s) selected from A2,
a phenoxy group optionally substituted with group(s) selected from A2,
a benzoyl group optionally substituted with group(s) selected from A2,
a 3- to 10-membered heterocyclyl group optionally substituted with group(s) selected from A2,
a 3- to 10-membered heterocyclyloxy group optionally substituted with group(s) selected from A2, and
a 3- to 10-membered heterocyclylcarbonyl group optionally substituted with group(s) selected from A2.
More preferably, A1-1 is a group selected from the following group of substituents:
a dimethylcarbamoyl group,
a C1-C3 alkoxy group optionally substituted with group(s) selected from A2,
a C1-C3 alkoxycarbonyl group optionally substituted with group(s) selected from A2,
a phenyl group optionally substituted with group(s) selected from A2,
a phenoxy group optionally substituted with group(s) selected from A2, and
a 3- to 10-membered heterocyclyl group optionally substituted with group(s) selected from A2.
Particularly and further preferably, A1-1 is a group selected from the following group of substituents:
a phenyl group, a methoxy group, a methoxymethyl group, a 2-(tetrahydro-2H-pyran-4-yloxy)ethoxy group, a 2-(cyclopropyloxy)ethoxy group, a 2-(dimethylamino)-2-oxoethoxy group, a dimethylcarbamoyl group, a 2-[methyl(methylsulfonyl)amino]ethoxy group, a 2-ethoxyethoxy group, a 2-[(3R)-tetrahydrofuran-3-yloxy]ethoxy group, a 2-[(3S)-tetrahydrofuran-3-yloxy]ethoxy group, a 2-(tetrahydrofuran-3-ylmethoxy)ethoxy group, a thiazoyl group, a 2-[(4-methoxytetrahydrofuran-3-yl)oxy]ethoxy group, and a 2-(tetrahydro-2H-pyran-4-yloxy)ethoxycarbonyl group.
A compound having the general formula (I) having each substituent as specified below is preferable:
A is a piperidinyl group optionally substituted with group(s) selected from A1, a piperazinyl group optionally substituted with group(s) selected from A1, or a morpholinyl group optionally substituted with group(s) selected from A1, A1 is the following group of substituents:
a hydroxyl group, a halogen atom, a cyano group, a dimethylcarbamoyl group, a diethylcarbamoyl group, an ethylmethylcarbamoyl group,
a C1-C3 alkyl group optionally substituted with group(s) selected from A2,
a C1-C3 alkoxy group optionally substituted with group(s) selected from A2,
a C1-C3 alkylcarbonyl group optionally substituted with group(s) selected from A2,
a C1-C6 alkoxycarbonyl group optionally substituted with group(s) selected from A2,
a cyclohexyl group optionally substituted with group(s) selected from A2,
a phenyl group optionally substituted with group(s) selected from A2,
a phenoxy group optionally substituted with group(s) selected from A2,
a benzoyl group optionally substituted with group(s) selected from A2,
a 3- to 10-membered heterocyclyl group optionally substituted with group(s) selected from A2,
a 3- to 10-membered heterocyclyloxy group optionally substituted with group(s) selected from A2, and
a 3- to 10-membered heterocyclylcarbonyl group optionally substituted with group(s) selected from A2, A2 is the following group of substituents:
a hydroxyl group, a halogen atom, a cyano group, a nitro group, a dimethylcarbamoyl group, a diethylcarbamoyl group, an ethylmethylcarbamoyl group, a dimethylaminosulfonyl group,
a carbamoyloxy group optionally substituted with group(s) selected from A3,
a C1-C3 alkylamino group optionally substituted with group(s) selected from A3,
a C1-C3 alkyl group optionally substituted with group(s) selected from A3,
a C1-C3 alkoxy group optionally substituted with group(s) selected from A3,
a cyclopropyloxy group optionally substituted with group(s) selected from A3,
a cyclohexyloxy group optionally substituted with group(s) selected from A3,
a C1-C3 alkylcarbonyl group optionally substituted with group(s) selected from A3,
a halogeno C1-C6 alkyl group,
a halogeno C1-C6 alkoxy group,
a 3- to 10-membered heterocyclyl group optionally substituted with group(s) selected from A3,
a 3- to 10-membered heterocyclyloxy group optionally substituted with group(s) selected from A3,
a 3- to 10-membered heterocyclylcarbonyl group optionally substituted with group(s) selected from A3, and
a 3- to 10-membered heterocyclylsulfonyl group optionally substituted with group(s) selected from A3, A3 is the following group of substituents:
a halogen atom, an amino group, a hydroxyl group, a t-butoxycarbonylamino group, a C1-C6 alkyl group, a C1-C3 alkoxy group, a halogeno C1-C3 alkoxy group, a 3- to 10-membered heterocyclyl group, a 3- to 10-membered heterocyclyloxy group, a dimethylcarbamoyl group, a diethylcarbamoyl group, an ethylmethylcarbamoyl group, and a methylsulfonyl group, B is an amino group, a methylamino group, or an ethylamino group, and X is —N=.

A compound having the general formula (Ia) having each substituent as specified below is preferable:

A1-2 is a hydrogen atom,
A1-1 is a group selected from the following group of substituents:
a dimethylcarbamoyl group,
a C1-C3 alkoxy group optionally substituted with group(s) selected from A2,
a C1-C3 alkoxycarbonyl group optionally substituted with group(s) selected from A2,
a phenyl group optionally substituted with group(s) selected from A2,
a phenoxy group optionally substituted with group(s) selected from A2, and
a 3- to 10-membered heterocyclyl group optionally substituted with group(s) selected from A2, A2 is a group selected from the following group of substituents:
a dimethylcarbamoyl group, a dimethylaminosulfonyl group,
a carbamoyloxy group optionally substituted with group(s) selected from A3,
a C1-C3 alkylamino group optionally substituted with group(s) selected from A3,
a C1-C3 alkyl group optionally substituted with group(s) selected from A3,
a C1-C3 alkoxy group optionally substituted with group(s) selected from A3,
a cyclopropyloxy group optionally substituted with group(s) selected from A3, and
a cyclohexyloxy group optionally substituted with group(s) selected from A3, A3 is a group selected from the following group of substituents:
a 3- to 10-membered heterocyclyl group, a 3- to 10-membered heterocyclyloxy group, a methylsulfonyl group, a methoxy group, and a difluoromethoxy group, Y is —CH—, —CH$_2$—, —NH—, or —N—, B is an amino group, a methylamino group, or an ethylamino group, and X is —N=.

As the compound having the general formula (I), ones demonstrated in Examples are particularly preferable. Particularly, the following compounds are more preferable.

8-piperidin-1-yl-1,6-naphthyridine-2-carboxamide,
8-morpholin-4-yl-1,6-naphthyridine-2-carboxamide,
8-(4-phenylpiperazin-1-yl)-1,6-naphthyridine-2-carboxamide,
8-(4-methoxypiperidin-1-yl)-1,6-naphthyridine-2-carboxamide,
8-[3-(methoxymethyl)piperidin-1-yl]-1,6-naphthyridine-2-carboxamide,
8-{4-[2-(tetrahydro-2H-pyran-4-yloxy)ethoxy]piperidin-1-yl}-1,6-naphthyridine-2-carboxamide,
N-ethyl-8-{4-[2-(tetrahydro-2H-pyran-4-yloxy)ethoxy]piperidin-1-yl}-1,6-naphthyridine-2-carboxamide,
8-{4-[2-(cyclopropyloxy)ethoxy]piperidin-1-yl}-1,6-naphthyridine-2-carboxamide,
8-{4-[2-(dimethylamino)-2-oxoethoxy]piperidin-1-yl}-1,6-naphthyridine-2-carboxamide,
8-[4-(dimethylcarbamoyl)piperazin-1-yl]-1,6-naphthyridine-2-carboxamide,
8-(4-{2-[methyl(methylsulfonyl)amino]ethoxy}piperidin-1-yl)-1,6-naphthyridine-2-carboxamide,
8-[4-(2-ethoxyethoxy)piperidin-1-yl]-1,6-naphthyridine-2-carboxamide, 8-(4-{2-[(3R)-tetrahydrofuran-3-yloxy]ethoxy}piperidin-1-yl)-1,6-naphthyridine-2-carboxamide,
N-ethyl-8-(4-{2-[(3R)-tetrahydrofuran-3-yloxy]ethoxy}piperidin-1-yl)-1,6-naphthyridine-2-carboxamide,
8-(4-{2-[(3S)-tetrahydrofuran-3-yloxy]ethoxy}piperidin-1-yl}-1,6-naphthyridine-2-carboxamide,
N-ethyl-8-(4-{2-[(3S)-tetrahydrofuran-3-yloxy]ethoxy}piperidin-1-yl}-1,6-naphthyridine-2-carboxamide,
8-{4-[2-(tetrahydrofuran-3-ylmethoxy)ethoxy]piperidin-1-yl}-1,6-naphthyridine-2-carboxamide,
N-ethyl-8-{4-[2-(tetrahydrofuran-3-ylmethoxy)ethoxy]piperidin-1-yl}-1,6-naphthyridine-2-carboxamide,
4-piperidin-1-yl-isoquinoline-6-carboxamide,
4-(4-phenylpiperazin-1-yl)isoquinoline-6-carboxamide,
4-morpholin-4-ylisoquinoline-6-carboxamide,
4-[(3S)-3-(methoxymethyl)piperidin-1-yl]isoquinoline-6-carboxamide,
4-[(3R)-3-(methoxymethyl)piperidin-1-yl]isoquinoline-6-carboxamide,
4-[4-(1,3-thiazol-2-yl)piperazin-1-yl]isoquinoline-6-carboxamide,
4-{4-[2-(tetrahydro-2H-pyran-4-yloxy)ethoxy]piperidin-1-yl}isoquinoline-6-carboxamide,
4-{4-[2-(cyclopropyloxy)ethoxy]piperidin-1-yl}isoquinoline-6-carboxamide,
trans-8-(4-{2-[(4-methoxytetrahydrofuran-3-yl)oxy]ethoxy}piperidin-1-yl)-1,6-naphthyridine-2-carboxamide, and
2-(tetrahydro-2H-pyran-4-yloxy)ethyl 4-(2-carbamoyl-1,6-naphthyridin-8-yl)piperazine-1-carboxylate.

The phrase "optionally substituted with" preferably refers to either being unsubstituted or being substituted with one to three substituents.

The "3- to 10-membered heterocyclyl group" refers to an azetidinyl group, a pyrrolidinyl group, a 1,4-dioxanyl group, a hexahydrofuro[3.2.b]furanyl group, a piperidinyl group, a morpholinyl group, a piperazinyl group, an azepanyl group, a 1,4-diazepanyl group, a pyrrolyl group, a thiazoyl group, a pyridyl group, a tetrahydropyridyl group, a tetrahydropyranyl group, a tetrahydrofuranyl group, a tetrahydroisoquinolinyl group, or a decahydroisoquinolinyl group.

The "3- to 10-membered heterocyclyloxy group" is the aforementioned 3- to 10-membered heterocyclyl group to which an oxygen atom is bound, and refers to an azetidinyloxy group, a pyrrolidinyloxy group, a piperidinyloxy group, a morpholinyloxy group, a piperazinyloxy group, an azepanyloxy group, a 1,4-diazepanyloxy group, a pyrrolyloxy group, a thiazoyloxy group, a pyridyloxy group, a tetrahydropyridyloxy group, a tetrahydropyranyloxy group, a tetrahydrofuranyloxy group, a tetrahydroisoquinolinyloxy group, or a decahydroisoquinolinyloxy group.

The "3- to 10-membered heterocyclylcarbonyl group" is the aforementioned 3- to 10-membered heterocyclyl group to which a carbonyl group is bound, and refers to an azetidinylcarbonyl group, a pyrrolidinylcarbonyl group, a piperidinylcarbonyl group, a morpholinylcarbonyl group, a piperazinylcarbonyl group, a 1,4-dioxanylcarbonyl group, an azepanylcarbonyl group, a 1,4-diazepanylcarbonyl group, a pyrrolylcarbonyl group, a thiazoylcarbonyl group, a pyridylcarbonyl group, a tetrahydropyridylcarbonyl group, a tetrahydropyranylcarbonyl group, a tetrahydrofuranylcarbonyl group, a tetrahydroisoquinolinylcarbonyl group, or a decahydroisoquinolinylcarbonyl group.

The "3- to 10-membered heterocyclylsulfonyl group" is the aforementioned 3- to 10-membered heterocyclyl group to which a sulfonyl group is bound, and refers to an azetidinylsulfonyl group, a pyrrolidinylsulfonyl group, a piperidinylsulfonyl group, a morpholinylsulfonyl group, a piperazinylsulfonyl group, an azepanylsulfonyl group, a 1,4-diazepanylsulfonyl group, a pyrrolylsulfonyl group, a thiazoylsulfonyl group, a pyridylsulfonyl group, a tetrahydropyridylsulfonyl group, a tetrahydropyranylsulfonyl group, a tetrahydrofuranylsulfonyl group, a tetrahydroisoquinolinylsulfonyl group, or a decahydroisoquinolinylsulfonyl group.

The "C1-C6 alkyl group" is a linear or branched alkyl group having a carbon number of 1 to 6, and is preferably a methyl group, an ethyl group, a propyl group, an isopropyl group, or a t-butyl group.

The "C1-C6 alkoxy group" is the aforementioned C1-C6 alkyl group to which an oxygen atom is bound, and is preferably a methoxy group, an ethoxy group, a propoxy group, an isopropoxy group, or a t-butoxy group.

The "C1-C6 alkoxycarbonyl group" is the aforementioned C1-C6 alkoxy group to which a carbonyl group is bound, and is preferably a methoxycarbonyl group, an ethoxycarbonyl group, a propoxycarbonyl group, an isopropoxycarbonyl group, or a t-butoxycarbonyl group.

The "C1-C6 alkylcarbonyl group" is the aforementioned C1-C6 alkyl group to which a carbonyl group is bound, and is preferably an acetyl group, an ethylcarbonyl group, a propylcarbonyl group, an isopropylcarbonyl group, or a butylcarbonyl group.

The "C1-C6 alkylsulfonyl group" is the aforementioned C1-C6 alkyl group to which a sulfonyl group is bound, and is preferably a methylsulfonyl group, an ethylsulfonyl group, a propylsulfonyl group, an isopropylsulfonyl group, or a butylsulfonyl group, of which a methylsulfonyl group or an ethylsulfonyl group is more preferable.

The "hydroxy C1-C6 alkyl group" is the aforementioned C1-C6 alkyl group to which a hydroxyl group is bound, and is preferably a hydroxymethyl group, a hydroxyethyl group, and a hydroxypropyl group, of which a hydroxymethyl group and a hydroxyethyl group are more preferable.

The "C3-C6 cycloalkyl group" is a cyclic alkyl group having a carbon number of 3 to 6, and is preferably a cyclopropyl group, a cyclobutyl group, a cyclopentyl group, or a cyclohexyl group.

The "C3-C6 cycloalkoxy group" is the aforementioned C3-C6 cycloalkyl group to which an oxygen atom is bound, and is preferably a cyclopropyloxy group, a cyclobutyloxy group, a cyclopentyloxy group, or a cyclohexyloxy group.

The "C6-C10 aryl group" is a phenyl group, an indenyl group, and a naphthyl group, of which a phenyl group is preferable.

The "C6-C10 aryloxy group" is the aforementioned C6-C10 aryl group to which an oxygen atom is bound, and is a phenoxy group, an indenyloxy group, and a naphthyloxy group, of which a phenoxy group is preferable.

The "C6-C10 arylcarbonyl group" is the aforementioned C6-C10 aryl group to which a carbonyl group is bound, and is a benzoyl group, an indenylcarbonyl group, and a naphthylcarbonyl group, of which a benzoyl group is preferable.

The "di C1-C6 alkylcarbamoyl group" is the aforementioned C1-C6 alkyl group to which a carbamoyl group is bound, and is preferably a dimethylcarbamoyl group, a diethylcarbamoyl group, or an ethylmethylcarbamoyl group.

The "di C1-C6 alkylaminosulfonyl group" is the aforementioned C1-C6 alkyl group to which an aminosulfonyl group is bound, and is preferably a dimethylaminosulfonyl group.

The "C1-C6 alkoxycarbonylamino group" is the aforementioned C1-C6 alkoxy group to which a carbonylamide group is bound, and is preferably a t-butoxycarbonylamino group.

The "C1-C6 alkylamino group" is an amino group to which one of the aforementioned C1-C6 alkyl groups is bound, and is preferably a methylamino group, an ethylamino group, a propylamino group, an isopropylamino group, or a butylamino group.

The "halogeno C1-C6 alkyl group" is the aforementioned C1-C6 alkyl group that is substituted with halogen atom(s). Examples thereof include a fluoromethyl group, a difluoromethyl group, a trifluoromethyl group, a fluoroethyl group, a difluoroethyl group, a trifluoroethyl group, a fluoropropyl group, a difluoropropyl group, a trifluoropropyl group, a fluorobutyl group, a difluorobutyl group, a trifluorobutyl group, a fluoropentyl group, a difluoropentyl group, a trifluoropentyl group, a fluorohexyl group, a difluorohexyl group, a trifluorohexyl group, a pentafluoroethyl group, a hexafluoropropyl group, a nonafluorobutyl group, a chloromethyl group, a dichloromethyl group, a trichloromethyl group, a chloroethyl group, a dichloroethyl group, a trichloroethyl group, a chloropropyl group, a dichloropropyl group, and a trichloropropyl group.

The "halogeno C1-C6 alkoxy group" is the aforementioned C1-C6 alkoxy group that is substituted with halogen atom(s). Examples thereof include a fluoromethoxy group, a difluoromethoxy group, a trifluoromethoxy group, a fluoroethoxy group, a difluoroethoxy group, a trifluoroethoxy group, a fluoropropoxy group, a difluoropropoxy group, a trifluoropropoxy group, a fluorobutoxy group, a difluorobutoxy group, a trifluorobutoxy group, a fluoropentyloxy group, a difluoropentyloxy group, a trifluoropentyloxy group, a fluorohexyloxy group, a difluorohexyloxy group, a trifluorohexyloxy group, a pentafluoroethoxy group, a hexafluoropropoxy group, a nonafluorobutoxy group, a chloromethoxy group, a dichloromethoxy group, a trichloromethoxy group, a chloroethoxy group, a dichloroethoxy group, a trichloroethoxy group, a chloropropoxy group, a dichloropropoxy group, or a trichloropropoxy group.

The "halogen atom" can be, for example, a fluorine atom, a chlorine atom, a bromine atom, or an iodine atom, of which a fluorine atom or a chlorine atom is preferable.

The term "treatment" refers to curing or improving diseases or symptoms, or suppressing symptoms.

The "pharmacologically acceptable salt thereof" refers to a salt that can be used as a medicine (for example, ones listed in J. Pharm. Sci., 66: 1-19 (1977)). The compound of the present invention having an acidic group or a basic group can be obtained as a basic salt or an acidic salt through reaction with a base or an acid, respectively; therefore, such a salt is referred to as the "pharmacologically acceptable salt thereof."

Preferable examples of a pharmacologically acceptable "basic salt" of the compound of the present invention include an alkali metal salt such as a sodium salt, a potassium salt, and a lithium salt; an alkaline earth metal salt such as a magnesium salt and a calcium salt; an organic basic salt such as an N-methylmorpholine salt, a triethylamine salt, a tributylamine salt, a diisopropylethylamine salt, a dicyclohexylamine salt, an N-methylpiperidine salt, a pyridine salt, a 4-pyrrolidinopyridine salt, and a picoline salt; or an amino acid salt such as a glycine salt, a lysine salt, an arginine salt, an ornithine salt, a glutamic acid salt, and an aspartic acid salt, of which an alkali metal salt is preferable.

Preferable examples of a pharmacologically acceptable "acidic salt" of the compound of the present invention include a hydrohalide such as hydrofluoride, hydrochloride, hydrobromide, and hydroiodide, an inorganic acid salt such as nitrate, perchlorate, sulfate, and phosphate; an organic acid salt such as lower alkanesulfonate such as methanesulfonate, trifluoromethanesulfonate, and ethanesulfonate, arylsulfonate such as benzenesulfonate and p-toluenesulfonate, an organic acid salt such as acetate, malate, fumarate, succinate, citrate, ascorbate, tartrate, oxalate, and maleate; and an amino acid salt such as a glycine salt, a lysine salt, an arginine salt, an ornithine salt, a glutamic acid salt, and an aspartic acid salt, of which a hydrohalide is most preferable.

The compound of the present invention or the pharmacologically acceptable salt thereof may absorb water, contain hygroscopic water, or form a hydrate, when left in the atmosphere or subjected to recrystallization. The present invention also encompasses compounds in such various forms of hydrates, solvates, and crystal polymorphs.

The compound of the present invention, a salt thereof, or a solvate thereof may be present as various isomers such as geometric isomers including a cis-form, a trans-form, etc., tautomers, or enantiomers such as a D-form and an L-form, depending on the kind and combination of substituents. Unless otherwise specifically restricted, the compound of the present invention encompasses all of these isomers and stereoisomers, and a mixture containing these isomers and stereoisomers in any ratio. A mixture of these isomers can be separated by publicly known means of partitioning.

The compound of the present invention also encompasses a labeled compound, namely the compound of the present invention in which one or more atoms are substituted with radioactive or nonradioactive isotopes (for example, $^{2}$H, $^{3}$H, $^{13}$C, $^{14}$C, and $^{35}$S).

Further, the present invention also encompasses pharmacologically acceptable so-called prodrugs of the compound of the present invention. A pharmacologically acceptable prodrug is a compound having a group that can be converted into an amino group, a hydroxyl group, a carboxyl group, and the like of the compound of the invention by hydrolysis or under physiological conditions. Examples of a group forming such a prodrug include ones described in Prog. Med., Vol. 5, pages 2157 to 2161, 1985; Iyakuhin no kaihatu (literal translation: development of pharmaceutical product) (Hirokawa Shoten Ltd.) Vol. 7, Bunshi Sekkei (literal translation: molecular design) pages 163 to 198; Advanced Drug Delivery Reviews (1996) 19(2): 115 to 130, etc. More specifically, examples of the prodrug of the compound of the present invention having an amino group include the compound in which the amino group is acylated, alkylated, or phosphorylated (for example, the compound in which the amino group is converted into eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, and tert-butyl). Also, more specifically, examples of the prodrug of the compound of the present invention having a hydroxyl group include the compound in which the hydroxyl group is acylated, alkylated, phosphorylated, or borated (for example, the compound in which the hydroxyl group is converted into acetyl, palmitoyl, propanoyl, pivaloyl, succinyl, fumaryl, alanyl, and dimethylaminomethylcarbonyl). Also, more specifically, examples of the prodrug of the compound of the present invention having a carboxyl group include the compound in which the carboxyl group is esterified or amidated (for example, the compound in which the carboxyl group is ethyl-esterified, phenyl-esterified, carboxymethyl-esterified, dimethylaminomethyl-esterified, pivaloyloxymethyl-esterified, ethoxycarbonyloxyethyl-esterified, amidated, or methylamidated).

(Production Method)

The compound of the present invention can be produced by applying various publicly known production methods, while taking advantage of the characteristics based on the basic structure of the compound or the kind of the substituent. Examples of the publicly known method include methods described in "ORGANIC FUNCTIONAL GROUP PREPARATIONS", second edition, ACADEMIC PRESS, INC., 1989, and "Comprehensive Organic Transformations", VCH Publishers Inc., 1989, and the like.

Upon production of the compound of the present invention, depending on the kind of the functional group, it may be effective, from the production technique point of view, to protect the function group of a raw material or intermediate compound with an appropriate protective group or replace the functional group by a readily-convertible group in advance.

Examples of the functional group include an amino group, a hydroxyl group, and a carboxyl group, and examples of the protective group thereof include ones described in "Protective Groups in Organic Synthesis (third edition, 1999)" written by T. W. Greene and P. G. Wuts. These protective groups can be appropriately selected in accordance with their reaction conditions. According to these methods, a desired compound can be obtained by introducing the substituent and carrying out the reaction, and then removing a protective group or converting the substituent into a desired group, as needed.

Further, a prodrug of the compound of the present invention can be produced by, similarly to the aforementioned protective groups, introducing a specific group into a raw material or intermediate compound, or carrying out the reactions using the compound of the present invention produced. The reaction can be carried out by applying a method publicly known to those skilled in the art such as methods normally performed, for example, esterification, amidation, dehydration, and hydrogenation.

Hereinbelow, the production method of the compound of the present invention will be described. However, the production method is not limited to the below-described methods in any way.

An overview of the production method of the compound of the present invention is shown below. That is, the compound of the present invention (I) can be produced, using a compound (I') as a raw material, by a method including principle steps of (1) introducing a heterocyclyl group "A" in the presence of palladium catalysts and (2) carrying out an amidation reaction using B—H.

[Chemical Formula 3]

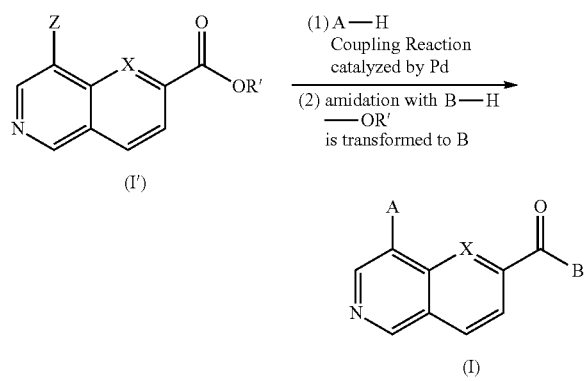

Z: Halogen or CF$_3$SO$_2$O—
R': alkyl, aryl, aralkyl
B—H: ammonia, primary or secondary amine Further, the production method in which the heterocyclyl group "A" contains a nitrogen atom as a hetero atom will be described in detail below.

[Chemical formula 4]

Synthetic Method toward Naphthyridine Derivatives Method A

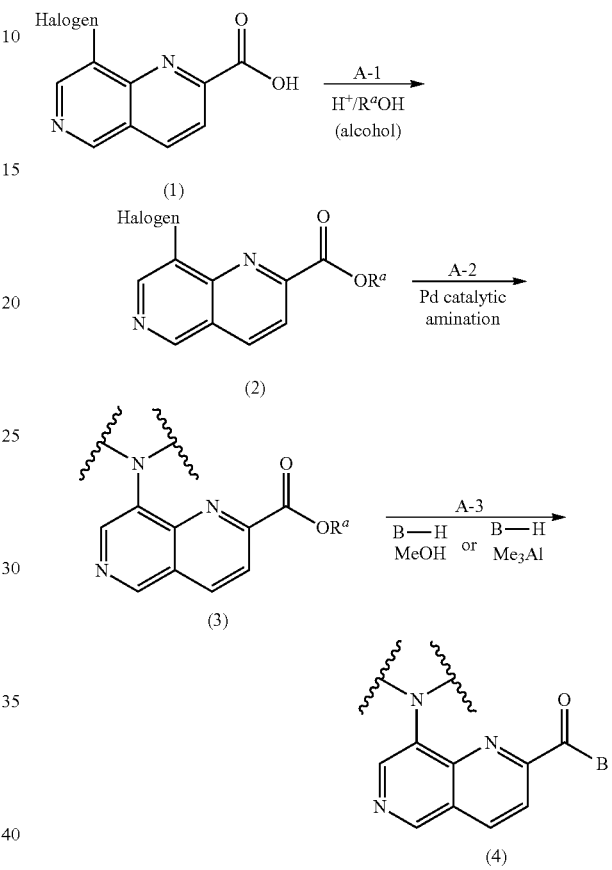

R$^a$: alkyl group, aryl gorup or aralkyl group
B—H: ammonia, primary or secondary amine The production method A is a method for producing a naphthyridine compound (4) of the present invention, including the following steps:

A-1: converting a compound (1) into a compound (2) by an esterification reaction of a carboxyl group using an acid catalyst and the like in an alcohol solvent, A-2: reacting a cyclic amine compound with the compound (2) in the presence of a palladium catalyst to replace the halogen group on the naphthyridine ring of the compound (2) by a cyclic amino group to produce a compound (3), and A-3: performing an amidation reaction between the ester group of the compound (3) and an amine to produce the compound (4), the compound of the present invention.

[Chemical formula 5]

Synthetic Method toward Naphthyridine Derivatives Method B (1) 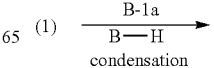

-continued (2)

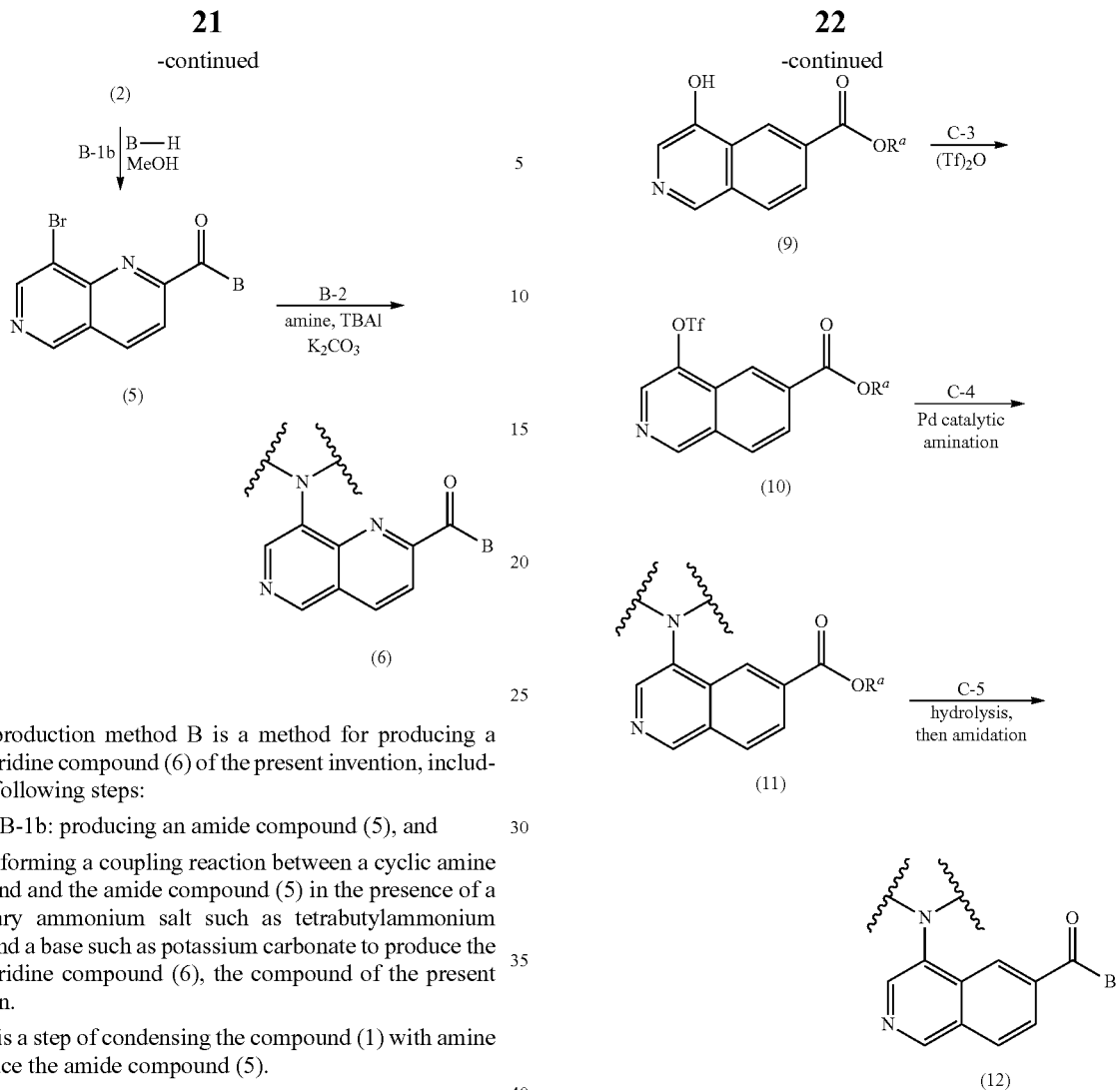

The production method B is a method for producing a naphthyridine compound (6) of the present invention, including the following steps:

B-1a or B-1b: producing an amide compound (5), and

B-2: performing a coupling reaction between a cyclic amine compound and the amide compound (5) in the presence of a quaternary ammonium salt such as tetrabutylammonium iodide and a base such as potassium carbonate to produce the naphthyridine compound (6), the compound of the present invention.

B-1a is a step of condensing the compound (1) with amine to produce the amide compound (5).

B-1b is a step of reacting the compound (2) with an amine to replace the ester group by an amide group to produce the amide compound (5).

[Chemical formula 6]

Synthetic Method toward Isoquinoline Derivatives Method C

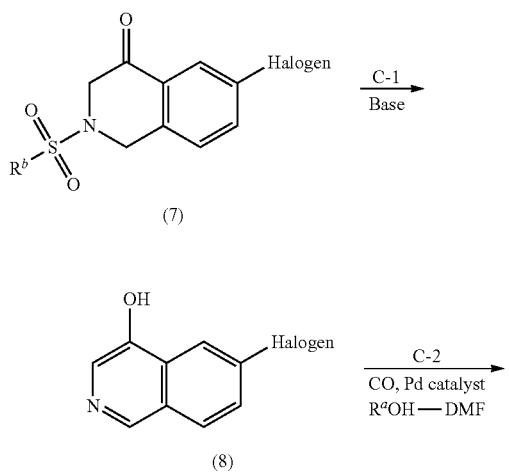

$R^b$: alkyl group, aryl gorup or aralkyl group

The production method C is a method for producing an isoquinoline compound (12) of the compound of the present invention, including the following steps:

C-1: treating a compound (7) with a base to convert it into a compound (8),

C-2: reacting carbon monoxide and an alcohol with the compound (8) in the presence of a palladium catalyst to produce an ester compound (9), C-3: trifluoromethanesulfonylating the phenolic hydroxyl group of the compound (9) to produce a compound (10), C-4: similarly to A-2, performing a reaction on the compound (10) in the presence of a palladium catalyst to produce a compound (11), and C-5: hydrolyzing the ester group of the compound (11) to generate a carboxyl group, and performing a condensation reaction between an amine and the carboxyl group to produce the isoquinoline compound (12), the compound of the present invention.

The coupling reaction performed in the presence of a palladium catalyst in the steps A-2 and C-4 will be explained below.

[Chemical formula 7]

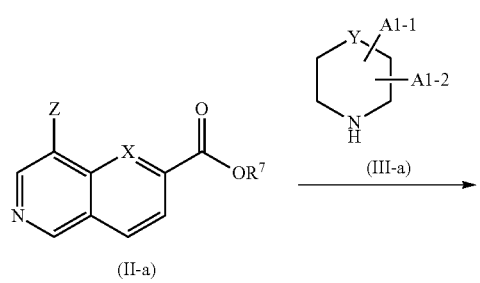

(II-a)　(III-a)

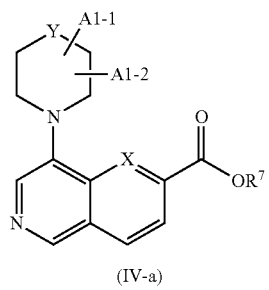

(IV-a)

wherein A1-1, A1-2, B, X, and Y refer to the same groups as described above. $R^7$ refers to a hydrogen atom or a protective group of a carboxyl group. Z refers to a group that can serve as a leaving group during the coupling reaction.

A commercially available compound or a compound produced in accordance with the method described in the literature (for example, Journal of Medicinal Chemistry, 42, 16, 1999, 3023 to 3025, Journal of Medicinal Chemistry, 40, 18, 1997, 2910 to 2921, Bioorg. Med. Chem. 11 (2003) 1451 to 1464, and Tetrahedron, 61 (2005) 8282 to 8287) is used as a compound having the general formula (II-a). A commercially available compound or a compound produced in accordance with a publicly known method can be used as a compound having the general formula (III-a).

A compound having the general formula (IV-a) can be produced through a coupling reaction between the compound having the general formula (II-a) and the compound having the general formula (III-a). This coupling reaction is carried out while heating in the presence of a palladium catalyst, a ligand, a base, and a solvent. This coupling reaction can be performed in accordance with the methods described in, for example, Journal of Organic Chemistry, 71, 10, 2006, 3816 to 3821, Chemistry A European Journal, 12, 19, 2006, 5142 to 5148, Organic Letters, 5, 6, 2003, 815 to 818, and Journal of Organic Chemistry, 73, 4, 2008, 1429 to 1434.

The amidation reaction in the steps A-3, B-1a, B-1b, and C-5 will be explained below.

[Chemical formula 8]

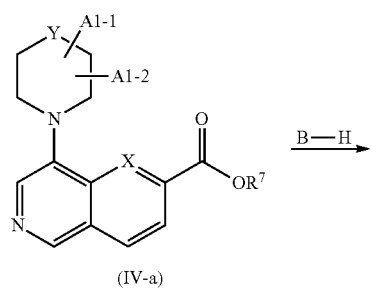

(IV-a)

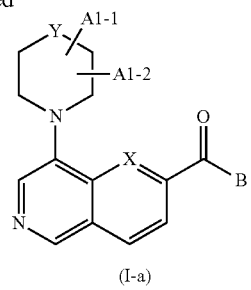

(I-a)

The amidation reaction is carried out using a compound having the general formula (IV-a) and B—H. This amidation reaction can be carried out in accordance with the methods described in, for example, Chem. Rev., 1948, 45, 203, J. Am. Chem. Soc., 1950, 72, 1888, Org. Biol. Chem., 1962, 84, 4457, J. Am. Chem. Soc., 1973, 95, 875, and J. Am. Chem. Soc., 1981, 103, 7090.

The coupling reaction in the step B-2 will be explained below.

[Chemical formula 9]

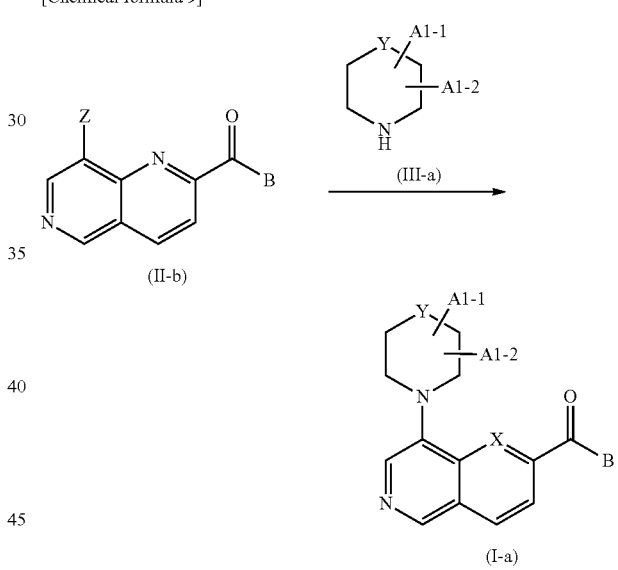

wherein A1-1, A1-2, B, X, Y, and Z refer to the same groups as described above.

A commercially available compound or a compound produced in accordance with the methods described in the literature is used as a compound having the general formula (II-b). A commercially available compound or a compound produced in accordance with a publicly known method can be used as a compound having the general formula (III-a).

A compound having the general formula (I-a) can be produced through a coupling reaction between the compound having the general formula (II-b) and the compound having the general formula (III-a). This coupling reaction is carried out while heating in the presence of a base, a quaternary ammonium salt, and a solvent, or in the absence of a solvent. This coupling reaction can be performed in accordance with the method described in, for example, Journal of Medicinal Chemistry, 48, 7, 2005, 2388 to 2406.

The compound of the present invention produced by the aforementioned method can be isolated and purified by a publicly known method, for example, extraction, precipitation, distillation, chromatography, fractional crystallization, and recrystallization.

Also, in the case that the compound having the general formula (I) of the present invention or a production intermediate thereof contains asymmetric carbon, enantiomers exist. Each of these enantiomers can be isolated and purified by a standard method such as fractional crystallization (salt fractionation) in which an enantiomer is recrystallized with an appropriate salt, and column chromatography. Examples of reference literature for a method of separating an enantiomer from racemates include J. Jacques et al., "Enantiomers, Racemates and Resolution, John Wiley And Sons, Inc."

The compound of the present invention is highly safe and exhibits favorable disposition, and also, has an excellent osteogenesis-promoting action. Hence, the compound of the present invention can be used for the prevention or treatment (particularly, treatment) of diseases associated with bone metabolism such as osteoporosis, Paget's disease of bone, and osteoarthritis, and thus is useful.

When administering the compound of the present invention or a pharmacologically acceptable salt thereof to a mammal (particularly, a human), it can be administered systemically or locally by the oral or parenteral route.

The dosage form of the pharmaceutical composition of the present invention is selected depending on the administration method, and is producible by preparation methods normally employed for various kinds of formulations.

Examples of dosage forms for an oral pharmaceutical composition include a tablet, a pill, a powder, a granule, a capsule, a liquid medicine, a suspension, an emulsion, a syrup, and an elixir. Medicines in these dosage forms can be prepared by standard methods, using any agent appropriately selected as needed from among those normally employed as additives such as an excipient, a binder, a disintegrant, a lubricant, a swelling agent, a swelling aid, a coating agent, a plasticizer, a stabilizer, an antiseptic, an antioxidant, a colorant, a solubilizing aid, a suspending agent, an emulsifier, a sweetener, a preservative, a buffer, a diluent, and a humectant.

Examples of dosage forms for a parenteral pharmaceutical composition include an injection, an ointment, a gel, a cream, a poultice, an aerosol, an inhalant, a spray, an eye drop, a nasal drop, and a suppository. Medicines in these dosage forms can be prepared by standard methods, using any agent appropriately selected as needed from among those normally employed as additives such as a stabilizer, an antiseptic, a solubilizing aid, a humectant, a preservative, an antioxidant, a fragrance, a gelling agent, a neutralizer, a solubilizing aid, a buffer, an isotonic agent, a surfactant, a colorant, a buffer, a viscosity enhancer, a humectant, a filler, an absorption promoter, a suspending agent, and a binder.

The dose of the compound having the general formula (I) or a pharmacologically acceptable salt thereof varies depending on the symptoms, age, body weight, and the kind, dose, etc. of a drug to be administered in combination. However, normally, the compound having the general formula (I) or a pharmacologically acceptable salt thereof is preferably administered in a range of from 0.001 mg to 1000 mg, in terms of the amount of the compound having the general formula (I), per adult (presumed to weigh approximately 60 kg) per dose, systemically or locally, once to several times a month, once to several times a week, or once to several times a day, orally or parenterally, or via the intravenous route continuously for one to 24 hours a day.

Further, other active ingredients can be used in combination with the pharmaceutical composition of the present invention as needed as long as such active ingredient does not impair the efficacy of the present invention.

The present invention also encompasses a method for preventing/treating the aforementioned diseases, comprising administering the compound of the present invention or a pharmacologically acceptable salt thereof.

The present invention further encompasses use of the compound of the present invention or a pharmacologically acceptable salt thereof for the production of the aforementioned pharmaceutical composition.

Formulation Example 1

Powder

Five grams of the compound of the present invention, 895 g of lactose, and 100 g of corn starch are mixed by a blender to give a powder.

Formulation Example 2

Granule

Five grams of the compound of the present invention, 865 g of lactose, and 100 g of low-substituted hydroxypropylcellulose are mixed, followed by addition of 300 g of a 10% aqueous solution of hydroxypropylcellulose. The resulting mixture is kneaded and granulated using extrusion granulation equipment, and then dried to give a granule.

Formulation Example 3

Tablet

Five grams of the compound of the present invention, 90 g of lactose, 34 g of corn starch, 20 g of crystalline cellulose, and 1 g of magnesium stearate are mixed by a blender, followed by tabletting using a tablet machine to give a powder.

Test Example

Test Example 1

Osteoblast Differentiation Test

ST2 cells, murine bone marrow-derived stromal cells, (obtained from RIKEN) were used.

In this test, α-MEM media (obtained from GIBCO BRL Cat. No. 10370-021) containing 10% (v/v) of inactivated calf serum (obtained from Hyclone Laboratories, Inc.) and 1% (v/v) of Penicillin-Streptomycin Liquid (obtained from GIBCO BRL Cat. No. 15140-122) (hereinbelow, abbreviated as 10%-FBS-αMEM) were used. In this test, all culturing was performed in a $CO_2$ incubator (37° C., 95% humidity, 5% $CO_2$).

The aforementioned cells were detached with 2 mL of a 0.25% trypsin solution (obtained from GIBCO BRL Cat. No. 15050-065) and dispersed in 10 mL of 10%-FBS-αMEM. Subsequently, the cells were collected by centrifugation (25° C., 800 rpm, five minutes). Then, a cell suspension containing 40000 of the cells/mL of 10%-FBS-αMEM was prepared. The cell suspension was then dispensed into 96-well plates (the product of Falcon), 100 µL per well, at a density of 4000 cells/well, followed by culturing for 24 hours. To the wells except for the below-described well containing a control group, the compound was dispensed at final concentrations of 0.01, 0.03, 0.1, and 0.3 µg/ml. To the well of a control group, DMSO was dispensed at a final concentration of 0.1% (v/v). After four days of culturing, the activity of alkaline phosphatase (ALP) was measured in each group.

The measurement of ALP activity was performed as follows. That is, the medium in each well of the culture plates was completely removed. Each well was then washed by dispensing 100 µL of Dulbecco's phosphate buffer (obtained from GIBCO BRL Cat. No. 14190-144) and then removing it. A cell lysate solution containing 10 mM $MgCl_2$ and 2% (v/v) TritonX-100 (Sigma) was prepared and dispensed at 50 µL/well, followed by stirring at room temperature for five minutes. An ALP substrate solution containing 50 mM diethanolamine (Wako pure chemical industries, Ltd., Cat. No. 099-03112) and 20 mM p-nitrophenyl phosphate (Wako pure chemical industries, Ltd., Cat. No. 147-02343) was prepared and dispensed at 50 µL/well, and the plates were left to stand at room temperature for 10 minutes. Subsequently, absorbance was measured by a microplate reader (Bio-Rad Laboratories, Inc.). Setting the measurement value of the control group of each plate at 100%, the increase (%) in alkaline phosphatase activity in the test compound-addition group was calculated, which was assessed as the degree of osteoblast differentiation.

In this test, the compounds of Examples 1 to 12, 15 to 21, 23, 24, 28, 32, 34 to 50, 52 to 57, 59 to 85, 87, 89, 91 to 95, 97, 99, 100, 102 to 106, and 108 to 117 exhibited an increase of 200% or more in alkaline phosphatase activity at 0.03 µg/mL.

Test Example 2

Osteoclast Formation-Inhibition Test

Eighteen day-old ICR mice are purchased from Japan SLC, Inc. and used in the following experiment. Mice are sacrificed by cervical dislocation, and the left and right femur and the tibia are excised. After removal of surrounding tissues, the femur and the tibia thus excised are minced with scissors. To the femur and the tibia thus minced, 10 mL of 15%-FBS-αMEM is added, followed by stirring for one minute. Subsequently, the supernatant is collected, which is filtered through a cell strainer (Becton, Dickinson and Company). Then, a suspension of 500 thousand cells/mL of 15%-FBS-αMEM is prepared. The cell suspension is then dispensed into 96-well microplates, 100 µL per well, at a density of 50000 cells/well, followed by culturing for 24 hours. Activated vitamin D3 (Sigma, Cat. No. D1530) is dispensed into each well at a final concentration of 20 nM. To the wells except for the below-described well containing a control group, the compound is dispensed at final concentrations of 0.01, 0.03, 0.1, and 0.3 µg/ml. To the well of a control group, DMSO is dispensed at a final concentration of 0.1% (v/v). After five days of culturing, the activity of tartrate-resistant acid phosphatase (TRAP) is measured in each group.

The measurement of TRAP activity is performed as follows. That is, the medium in each well of the culture plates is completely removed. Each well is then washed by dispensing 100 µL of Dulbecco's phosphate buffer (obtained from GIBCO BRL Cat. No. 14190-144) and then removing it. An acetone:ethanol mixture (1:1) is added to the wells and left for one minute for fixation. The fixation mixture is then removed and staining is performed using a Leukocyte acid phosphatase kit (Sigma, Cat. No. 387-A) at 37° C. for 30 minutes. After removing the staining liquid, 100 µL of 10% sodium dodecyl sulfate (Wako pure chemical industries, Ltd. Cat. No. 191-07145) is dispensed, followed by stirring for five minutes. Subsequently, absorbance is measured by a microplate reader (Bio-Rad Laboratories, Inc.). Setting the measurement value of the control group of each plate at 100%, the decrease (%) in TRAP activity in the test compound-addition group is calculated, which is assessed as the osteoclast formation-inhibiting activity.

Test Example 3

Effect on Bone Density

Eight to 12 week old female F344 rats were purchased from Charles River Laboratories and used in the following experiment. Rats were anesthetized with an intraperitoneal administration of 40 mg/kg of Somnopentyl (Kyoritsu Seiyaku Corporation), and then oophorectomy or sham surgery was performed. From the day after surgery, a suspension of the test compound in a 0.5% methyl cellulose solution (Wako pure chemical industries, Ltd. Cat. No. 133-14255) was orally administered once a day, six days a week. Six to eight weeks after administration, the rats were euthanized by removal of whole blood from the lower abdominal aorta under Somnopentyl anesthesia, and the left and right femur was excised.

After removal of soft tissues, the bone density of the femur thus excised was measured by a DXA apparatus, DCS-600R (Aloka Co., Ltd.). The bone density was assessed in the whole femur as well as in three equal sections of the whole femur, namely the proximal end, the shaft, and the distal end.

In this test, the compounds of Examples 3, 4, 7, 12, 15, and 17 significantly increased the bone density at 3 mg/kg.

Test Example 4

Effect on Healing of Fracture

Twelve week old female F344 rats are purchased from Charles River Laboratories and used in the following experiment. Under anesthesia with Somnopentyl, bone surgery is performed in accordance with the method of Li et al. (J. Bone Miner. Res 1999, 14: 969 to 979). From the day after surgery, a suspension of the test compound in a 0.5% methyl cellulose solution (Wako pure chemical industries, Ltd. Cat. No. 133-14255) is orally administered once a day, six days a week. Six to 86 weeks after administration, the rats are euthanized by removal of whole blood from the lower abdominal aorta under Somnopentyl anesthesia, and the femur is excised.

After removal of soft tissues, the bone density of the femur thus excised is measured by a bone strength measuring instrument, MZ-500D (Maruto Instrument Co., Ltd.) A three-point bending test is performed, and the strength is assessed at the maximum load.

EXAMPLES

Example 1

8-[4-(2-Methoxyethoxy)piperidin-1-yl]-1,6-naphthyridine-2-carboxamide (1a) Ethyl-8-[4-(2-methoxyethoxy)piperidin-1-yl]-1,6-naphthyridine-2-carboxylate

[Chemical formula 10]

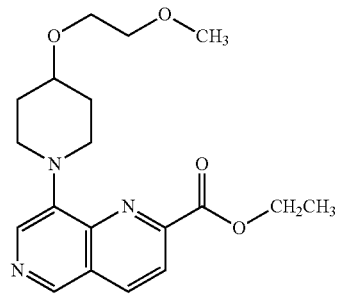

4-(2-Methoxyethoxy)piperidine (239 mg, 1.50 mmol) was dissolved in toluene (1.0 mL), to which ethyl-8-bromo-1,6-naphthyridine-2-carboxylate (281 mg, 1.00 mmol), tris(dibenzylideneacetone)dipalladium (91.6 mg, 0.100 mmol), 2-dicyclohexylphosphino-2'-(N,N-dimethylamino)biphenyl (78.7 mg, 0.200 mmol), and potassium carbonate (powder, 415 mg, 3.00 mmol) were then added, followed by stirring at 100° C. for three hours under a nitrogen atmosphere.

After cooling, the resulting reaction liquid was filtered under suction while washing with dichloromethane. The resulting organic layer was concentrated under reduced pressure. The residue thus obtained was purified by silica gel column chromatography (hexane:ethyl acetate, 30:70-0:100, V/V, ethyl acetate:methanol, 100:0-95:5, V/V) to give the desired title compound (159 mg, yield 44%).

$^1$H-NMR (CDCl$_3$) δ: 1.47 (3H, dt, J=12.8, 5.8 Hz), 1.96-2.05 (2H, m), 2.15-2.22 (2H, m), 3.25-3.31 (2H, m), 3.42 (3H, s), 3.58-3.61 (2H, m), 3.61-3.67 (1H, m), 3.69-3.72 (2H, m), 3.91-3.97 (2H, m), 4.49 (2H, q, J=7.0 Hz), 8.25 (1H, d, J=8.5 Hz), 8.33 (1H, s), 8.37 (1H, d, J=8.5 Hz), 8.90 (1H, s).

(1b) 8-[4-(2-Methoxyethoxy)piperidin-1-yl]-1,6-naphthyridine-2-carboxamide

[Chemical formula 11]

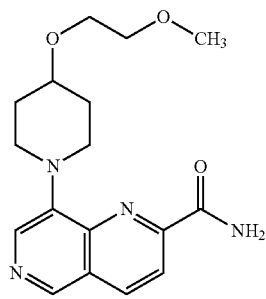

To ethyl-8-[4-(2-methoxyethoxy)piperidin-1-yl]-1,6-naphthyridine-2-carboxylate (158 mg, 0.440 mmol) produced in Example 1 (1a), a 7M ammonia/methanol solution (25 mL, 175 mmol) was added, followed by stirring at 65° C. for one hour.

After cooling, the resulting reaction liquid was concentrated under reduced pressure, and the residue thus obtained was purified by basic silica gel column chromatography (hexane:ethyl acetate, 30:70-0:100, V/V, ethyl acetate:methanol, 100:0-95:5, V/V). Diethyl ether was added to the amorphous substance thus obtained. A solid precipitate was collected by filtration to give the desired title compound (126 mg, yield 87%).

$^1$H-NMR (DMSO-D$_6$) δ: 1.72-1.81 (2H, m), 2.05-2.12 (2H, m), 3.10-3.17 (2H, m), 3.28 (3H, s), 3.46-3.49 (2H, m), 3.53-3.60 (1H, m), 3.59-3.63 (2H, m), 3.74-3.81 (2H, m), 7.82 (1H, br s), 8.00 (1H, br s), 8.23 (1H, d, J=8.3 Hz), 8.31 (1H, s), 8.67 (1H, d, J=8.3 Hz), 9.00 (1H, s).

MS (FAB$^+$) m/z: 331 (M+H)$^+$

Example 2

8-[4-(2-Ethoxyethoxy)piperidin-1-yl]-1,6-naphthyridine-2-carboxamide

[Chemical formula 12]

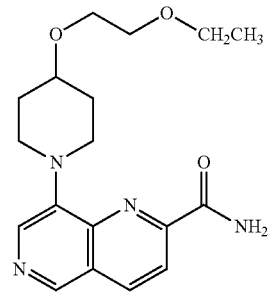

Using 4-(2-ethoxyethoxy)piperidine (1.66 g, 9.56 mmol) and ethyl-8-bromo-1,6-naphthyridine-2-carboxylate (2.07 g, 7.35 mmol), the desired title compound (1.31 g, yield 52%) was obtained by the same method as in Example 1 (1a) and Example 1 (1b).

$^1$H-NMR (DMSO-D$_6$) δ: 1.12 (3H, t, J=7.1 Hz), 1.72-1.82 (2H, m), 2.05-2.12 (2H, m), 3.10-3.17 (2H, m), 3.47 (2H, q, J=7.1 Hz), 3.50-3.62 (5H, m), 3.75-3.81 (2H, m), 7.82 (1H, br s), 8.00 (1H, br s), 8.24 (1H, d, J=8.5 Hz), 8.31 (1H, s), 8.68 (1H, d, J=8.5 Hz), 9.00 (1H, s).

MS (FAB$^+$) m/z: 345 (M+H)$^+$

Example 3

8-(4-{2-[(3R)-Tetrahydrofuran-3-yloxy]ethoxy}piperidin-1-yl)-1,6-naphthyridine-2-carboxamide

[Chemical formula 13]

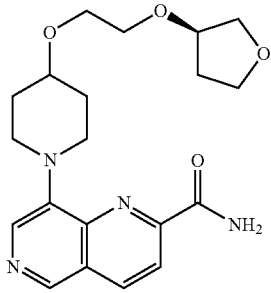

Using 4-{2-[(3R)-tetrahydrofuran-3-yloxy]ethoxy}piperidine (1.56 g, 7.27 mmol) and ethyl-8-bromo-1,6-naphthyridine-2-carboxylate (1.57 g, 5.59 mmol), the desired title compound (838 mg, yield 38%) was obtained by the same method as in Example 1 (1a) and Example 1 (1b).

$^1$H-NMR (DMSO-D$_6$) δ: 1.73-1.81 (2H, m), 1.85-1.99 (2H, m), 2.05-2.11 (2H, m), 3.11-3.17 (2H, m), 3.50-3.81 (11H, m), 4.14-4.18 (1H, m), 7.82 (1H, br s), 8.00 (1H, br s), 8.24 (1H, d, J=8.6 Hz), 8.31 (1H, s), 8.67 (1H, d, J=8.6 Hz), 9.00 (1H, s).

MS (FAB$^+$) m/z: 387 (M+H)$^+$

Example 4

8-(4-{2-[(3S)-Tetrahydrofuran-3-yloxy]ethoxy}piperidin-1-yl)-1,6-naphthyridine-2-carboxamide

[Chemical formula 14]

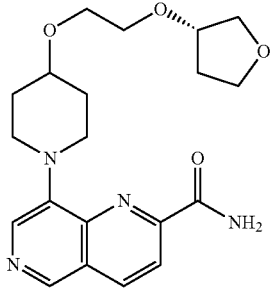

Using 4-{2-[(3S)-tetrahydrofuran-3-yloxy]ethoxy}piperidine (1.52 g, 7.07 mmol) and ethyl-8-bromo-1,6-naphthyridine-2-carboxylate (1.53 g, 5.44 mmol), the desired title compound (842 mg, yield 40%) was obtained by the same method as in Example 1 (1a) and Example 1 (1b).

$^1$H-NMR (DMSO-D$_6$) δ: 1.73-1.81 (2H, m), 1.85-1.98 (2H, m), 2.05-2.11 (2H, m), 3.11-3.17 (2H, m), 3.50-3.80 (11H, m), 4.14-4.18 (1H, m), 7.82 (1H, br s), 8.00 (1H, br s), 8.24 (1H, d, J=8.6 Hz), 8.31 (1H, s), 8.67 (1H, d, J=8.6 Hz), 9.00 (1H, s).

MS (FAB$^+$) m/z: 387 (M+H)$^+$

Example 5

8-{4-[2-(Tetrahydrofuran-3-ylmethoxy)ethoxy]piperidin-1-yl}-1,6-naphthyridine-2-carboxamide

[Chemical formula 15]

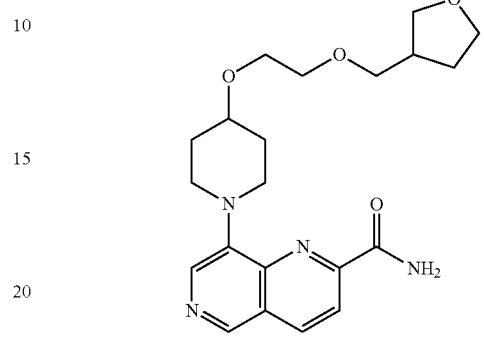

Using 4-[2-(tetrahydrofuran-3-ylmethoxy)ethoxy]piperidine (1.52 g, 6.16 mmol) and ethyl-8-bromo-1,6-naphthyridine-2-carboxylate (1.33 g, 4.73 mmol), the desired title compound (688 mg, yield 37%) was obtained by the same method as in Example 1 (1a) and Example 1 (1b).

$^1$H-NMR (DMSO-D$_6$) δ: 1.48-1.55 (1H, m), 1.73-1.82 (2H, m), 1.87-1.95 (1H, m), 2.05-2.12 (2H, m), 2.40-2.47 (1H, m), 3.15-3.21 (2H, m), 3.31-3.36 (1H, m), 3.38-3.44 (1H, m), 3.53-3.63 (6H, m), 3.67-3.72 (2H, m), 3.76-3.82 (2H, m), 7.83 (1H, br s), 8.02 (1H, br s), 8.26 (1H, d, J=8.5 Hz), 8.32 (1H, s), 8.71 (1H, d, J=8.5 Hz), 9.04 (1H, s).

MS (FAB$^+$) m/z: 401 (M+H)$^+$

Example 6

8-{4-[2-(Tetrahydro-2H-pyran-4-yloxy)ethoxy]piperidin-1-yl}-1,6-naphthyridine-2-carboxamide

[Chemical formula 16]

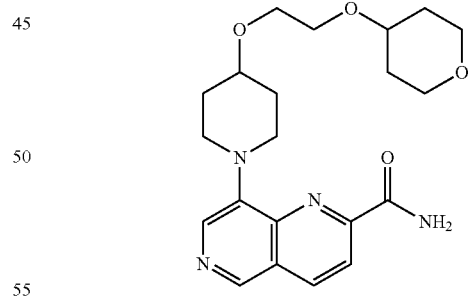

Using 4-[2-(tetrahydro-2H-pyran-4-yloxy)ethoxy]piperidine (1.00 g, 4.37 mmol) and ethyl-8-bromo-1,6-naphthyridine-2-carboxylate (812 mg, 2.91 mmol), the desired title compound (400 mg, yield 34%) was obtained by the same method as in Example 1 (1a) and Example 1 (1b).

$^1$H-NMR (DMSO-D$_6$) δ: 1.35-1.44 (2H, m), 1.73-1.89 (4H, m), 2.05-2.11 (2H, m), 3.10-3.19 (2H, m), 3.29-3.36 (2H, m), 3.49-3.63 (6H, m), 3.73-3.83 (4H, m), 7.82 (1H, br s), 7.99 (1H, br s), 8.23 (1H, d, J=8.5 Hz), 8.31 (1H, s), 8.67 (1H, d, J=8.5 Hz), 9.00 (1H, s).

MS (FAB$^+$) m/z: 401 (M+H)$^+$

Example 7

8-{4-[2-(Tetrahydro-2H-pyran-4-yloxy)ethoxy]piperidin-1-yl}-1,6-naphthyridine-2-carboxamide hydrochloride

[Chemical formula 17]

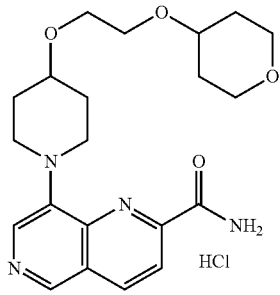

8-{4-[2-(Tetrahydro-2H-pyran-4-yloxy)ethoxy]piperidin-1-yl}-1,6-naphthyridine-2-carboxamide (400 mg, 1.00 mmol) produced in Example 6 was dissolved in ethanol (8 mL), to which a 4M hydrochloric acid/dioxane solution (1.0 mL, 4.0 mmol) was then slowly added, followed by stirring at room temperature for 10 minutes. The resulting reaction liquid was concentrated under reduced pressure, and the residue thus obtained was crystallized from ethanol and diethyl ether to give the desired title compound (368 mg, yield 84%).

$^1$H-NMR (DMSO-D$_6$) δ: 1.32-1.47 (2H, m), 1.74-1.90 (4H, m), 2.04-2.16 (2H, m), 3.26-3.38 (4H, m), 3.47-3.69 (6H, m), 3.76-3.84 (2H, m), 3.85-3.94 (2H, m), 7.90 (1H, br s), 8.11 (1H, s), 8.34 (1H, br s), 8.35 (1H, d, J=8.5 Hz), 8.84 (1H, d, J=8.5 Hz), 9.22 (1H, s).

MS (FAB$^+$) m/z: 401 (M+H)$^+$

Example 8

8-{4-[2-(Dimethylamino)-2-oxoethoxy]piperidin-1-yl}-1,6-naphthyridine-2-carboxamide

[Chemical formula 18]

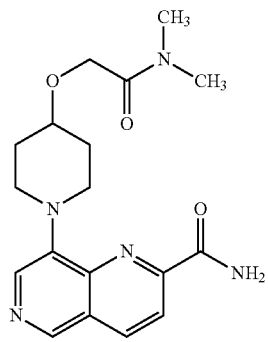

Using 4-[2-(dimethylamino)-2-oxoethoxy]piperidine (5.3 g, 28.4 mmol) and ethyl-8-bromo-1,6-naphthyridine-2-carboxylate (4 g, 14.2 mmol), the desired title compound (1.05 g, yield 21%) was obtained by the same method as in Example 1 (1a) and Example 1 (1b).

$^1$H-NMR (DMSO-D$_6$) δ: 1.75-1.88 (2H, m), 2.06-2.17 (2H, m), 2.83 (3H, s), 2.97 (3H, s), 3.09-3.20 (2H, m), 3.58-3.68 (1H, m), 3.71-3.84 (2H, m), 4.21 (2H, s), 7.81 (1H, br s), 7.99 (1H, br s), 8.23 (1H, d, J=8.5 Hz), 8.32 (1H, s), 8.67 (1H, d, J=8.5 Hz), 9.00 (1H, s).

MS (FAB$^+$) m/z: 358 (M+H)$^+$

Example 9

8-(4-{2-[Methyl(methylsulfonyl)amino]ethoxy}piperidin-1-yl)-1,6-naphthyridine-2-carboxamide

[Chemical formula 19]

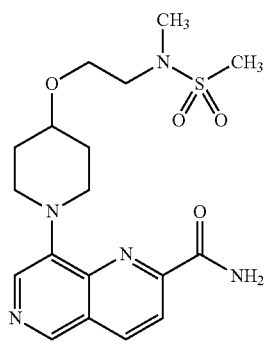

Using 4-{2-[methyl(methylsulfonyl)amino]ethoxy}piperidine (1.0 g, 4.25 mol) and ethyl-8-bromo-1,6-naphthyridine-2-carboxylate (600 mg, 2.14 mmol), the desired title compound (115 mg, yield 13%) was obtained by the same method as in Example 1 (1a) and Example 1 (1b).

$^1$H-NMR (DMSO-D$_6$) δ: 1.74-1.85 (2H, m), 2.05-2.16 (2H, m), 2.85 (3H, s), 2.91 (3H, s), 3.11-3.22 (2H, m), 3.27-3.34 (2H, m), 3.56-3.68 (3H, m), 3.74-3.83 (2H, m), 7.82 (1H, br s), 7.98 (1H, br s), 8.23 (1H, d, J=8.5 Hz), 8.32 (1H, s), 8.67 (1H, d, J=8.5 Hz), 9.00 (1H, s).

MS (FAB$^+$) m/z: 408 (M+H)$^+$

Example 10

8-[4-(Dimethylcarbamoyl)piperazin-1-yl]-1,6-naphthyridine-2-carboxamide

[Chemical formula 20]

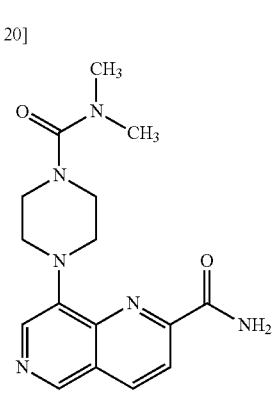

Using 4-(dimethylcarbamoyl)piperazine (560 mg, 3.56 mmol) and ethyl-8-bromo-1,6-naphthyridine-2-carboxylate (500 mg, 1.78 mmol), the desired title compound (97 mg, yield 17%) was obtained by the same method as in Example 1 (1a) and Example 1 (1b).

¹H-NMR (DMSO-D₆) δ: 2.80 (6H, s), 3.39-3.50 (8H, m), 7.83 (1H, br s), 7.96 (1H, br s), 8.25 (1H, d, J=8.5 Hz), 8.32 (1H, s), 8.69 (1H, d, J=8.5 Hz), 9.04 (1H, s).
MS (FAB⁺) m/z: 329 (M+H)⁺

Example 11

8-[3-(Methoxymethyl)piperidin-1-yl]-1,6-naphthyridine-2-carboxamide

[Chemical formula 21]

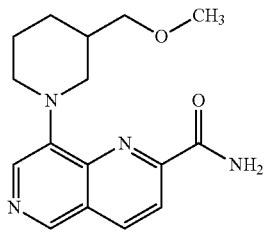

Using 3-(methoxymethyl)piperidine (416 mg, 3.22 mmol) and ethyl-8-bromo-1,6-naphthyridine-2-carboxylate (600 mg, 2.13 mmol), the desired title compound (160 mg, yield 25%) was obtained by the same method as in Example 1 (1a) and Example 1 (1b).
¹H-NMR (DMSO-D₆) δ: 1.08-1.31 (1H, m), 1.72-1.91 (3H, m), 2.15-2.27 (1H, m), 2.64-2.74 (1H, m), 2.91-3.06 (1H, m), 3.27 (3H, s), 3.30-3.38 (2H, m), 3.62-3.72 (1H, m), 4.36-4.46 (1H, m), 7.94 (1H, br s), 8.06 (1H, br s), 8.25 (1H, d, J=8.5 Hz), 8.27 (1H, s), 8.67 (1H, d, J=8.5 Hz), 8.97 (1H, s).
MS (FAB⁺) m/z: 301 (M+H)⁺

Example 12

8-Piperidin-1-yl-1,6-naphthyridine-2-carboxamide (12a) 8-Bromo-1,6-naphthyridine-2-carboxamide

[Chemical formula 22]

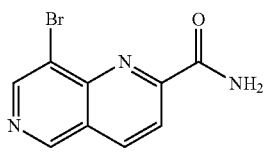

8-Bromo-1,6-naphthyridine-2-carboxylic acid (25.0 g, 98.8 mmol) was suspended in dichloromethane (900 mL), to which 1,1'-carbonyldiimidazole (24.0 g, 148 mmol) was then added. The resulting mixture was stirred for six hours until homogeneous. To the resulting reaction liquid, a 0.5 M ammonia/dioxane solution (988 mL) was added, followed by stirring at room temperature for 12 hours.
The solvent was distilled off under reduced pressure, and water (400 ml) was added. A solid precipitate was collected by filtration. The resulting solid was dried and then suspended in methanol (400 ml) to give a powder. The powder was collected by filtration again, and then dried to give the desired title compound (22.8 g, yield 92%).

¹H-NMR (DMSO-D₆) δ: 8.09 (1H, br s), 8.14 (1H, br s), 8.38 (2H, d, J=8.4 Hz), 8.86 (2H, d, J=8.4 Hz), 9.11 (1H, s), 9.50 (1H, s).
MS (EI⁺) m/z: 251, 253 (M)⁺

(12b)
8-Piperidin-1-yl-1,6-naphthyridine-2-carboxamide

[Chemical formula 23]

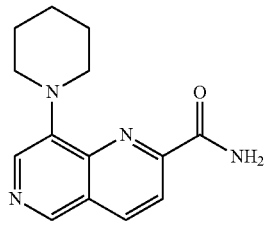

8-Bromo-1,6-naphthyridine-2-carboxamide (22.4 g, 99 mmol) produced in Example 12 (12a) was dissolved in piperidine (152 g, 1.78 mol), to which potassium carbonate (36.9 g, 267 mmol) and tetrabutylammonium iodide (TBAI) (11.8 g, 99 mmol) were then added, followed by stirring at 110° C. for four hours. Piperidine was distilled off under reduced pressure. Toluene and water were added to the residue thus obtained, and the resulting mixture was partitioned (the pH of the aqueous layer was adjusted to be weakly basic). The aqueous layer was extracted with dichloromethane again, and then combined with the toluene layer. The resulting mixture was dried over anhydrous sodium sulfate and the solvent was distilled off under reduced pressure. The residue thus obtained was sequentially purified by normal phase silica gel column chromatography ((after letting hexane:ethyl acetate, 50:50, flow through, applying ethyl acetate:methanol, 100:0-90:10, V/V), basic silica gel column chromatography (hexane:ethyl acetate, 100:0-0:100, V/V), and reverse phase silica gel column chromatography (water:acetonitrile, 90:10-60:40, V/V) to give the desired title compound (15.7 g, yield 69%).
¹H-NMR (DMSO-D₆) δ: 1.60-1.69 (2H, m), 1.76-1.85 (4H, m), 3.37-3.45 (4H, m), 7.80 (1H, br s), 8.03 (1H, br s), 8.23 (1H, d, J=8.5 Hz), 8.29 (1H, s), 8.67 (1H, d, J=8.5 Hz), 8.99 (1H, s).
MS (EI⁺) m/z: 256 (M)⁺.

Example 13

8-Morpholin-4-yl-1,6-naphthyridine-2-carboxamide

[Chemical formula 24]

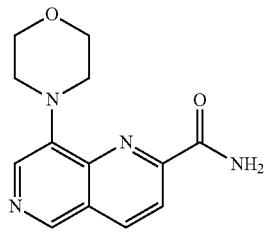 [SMILES: NC(=O)c1ccc2cncc(N3CCOCC3)c2c1]

Using 8-bromo-1,6-naphthyridine-2-carboxamide (2.02 g, 8.0 mmol) produced in Example 12 (12a), the desired title compound (1.10 g, yield 53%) was obtained by the same method as in Example 12 (12b).

$^1$H-NMR (DMSO-D$_6$) δ: 3.43-3.49 (4H, m), 3.88-3.93 (4H, m), 7.82 (1H, br s), 7.96 (1H, br s), 8.25 (1H, d, J=8.4 Hz), 8.31 (1H, s), 8.69 (1H, d, J=8.4 Hz), 9.05 (1H, s).

MS (FAB$^+$) m/z 259 (M+H)$^+$

Example 14

8-(Azepan-1-yl)-1,6-naphthyridine-2-carboxamide

[Chemical formula 25]

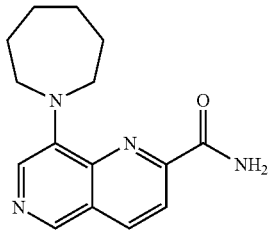

Using 8-bromo-1,6-naphthyridine-2-carboxamide (201 mg, 0.8 mmol) produced in Example 12 (12a), the desired title compound (55 mg, yield 26%) was obtained by the same method as in Example 12 (12b).

$^1$H-NMR (DMSO-D$_6$) δ: 1.53-1.66 (4H, m), 1.83-1.96 (4H, m), 3.80 (4H, t, J=5.7 Hz), 7.64 (1H, br s), 7.96 (1H, br s), 8.15 (1H, d, J=8.6 Hz), 8.19 (1H, s), 8.55 (1H, d, J=8.6 Hz), 8.69 (1H, s).

MS (FAB$^+$) m/z 259 (M+H)$^+$

Example 15

4-(4-Phenylpiperazin-1-yl)isoquinoline-6-carboxamide (15a) 6-Bromo-4-hydroxyisoquinoline

[Chemical formula 26]

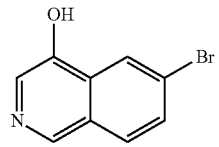

6-Bromo-2-(phenylsulfonyl)-2,3-dihydroisoquinoline-4(1H)-one (29 g, 79.2 mmol) was produced from 4-bromobenzyl bromide in accordance with the method described in Tetrahedron 61 (2005) 8282 to 8287, and then suspended in ethanol (300 ml). To the resulting mixture, a 21% sodium ethoxide/ethanol solution (88.6 ml, 238 mmol) was added, followed by stirring at room temperature for one hour. To the resulting reaction liquid, 5M hydrochloric acid (approximately 50 ml) was added for neutralization, and then ethanol was distilled off under reduced pressure. A solid precipitate was collected by filtration. The solid was dried and then purified by silica gel column chromatography (dichloromethane:methanol, 100:0-50:50, V/V) to give the desired title compound (13.2 g, yield 75%).

$^1$H-NMR (DMSO-D$_6$) δ: 7.79 (1H, dd, J=8.7, 1.8 Hz), 8.03 (1H, d, J=8.7 Hz), 8.11 (1H, s), 8.25-8.27 (1H, m), 8.82 (1H, s), 10.62 (1H, s).

(15b) 2-(Trimethylsilyl)ethyl 4-hydroxyisoquinoline-6-carboxylate

[Chemical formula 27]

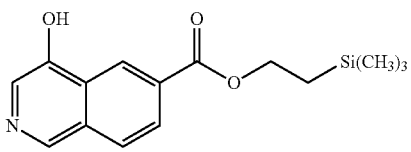

6-Bromo-4-hydroxyisoquinoline (15.7 g, 70.0 mmol) produced in Example 15 (15a) was dissolved in dimethylformamide (100 mL), to which 2-trimethylsilylethanol (100 mL), diisopropylethylamine (27.1 g, 210 mmol), 1,3-bis(diphenylphosphino)propane (8.67 g, 21.0 mmol), and palladium chloride (3.72 g, 21.0 mmol) were then added, followed by stirring at 60° C. for eight hours under a carbon monoxide atmosphere. The solvent was distilled off under reduced pressure. Water was added to the residue thus obtained, and the resulting mixture was extracted with dichloromethane. The resulting organic layer was dried over anhydrous sodium sulfate and the solvent was distilled off under reduced pressure. The residue thus obtained was purified by silica gel column chromatography ((a mixed solvent of hexane:ethyl acetate-1:1):methanol, 100:0-70:30, V/V) to give the desired title compound (17.3 g, yield 85.4%).

$^1$H-NMR (CDCl$_3$) δ: 0.11 (9H, s), 1.11-1.24 (2H, m), 4.46-4.55 (2H, m), 8.02 (1H, d, J=8.4 Hz), 8.24 (1H, d, J=8.4 Hz), 8.38 (1H, s), 8.87 (1H, s), 9.09 (1H, s).

(15c) 2-(Trimethylsilyl)ethyl 4-{[(trifluoromethyl)sulfonyl]oxy}isoquinoline-6-carboxylate

[Chemical formula 28]

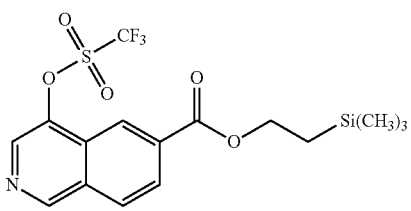

2-(Trimethylsilyl)ethyl 4-hydroxyisoquinoline-6-carboxylate (15.0 g, 51.8 mmol) produced in Example 15 (15b) was dissolved in dichloromethane (300 mL), to which pyridine (10.2 g, 130 mmol) was then added. The resulting reaction liquid was cooled to −25° C., to which trifluoromethanesulfonic anhydride (16.8 g, 59.6 mmol) was added. The mixture was warmed to room temperature over one hour while stirring. The resulting reaction liquid was washed with a saturated aqueous solution of sodium bicarbonate and saturated brine, and then dried over anhydrous sodium sulfate. The solvent was distilled off under reduced pressure. The residue thus obtained was purified by silica gel column chromatography (hexane:ethyl acetate, 100:0-75:25, V/V) to give the desired title compound (17.0 g, yield 78%).

$^1$H-NMR (CDCl$_3$) δ: 0.12 (9H, s), 1.16-1.28 (2H, m), 4.48-4.63 (2H, m), 8.17 (1H, d, J=8.6 Hz), 8.35 (1H, d, J=8.6 Hz), 8.66 (1H, s), 8.79 (1H, s), 9.35 (1H, s).

(15d) 2-(Trimethylsilyl)ethyl 4-(4-phenylpiperazin-1-yl) isoquinoline-6-carboxylate

[Chemical formula 29]

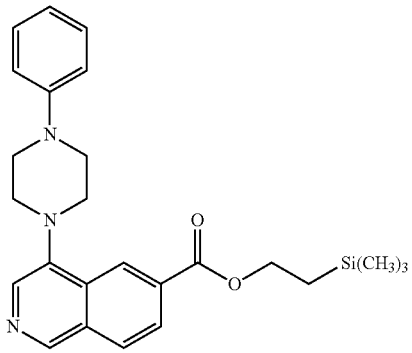

4-Phenylpiperazine (1.90 mL, 12.5 mmol) was dissolved in toluene (8.5 mL), to which 2-(trimethylsilyl)ethyl 4-{[(trifluoromethyl)sulfonyl]oxy}isoquinoline-6-carboxylate (3.50 g, 8.30 mmol) produced in Example 15 (15c), tris(dibenzylideneacetone)dipalladium (760 mg, 0.83 mmol), 2-dicyclohexylphosphino-2'-(N,N-dimethylamino)biphenyl (654 mg, 1.66 mmol), and potassium carbonate (3.44 g, 24.9 mmol) were then added. The resulting mixture was heated under reflux for 1.5 hours under a nitrogen atmosphere. After cooling, the reaction liquid was filtered and the solvent was distilled off. The residue thus obtained was sequentially purified by basic silica gel column chromatography (hexane:ethyl acetate, 100:0-50:50, V/V) and normal phase silica gel column chromatography (hexane:ethyl acetate, 80:20-20:80, V/V) to give the desired title compound (2.37 g, yield 66%).

$^1$H-NMR (CDCl$_3$) δ: 0.11 (9H, s), 1.16-1.21 (2H, m), 3.36-3.41 (4H, m), 3.49-3.54 (4H, m), 4.49-4.53 (2H, m), 6.93 (1H, t, J=7.2 Hz), 7.05 (2H, d, J=8.2 Hz), 7.33 (2H, dd, J=8.2, 7.2 Hz), 8.03 (1H, d, J=8.4 Hz), 8.19 (1H, d, J=8.4 Hz), 8.32 (1H, s), 8.89 (1H, s), 9.05 (1H, s).

MS (ESI$^+$) m/z: 434 (M+H)$^+$

(15e) 4-(4-Phenylpiperazin-1-yl)isoquinoline-6-carboxamide

[Chemical formula 30]

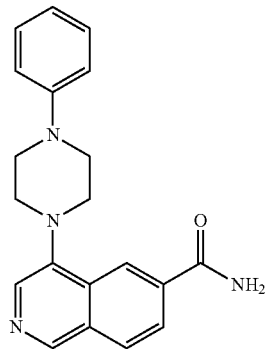

2-(Trimethylsilyl)ethyl 4-(4-phenylpiperazin-1-yl)isoquinoline-6-carboxylate (2.37 g, 5.47 mmol) produced in Example 3 (3d) was dissolved in tetrahydrofuran (27 mL), to which a 1.0M n-tetrabutylammonium fluoride/tetrahydrofuran solution (16.4 mL, 16.4 mmol) was then added, followed by stirring at room temperature for 1.5 hours. The solvent was distilled off under reduced pressure. The residue thus obtained was dissolved in N,N-dimethylformamide (47 mL) under a nitrogen atmosphere, to which ammonium chloride (2.92 g, 54.7 mol), triethylamine (9.14 mL, 65.6 mmol), 1-hydroxybenzotriazole (251 mg, 1.64 mmol), and N-[3-dimethylaminopropyl]-N'-ethylcarbodiimide hydrochloride (5.24 g, 27.3 mmol) were added, followed by stirring at room temperature for 13 hours. The resulting reaction liquid was filtered and the solvent was distilled off under reduced pressure. The residue thus obtained was purified by basic silica gel column chromatography (hexane:ethyl acetate, 50:50-0:100, V/V) and recrystallized from a mixed solvent of ethanol-dichloromethane to give the desired title compound (1.13 g, yield 62%).

$^1$H-NMR (DMSO-D$_6$) δ: 3.28-3.32 (4H, m), 3.44-3.48 (4H, m), 6.84 (1H, t, J=7.2 Hz), 7.06 (2H, d, J=8.3 Hz), 7.27 (2H, dd, J=8.3, 7.2 Hz), 7.65 (1H, br s), 8.08 (1H, d, J=8.2 Hz), 8.19 (1H, d, J=8.2 Hz), 8.31 (1H, s), 8.33 (1H, br s), 8.58 (1H, s), 9.10 (1H, s).

MS (FAB$^+$) m/z: 333 (M+H)$^+$

Example 16

4-(Piperidin-1-yl)isoquinoline-6-carboxamide

[Chemical formula 31]

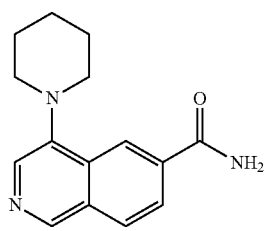

Using piperidine (2.4 ml, 24 mmol) and 2-(trimethylsilyl)ethyl 4-{[trifluoromethyl)sulfonyl]oxy}isoquinoline-6-carboxylate (5 g, 12 mmol) produced in Example 15 (15c), the desired title compound (1.18 g, yield 39%) was obtained by the same method as in Example 15 (15d) and Example 15 (15e).

$^1$H-NMR (DMSO-D$_6$) δ: 1.61-1.68 (2H, m), 1.79-1.84 (4H, m), 3.06-3.12 (4H, m), 7.60 (1H, br s), 8.04 (1H, d, J=8.5 Hz), 8.14 (1H, d, J=8.5 Hz), 8.21 (1H, s), 8.28 (1H, br s), 8.51 (1H, s), 9.02 (1H, s).

MS (EI$^+$) m/z: 255 (M$^+$)

Example 17

4-[3-(Methoxymethyl)piperidin-1-yl]isoquinoline-6-carboxamide

[Chemical formula 32]

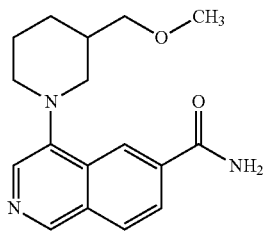 [SMILES: CCOC1CCCN(c2cncc3ccc(C(N)=O)cc23)C1]

Using 3-(methoxymethyl)piperidine (185 mg, 1.43 mmol) and 2-(trimethylsilyl)ethyl 4-{[(trifluoromethyl)sulfonyl]oxy}isoquinoline-6-carboxylate (300 mg, 0.71 mmol) produced in Example 15 (15c), the desired title compound (57 mg, yield 27%) was obtained by the same method as in Examples 15 (15d) and 15 (15e).

$^1$H-NMR (DMSO-D$_6$) δ: 1.15-1.29 (1H, m), 1.76-1.91 (3H, m), 2.13-2.25 (1H, m), 2.60-2.70 (1H, m), 2.79-2.88 (1H, m), 3.25 (3H, s), 3.27-3.39 (4H, m), 7.61 (1H, br s), 8.05 (1H, d, J=8.5 Hz), 8.15 (1H, d, J=8.5 Hz), 8.21 (1H, s), 8.25 (1H, br s), 8.51 (1H, s), 9.03 (1H, s).

MS (EI$^+$) m/z 299 (M$^+$)

Example 18

4-[4-(1,3-Thiazol-2-yl)piperazin-1-yl]isoquinoline-6-carboxamide

[Chemical formula 33]

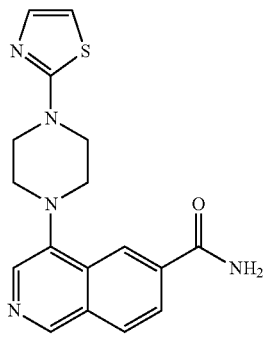

Using (1,3-thiazol-2-yl)piperazine (241 mg, 1.42 mmol) and 2-(trimethylsilyl)ethyl 4-{[(trifluoromethyl)sulfonyl]oxy}isoquinoline-6-carboxylate (400 mg, 0.949 mmol) produced in Example 15 (15c), the desired title compound (127 mg, yield 41%) was obtained by the same method as in Examples 15 (15d) and 15 (15e).

$^1$H-NMR (DMSO-D$_6$) δ: 3.25-3.31 (4H, m), 3.69-3.75 (4H, m), 6.92 (1H, d, J=3.4 Hz), 7.24 (1H, d, J=3.4 Hz), 7.67 (1H, br s), 8.09 (1H, d, J=8.7 Hz), 8.19 (1H, d, J=8.7 Hz), 8.30 (1H, s), 8.35 (1H, br s), 8.56 (1H, s), 9.11 (1H, s).

MS (FAB$^+$) m/z: 340 (M+H)$^+$

Example 19

4-{4-[2-(Tetrahydro-2H-pyran-2-yloxy)ethoxy]piperidin-1-yl}isoquinoline-6-carboxamide

[Chemical formula 34]

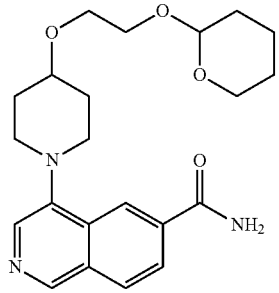

Using 4-[2-(tetrahydro-2H-pyran-2-yloxy)ethoxy]piperidine (545 mg, 2.38 mmol) and 2-(trimethylsilyl)ethyl 4-{[trifluoromethyl)sulfonyl]oxy}isoquinoline-6-carboxylate (668 mg, 1.59 mmol) produced in Example 15 (15c), the desired title compound (330 mg, yield 61%) was obtained by the same method as in Examples 15 (15d) and 15 (15e).

$^1$H-NMR (DMSO-D$_6$) δ: 1.42-1.53 (4H, m), 1.59-1.68 (1H, m), 1.70-1.89 (3H, m), 2.05-2.14 (2H, m), 2.90-2.99 (2H, m), 3.36-3.41 (2H, m), 3.42-3.48 (1H, m), 3.51-3.66 (4H, m), 3.72-3.84 (2H, m), 4.62-4.65 (1H, m), 7.64 (1H, br s), 8.06 (1H, d, J=8.4 Hz), 8.15 (1H, d, J=8.4 Hz), 8.22 (1H, s), 8.33 (1H, br s), 8.51 (1H, s), 9.04 (1H, s)

MS (FAB$^+$) m/z: 400 (M+H)$^+$

Example 20

4-[4-(2-Hydroxyethoxy)piperidin-1-yl]isoquinoline-6-carboxamide

[Chemical formula 35]

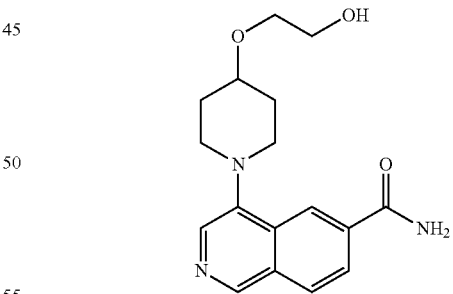

4-{4-[2-(Tetrahydro-2H-pyran-2-yloxy)ethoxy]piperidin-1-yl}isoquinoline-6-carboxamide (330 mg, 0.83 mmol) produced in Example 19 was dissolved in methanol-water (90:10, V/V, 15 mL), to which p-toluenesulfonic acid monohydrate (213 mg, 1.24 mmol) was then added, followed by stirring at room temperature for 24 hours. After addition of triethylamine (300 μL), the solvent was distilled off under reduced pressure. The residue thus obtained was purified by basic silica gel column chromatography (ethyl acetate:methanol, 100:0-80:20, V/V) to give the desired title compound (160 mg, yield 61%).

$^1$H-NMR (DMSO-D$_6$) δ: 1.76-1.86 (2H, m), 2.06-2.14 (2H, m), 2.91-2.98 (2H, m), 3.29-3.36 (2H, m), 3.50-3.61 (5H, m), 4.58-4.61 (1H, m), 7.63 (1H, br s), 8.05 (1H, d, J=8.5 Hz), 8.15 (1H, d, J=8.5 Hz), 8.23 (1H, s), 8.31 (1H, br s), 8.50 (1H, s), 9.03 (1H, s).
MS (FAB$^+$) m/z: 316 (M+H)$^+$.

Example 21

Tert-butyl (2-{[1-(6-carbamoylisoquinolin-4-yl)piperidin-3-yl]methoxy}ethyl)carbamate

[Chemical formula 36]

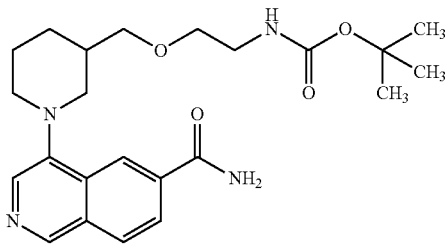

Using tert-butyl[2-(piperidin-3-ylethoxy)ethyl]carbamate (572 mg, 2.21 mmol) and 2-(trimethylsilyl)ethyl 4-{[(trifluoromethyl)sulfonyl]oxy}isoquinoline-6-carboxylate (733 mg, 1.74 mmol) produced in Example 15 (15c), the desired title compound (497 mg, yield 54%) was obtained by the same method as in Examples 15 (15d) and 15 (15e).

$^1$H-NMR (CDCl$_3$) δ: 1.37 (11H, s), 1.79-1.94 (2H, m), 2.21-2.34 (1H, m), 2.87 (1H, br s), 2.97-3.07 (1H, m), 3.20-3.41 (4H, m), 3.43-3.51 (2H, m), 3.53-3.61 (1H, m), 3.73 (1H, br s), 4.84 (1H, br s), 5.90 (1H, br s), 6.86 (1H, br s), 7.95-8.08 (2H, m), 8.24 (1H, s), 8.53 (1H, s), 8.99 (1H, s).
MS (EI$^+$) m/z: 429 (M+H)$^+$

Example 22

4-{3-[(2-Aminoethoxy)methyl]piperidin-1-yl}isoquinoline-6-carboxamide hydrochloride

[Chemical formula 37]

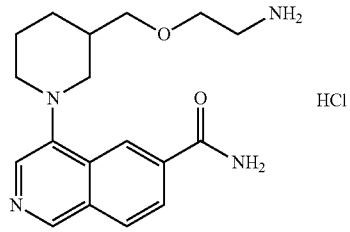

Tert-butyl (2-{[1-(6-carbamoylisoquinolin-4-yl)piperidin-3-yl]methoxy}ethyl)carbamate (158 mg, 0.368 mmol) produced in Example 21 was dissolved in dioxane (5 mL), to which a 4M hydrochloric acid/dioxane solution (2 mL) was added, followed by stirring overnight at room temperature. Upon completion of the reaction, the solvent was distilled off under reduced pressure to give the desired title compound (148 mg, yield 100%).

$^1$H-NMR (DMSO-D$_6$) δ: 1.19-1.38 (1H, m), 1.78-1.96 (2H, m), 2.13-2.29 (1H, m), 2.75-3.05 (4H, m), 3.44-3.67 (8H, m), 7.89 (1H, s), 7.98 (2H, s), 8.24-8.33 (1H, m), 8.46-8.64 (2H, m), 9.48 (1H, s).
MS (EI$^+$) m/z: 329 (M+H)$^+$

Example 23

4-(4-Hydroxy-4-phenylpiperidin-1-yl)isoquinoline-6-carboxamide

[Chemical formula 38]

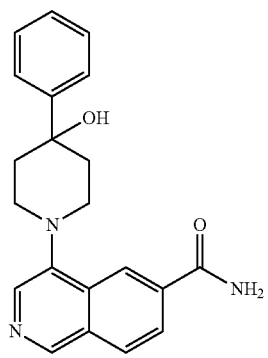

Using 4-hydroxy-4-phenylpiperidine (193 mg, 1.09 mmol) and 2-(trimethylsilyl)ethyl 4-{[(trifluoromethyl)sulfonyl]oxy}isoquinoline-6-carboxylate (314 mg, 0.746 mmol) produced in Example 15 (15c), the desired title compound (200 mg, yield 60%) was obtained by the same method as in Examples 15 (15d) and 15 (15e).

$^1$H-NMR (DMSO-D$_6$) δ: 1.79-1.87 (2H, m), 2.30-2.41 (2H, m), 3.24-3.38 (4H, m), 5.07 (1H, s), 7.26 (1H, t, J=7.3 Hz), 7.39 (2H, dd, J=7.7, 7.3 Hz), 7.62 (1H, br s), 7.63 (2H, d, J=7.7 Hz), 8.07 (1H, d, J=8.5 Hz), 8.16 (1H, d, J=8.5 Hz), 8.30 (1H, s), 8.32 (1H, br s), 8.57 (1H, s), 9.04 (1H, s).
MS (EI$^+$) m/z: 348 (M+H)$^+$

Example 24

4-(4-Phenyl-3,6-dihydropyridine-1(2H)-yl)isoquinoline-6-carboxamide

[Chemical formula 39]

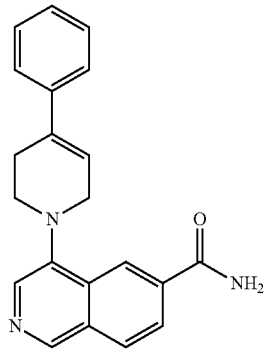

4-(4-Hydroxy-4-phenylpiperidin-1-yl)isoquinoline-6-carboxamide (134 mg, 0.386 mmol) produced in Example 23 was dissolved in trifluoroacetic acid (1 mL)/dichloromethane (1.5 mL), and the resulting mixture was heated to reflux overnight. Upon completion of the reaction, the solvent was distilled off under reduced pressure. The residue thus obtained was purified by silica gel column chromatography (hexane:ethyl acetate, 50:50-0:100, V/V) to give the desired title compound (108 mg, yield 85%).

$^1$H-NMR (DMSO-D$_6$) δ: 2.74-2.84 (2H, m), 3.35-3.54 (2H, m), 3.88-3.98 (2H, m), 6.42 (1H, m), 7.30 (1H, t, J=7.3 Hz), 7.40 (2H, dd, J=7.7, 7.3 Hz), 7.56 (2H, d, J=7.7 Hz), 7.62 (1H, s), 8.08 (1H, d, J=8.5 Hz), 8.18 (1H, d, J=8.5 Hz), 8.33 (1H, s), 8.34 (1H, s), 8.57 (1H, s), 9.07 (1H, s).

MS (EI$^+$) m/z: 330 (M+H)$^+$

Reference Example 1

4-[2-(Tetrahydro-2H-pyran-4-yloxy)ethoxy]piperidine (1a) Benzyl 4-[2-(tetrahydro-2H-pyran-2-yloxy)ethoxy]piperidine-1-carboxylate

[Chemical formula 40]

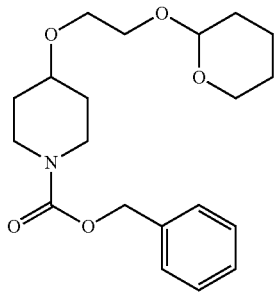

2-(Tetrahydro-2H-pyran-2-yloxy)ethyl 4-methylbenzylsulfonate (49.8 g, 166 mmol) was dissolved in N,N-dimethylformamide (500 mL), to which benzyl 4-hydroxy-1-piperidinecarboxylate (31.1 g, 132 mmol) was then added. Further, sodium hydride (content 55%) (7.23 g, 166 mmol) was added at once, followed by stirring at room temperature for two hours under a nitrogen atmosphere.

To the resulting reaction liquid, dichloromethane and water were added, and the resulting mixture was extracted with dichloromethane. The resulting organic layer was dried over sodium sulfate and the solvent was distilled off under reduced pressure. The residue thus obtained was purified by silica gel column chromatography (hexane:ethyl acetate, 100:0-50:50, V/V) to give the desired title compound (45.6 g, yield 95%).

$^1$H-NMR (CDCl$_3$) δ: 1.49-1.62 (6H, m), 1.69-1.75 (1H, m), 1.78-1.88 (3H, m), 3.20-3.25 (2H, m), 3.45-3.66 (5H, m), 3.74-3.90 (4H, m), 4.64 (1H, t, J=3.7 Hz), 5.12 (2H, s), 7.29-7.38 (5H, m).

(1b) Benzyl 4-(2-hydroxyethoxy)piperidine-1-carboxylate

[Chemical formula 41]

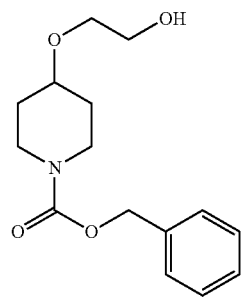

Benzyl 4-[2-(tetrahydro-2H-pyran-2-yloxy)ethoxy]piperidine-1-carboxylate (45.6 g, 125 mmol) produced in Reference Example 1 (1a) was dissolved in methanol, to which p-toluenesulfonic acid monohydrate (11.9 g, 62.7 mmol) was added, followed by stirring at room temperature for 2.5 hours.

To the resulting reaction liquid, sodium bicarbonate (powder) was added, and the solvent was distilled off under reduced pressure. A solid precipitate was filtered off while washing with ethyl acetate. The filtrate was concentrated under reduced pressure. The residue thus obtained was purified by silica gel column chromatography (hexane:ethyl acetate, 60:40-0:100, V/V) to give the desired title compound (29.1 g, yield 83%).

$^1$H-NMR (CDCl$_3$) δ: 1.52-1.60 (2H, m), 1.82-1.90 (2H, m), 1.98 (1H, t, J=6.0 Hz), 3.18-3.24 (2H, m), 3.50-3.55 (1H, m), 3.58 (3H, t, J=4.6 Hz), 3.73 (2H, dt, J=6.0, 4.6 Hz), 3.79-3.86 (2H, m), 5.13 (2H, s), 7.29-7.38 (5H, m).

(1c) Benzyl 4-(2-{[(4-methylphenyl)sulfonyl]oxy}ethoxy)piperidine-1-carboxylate

[Chemical formula 42]

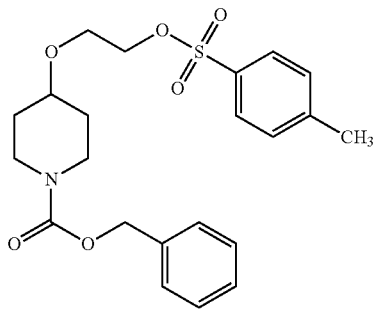

Benzyl 4-(2-hydroxyethoxy)piperidine-1-carboxylate (20.0 g, 71.6 mmol) produced in Reference Example 1 (1b) was dissolved in dichloromethane (360 mL), to which N,N-dimethylaminopyridine (875 mg, 7.16 mmol) and triethylamine (20.0 mL, 143 mmol) were added. Further, p-toluenesulfonyl chloride (17.7 g, 93.1 mmol) was slowly added, followed by stirring at room temperature for 2.5 hours.

To the resulting reaction liquid, water was added, and the resulting mixture was extracted with dichloromethane. The resulting organic layer was dried over magnesium sulfate and the solvent was distilled off under reduced pressure. The residue thus obtained was purified by silica gel column chromatography (hexane:ethyl acetate, 100:0-50:50, V/V) to give the desired title compound (30.7 g, yield 99%).

$^1$H-NMR (CDCl$_3$) δ: 1.44-1.51 (2H, m), 1.70-1.77 (2H, m), 2.44 (3H, s), 3.19-3.24 (2H, m), 3.44-3.48 (1H, m), 3.65 (2H, t, J=4.7 Hz), 3.66-3.70 (2H, m), 4.15 (2H, t, J=4.7 Hz), 5.12 (2H, s), 7.30-7.38 (7H, m), 7.79 (2H, d, J=8.6 Hz).

(1d) 4-[2-(Tetrahydro-2H-pyran-4-yloxy)ethoxy]piperidine-1-carboxylate

[Chemical formula 43]

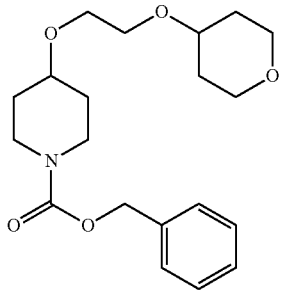

Benzyl 4-(2-{[(4-methylphenyl)sulfony]oxy}ethoxy)piperidine-1-carboxylate (1.64 g, 3.79 mmol) produced in Reference Example 1 (1c) was dissolved in N,N-dimethylformamide (10 mL), to which tetrahydro-2H-pyran-4-ol (540 μL, 5.69 mmol) and sodium hydride (content 55%) (248 mg, 5.69 mmol) were added, followed by stirring at room temperature for 20 hours. Water was added to the resulting reaction liquid, followed by extraction with ethyl acetate. The resulting organic layer was washed with water and saturated brine, and dried over anhydrous sodium sulfate. The solvent was distilled off under reduced pressure. The residue thus obtained was purified by silica gel column chromatography (ethyl acetate:hexane, 0:100-40:60, V/V) to give the desired title compound (510 mg, yield 37%).

$^1$H-NMR (CDCl$_3$) δ: 1.58-1.60 (4H, m), 1.86-1.89 (4H, m), 3.20-3.23 (2H, m), 3.40-3.46 (2H, m), 3.51-3.53 (2H, m), 3.60-3.63 (4H, m), 3.80-3.82 (2H, m), 3.92-3.94 (2H, m), 5.12 (2H, s), 7.34-7.35 (5H, m).

MS (FAB) m/z: 364 (M+H)$^+$ (1e) 4-[2-(Tetrahydro-2H-pyran-4-yloxy)ethoxy]piperidine

[Chemical formula 44]

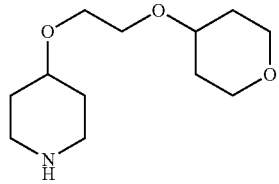

Benzyl 4-[2-(tetrahydro-2H-pyran-4-yloxy)ethoxy]piperidine-1-carboxylate (505 mg, 1.39 mmol) produced in Reference Example 1 (1e) was dissolved in methanol (15 mL), to which palladium hydroxide (50 mg) was added, followed by stirring at room temperature for 18 hours under a hydrogen atmosphere. The resulting reaction liquid was filtered through Celite, and the solvent was distilled off under reduced pressure to give the desired title compound (318 mg, yield 100%).

$^1$H-NMR (CDCl$_3$) δ: 1.43-1.52 (2H, m), 1.58-1.61 (2H, m), 1.85-1.96 (4H, m), 2.61-2.67 (2H, m), 3.09-3.11 (2H, m), 3.40-3.46 (3H, m), 3.50-3.57 (1H, m), 3.61-3.62 (4H, m), 3.93-3.96 (2H, m).

MS (FAB) m/z: 230 (M+H)$^+$

Reference Example 2

4-{2-[(3R)-Tetrahydrofuran-3-yloxy]ethoxy}piperidine

[Chemical formula 45]

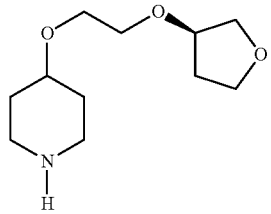

Using benzyl 4-(2-{[(4-methylphenyl)sulfony]oxy}ethoxy)piperidine-1-carboxylate (4.00 g, 9.23 mmol) produced in Reference Example 1 (1c) and (3R)-tetrahydrofuran-3-ol (1.05 g, 12.0 mmol), the desired title compound (1.56 g, yield 79%) was obtained by the same method as in Reference Examples 1 (1d) and 1 (1e).

$^1$H-NMR (CDCl$_3$) δ: 1.39-1.46 (2H, m), 1.90-1.95 (2H, m), 1.97-2.01 (2H, m), 2.57-2.62 (2H, m), 3.06-3.10 (2H, m), 3.36-3.42 (1H, m), 3.54-3.63 (4H, m), 3.77-3.84 (3H, m), 3.90 (1H, q, J=7.8 Hz), 4.16-4.19 (1H, m).

MS (FAB) m/z: 216 (M+H)$^+$

Reference Example 3

4-{2-[(3S)-Tetrahydrofuran-3-yloxy]ethoxy}piperidine

[Chemical formula 46]

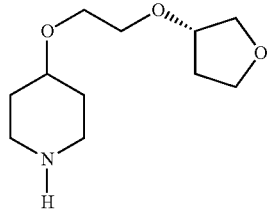

Using benzyl 4-(2-{[(4-methylphenyl)sulfony]oxy}ethoxy)piperidine-1-carboxylate (4.00 g, 9.23 mmol) produced in Reference Example 1 (1c) and (3S)-tetrahydrofuran-3-ol (1.05 g, 12.0 mmol), the desired title compound (1.52 g, yield 77%) was obtained by the same method as in Reference Examples 1 (1d) and 1 (1e).

$^1$H-NMR (CDCl$_3$) δ: 1.39-1.46 (2H, m), 1.90-1.95 (2H, m), 1.97-2.01 (2H, m), 2.57-2.62 (2H, m), 3.06-3.10 (2H, m), 3.36-3.42 (1H, m), 3.55-3.63 (4H, m), 3.77-3.84 (3H, m), 3.90 (1H, q, J=7.8 Hz), 4.16-4.19 (1H, m).
MS (FAB) m/z: 216 (M+H)$^+$

Reference Example 4

4-[2-(Tetrahydrofuran-3-ylmethoxy)ethoxy]piperidine

[Chemical formula 47]

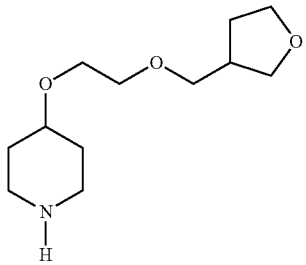

Using benzyl 4-(2-{[(4-methylphenyl)sulfonyl]oxy}ethoxy)piperidine-1-carboxylate (4.00 g, 9.23 mmol) produced in Reference Example 1 (1c) and (tetrahydrofuran-3-yl)methanol (1.23 g, 12.0 mmol), the desired title compound (1.41 g, yield 67%) was obtained by the same method as in Examples 1 (1d) and 1 (1e).
$^1$H-NMR (CDCl$_3$) δ: 1.42-1.49 (2H, m), 1.57-1.63 (1H, m), 1.90-1.96 (2H, m), 1.97-2.04 (1H, m), 2.50-2.58 (1H, m), 2.59-2.65 (2H, m), 3.07-3.12 (2H, m), 3.37-3.42 (2H, m), 3.43-3.49 (1H, m), 3.57-3.63 (5H, m), 3.70-3.75 (1H, m), 3.81-3.85 (2H, m).
MS (FAB) m/z: 230 (M+H)$^+$ Reference Example 5

4-{2-[(Dimethylamino)sulfonyl]ethoxy}piperidine (5a) benzyl 4-{2-[(Dimethylamino)sulfonyl]ethoxy}piperidine-1-carboxylate

[Chemical formula 48]

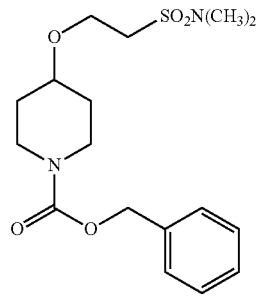

Benzyl 4-hydroxypiperidine-1-carboxylate (5.0 g, 21.2 mmol) was dissolved in tetrahydrofuran (100 ml), and while cooling with ice, sodium hydride (content 55%) (1.0 g, 22.9 mmol) was added. The resulting mixture was stirred for 30 minutes while cooling with ice, to which 20 mL of a solution of N,N-dimethylethenesulfonamide in tetrahydrofuran (3.0 g, 22.2 mmol) was added dropwise over five minutes. The resulting mixture was stirred for 30 minutes while cooling with ice, and then for three hours at room temperature. The resulting reaction liquid was poured into water and then extracted with ethyl acetate. The resulting organic layer was sequentially washed with water and saturated brine, and then dried over sodium sulfate. The solvent was distilled off under reduced pressure. The residue thus obtained was purified by silica gel column chromatography (hexane:ethyl acetate, 50:50-0:100, V/V) to give the desired title compound (4.9 g, yield 62%).
$^1$H-NMR (CDCl$_3$) δ: 1.48-1.61 (2H, m), 1.82-1.92 (2H, m), 3.14-3.25 (4H, m), 3.49-3.58 (1H, m), 3.79-3.89 (4H, m), 5.12 (2H, s), 7.28-7.42 (5H, m).

(5b) 4-{2-[(Dimethylamino)sulfonyl]ethoxy}piperidine

[Chemical formula 49]

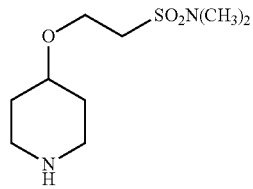

Using benzyl 4-{2-[(dimethylamino)sulfonyl]ethoxy}piperidine-1-carboxylate (4.9 g, 13.2 mmol) produced in Reference Example 5 (5a), the desired title compound (3.1 g, yield 99%) was obtained by the same method as in Reference Example 1 (1e).
$^1$H-NMR (CDCl$_3$) δ: 1.37-1.50 (2H, m), 1.90-2.00 (2H, m), 2.56-2.66 (2H, m), 2.88 (6H, s), 3.04-3.14 (2H, m), 3.22 (2H, t, J=6.2 Hz), 3.37-3.46 (1H, m), 3.84 (2H, t, J=6.2 Hz).

Reference Example 6

3-[(Difluoromethoxy)methyl]piperidine (6a) Benzyl 3-[(difluoromethoxy)methyl]piperidine-1-carboxylate

[Chemical formula 50]

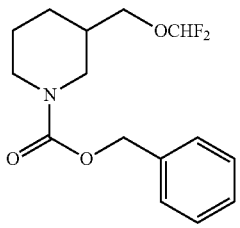

Benzyl 3-(hydroxymethyl)piperidine-1-carboxylate (2.49 g, 10.0 mmol) was dissolved in acetonitrile (100 mL), to which copper iodide (I) (2.86 g, 15.0 mmol) and 2,2-difluoro-2-(fluorosulfonyl)acetic acid (2.66 g, 15.0 mmol) were added, followed by stirring at 80° C. for 20 minutes. The mixture was brought down to room temperature, to which adequate amounts of hexane and ethyl acetate were added, followed by neutralization with a 2M ammonia/methanol solution. Impurities were filtered off, and the solvent was distilled off under reduced pressure. The residue thus obtained was purified by basic silica gel column chromatography (hexane:ethyl acetate, 100:0-0:100, V/V) to give the desired title compound (1.82 g, yield 61%).

$^1$H-NMR (CDCl$_3$) δ: 1.22-1.34 (1H, m), 1.41-1.55 (1H, m), 1.64-1.73 (1H, m), 1.76-1.92 (2H, m), 2.59-2.97 (2H, m), 3.64-3.77 (2H, m), 3.93-4.21 (2H, m), 5.13 (2H, s), 6.18 (1H, t, J=74.5 Hz), 7.28-7.41 (5H, m).

(6b) 3-[(Difluoromethoxy)methyl]piperidine

[Chemical formula 51]

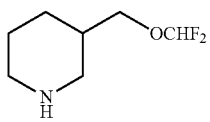

Using benzyl 3-[(difluoromethoxy)methyl]piperidine-1-carboxylate (1.97 g, 6.58 mmol) produced in Reference Example 6 (6a), the desired title compound (1.00 g, yield 92%) was obtained by the same method as in Reference Example 1 (1e).

$^1$H-NMR (CDCl$_3$) δ: 1.12-1.20 (1H, m), 1.43-1.52 (1H, m), 1.65-1.71 (1H, m), 1.77-1.85 (2H, m), 2.35-2.40 (1H, m), 2.53-2.59 (1H, m), 2.98-3.03 (1H, m), 3.10-3.14 (1H, m), 3.64-3.71 (2H, m), 6.18 (1H, t, J=75.0 Hz).

Reference Example 7

2-(Methoxymethyl)morpholine (7a) 4-Benzyl-2-(methoxymethyl)morpholine

[Chemical formula 52]

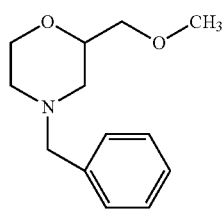

(4-Benzylmorpholin-2-yl)methanol (1.00 g, 4.83 mmol) was dissolved in N,N-dimethylformamide (15.0 mL), to which sodium hydride (content 55%, 255 mg, 5.85 mmol) was then added while cooling with ice. The resulting mixture was stirred for 20 minutes while cooling with ice. Subsequently, iodomethane (0.364 mL, 5.85 mmol) was added to the resulting reaction liquid, followed by stirring at room temperature for two hours.

Water and ethyl acetate were added to the reaction liquid, followed by extraction with ethyl acetate. The resulting organic layer was dried over sodium sulfate. The solvent was distilled off under reduced pressure. The residue thus obtained was purified by silica gel column chromatography (hexane:ethyl acetate, 100:0-80:20, V/V) to give the desired title compound (1.06 g, yield 99%).

$^1$H-NMR (CDCl$_3$) δ: 1.94-1.99 (1H, m), 2.16-2.22 (1H, m), 2.64-2.74 (2H, m), 3.32-3.42 (2H, m), 3.36 (3H, s), 3.46-3.54 (2H, m), 3.67-3.76 (2H, m), 3.87-3.90 (1H, m), 7.22-7.35 (5H, m).

(7b) 2-(Methoxymethyl)morpholine

[Chemical formula 53]

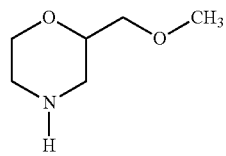

Using 4-benzyl-2-(methoxymethyl)morpholine (1.06 g, 4.79 mmol) produced in Reference Example 7 (7a), the desired title compound (554 mg, yield 88%) was obtained by the same method as in Reference Example 1 (1e).

$^1$H-NMR (CDCl$_3$) δ: 2.65 (1H, dd, J=12.0, 10.3 Hz), 2.78-2.82 (1H, m), 2.86-2.92 (2H, m), 3.34-3.42 (2H, m), 3.38 (3H, s), 3.60-3.68 (2H, m), 3.89-3.92 (1H, m).

Reference Example 8

4-[2-(1,4-Dioxan-2-ylmethoxy)ethoxy]piperidine

[Chemical formula 54]

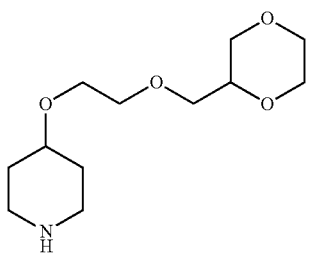

Using benzyl 4-(2-{[(4-methylphenyl)sulfony]oxy}ethoxy)piperidine-1-carboxylate (7.8 g, 18.0 mmol) produced in Reference Example 1 (1c) and 1,4-dioxan-2-ylmethanol (1.78 g, 15.1 mmol), the desired title compound (4.4 g, yield 61%) was obtained by the same method as in Reference Examples 1 (1d) and 1 (1e).

$^1$H-NMR (CDCl$_3$) δ: 1.41-1.54 (2H, m), 1.89-1.98 (2H, m), 2.61-2.69 (2H, m), 3.05-3.14 (2H, m), 3.37-3.83 (14H, m).

Reference Example 9

4-(2-{[Trans-4-methoxytetrahydrofuran-3-yl]oxy}ethoxy)piperidine (9a) Benzyl 4-{2-[(trans-4-hydroxytetrahydrofuran-3-yl)oxy]ethoxy}piperidine-1-carboxylate

[Chemical formula 55]

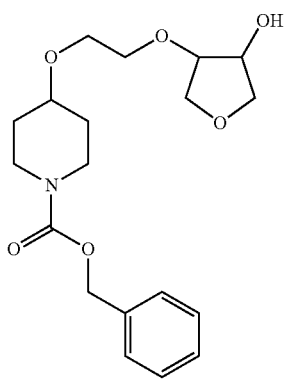

Benzyl 4-(2-hydroxyethoxy)piperidine-1-carboxylate (6.70 g, 24.0 mmol) produced in Reference Example 1 (1b) and 3,4-epoxytetrahydrofuran (1.03 g, 12.0 mmol) were dissolved in dichloromethane (5.0 mL). To the resulting mixture, a boron trifluoride diethyl ether complex (0.34 g, 2.4 mmol) was added at room temperature, followed by stirring for 16 hours. More boron trifluoride diethyl ether complex (0.34 g, 2.4 mmol) was added, followed by further stirring for two hours. Triethylamine (1.82 g, 18.0 mmol) was then added, and the resulting reaction liquid was directly purified by basic silica gel column chromatography (hexane:ethyl acetate, 100:0-0:100, ethyl acetate:methanol, 100:0-95:5, V/V) to give the desired title compound (2.14 g, yield 49%).

$^1$H-NMR (CDCl$_3$) δ: 1.51-1.59 (2H, m), 1.80-1.88 (2H, m), 1.90 (1H, d, J=5.2 Hz), 3.16-3.23 (2H, m), 3.48-3.54 (1H, m), 3.58-3.64 (2H, m), 3.66-3.70 (2H, m), 3.70-3.76 (2H, m), 3.78-3.87 (2H, m), 3.93-3.97 (2H, m), 4.04-4.09 (1H, m), 4.29-4.33 (1H, m), 5.12 (2H, s), 7.29-7.38 (5H, m).

MS (EI$^+$) m/z: 366 (M+H)$^+$ (9b) Benzyl 4-{2-[(trans-4-methoxytetrahydrofuran-3-yl)oxy]ethoxy}piperidine-1-carboxylate

[Chemical formula 56]

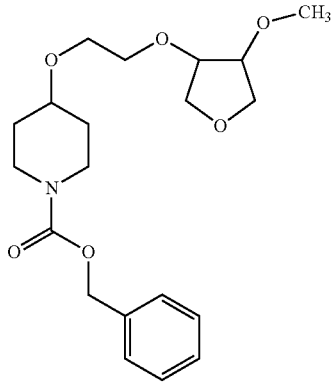

Using benzyl 4-{2-[(trans-4-hydroxytetrahydrofuran-3-yl)oxy]ethoxy}piperidine-1-carboxylate (2.28 g, 6.25 mmol) produced in Reference Example 9 (9a), the desired title compound (1.95 g, yield 82%) was obtained by the same method as in Reference Example 7 (7a).

$^1$H-NMR (CDCl$_3$) δ: 1.49-1.61 (2H, m), 1.78-1.89 (2H, m), 3.17-3.25 (2H, m), 3.37 (3H, s), 3.48-3.55 (1H, m), 3.58-3.67 (4H, m), 3.75-3.88 (5H, m), 3.90-3.96 (2H, m), 3.98-4.02 (1H, m), 5.12 (2H, s), 7.28-7.40 (5H, m).

MS (EI$^+$) m/z: 380 (M+H)$^+$ (9c) Trans-4-(2-{[4-methoxytetrahydrofuran-3-yl]oxy}ethoxy)piperidine

[Chemical formula 57]

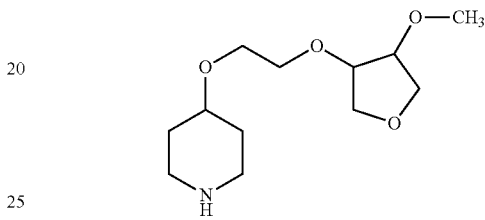

Using benzyl 4-(2-{[trans-4-methoxytetrahydrofuran-3-yl]oxy}ethoxy)piperidine-1-carboxylate (1.90 g, 5.01 mmol) produced in Reference Example 9 (9b), the desired title compound (1.23 g, yield 100%) was obtained by the same method as in Reference Example 1 (1e).

$^1$H-NMR (CDCl$_3$) δ: 1.41-1.48 (2H, m), 1.89-1.95 (2H, m), 2.58-2.64 (2H, m), 3.06-3.11 (2H, m), 3.37 (3H, s), 3.37-3.42 (1H, m), 3.60-3.67 (4H, m), 3.77-3.80 (2H, m), 3.86-3.88 (1H, m), 3.92-3.96 (2H, m), 4.01-4.03 (1H, m).

MS (FAB$^+$) m/z: 246 (M+H)$^+$

Reference Example 10

4-(2-{[Trans-4-(difluoromethoxy)tetrahydrofuran-3-yl]oxy}ethoxy)piperidine (10a) Benzyl 4-(2-{[trans-4-(difluoromethoxy)tetrahydrofuran-3-yl]oxy}ethoxy)piperidine-1-carboxylate

[Chemical formula 58]

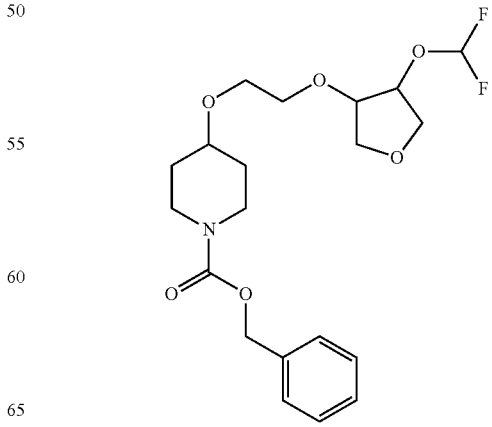

Using benzyl 4-{2-[(trans-4-hydroxytetrahydrofuran-3-yl)oxy]ethoxy}piperidine-1-carboxylate (2.65 g, 7.25 mmol) produced in Reference Example 9 (9a), the desired title compound (1.19 g, yield 40%) was obtained by the same method as in Reference Example 6 (6a).

$^1$H-NMR (CDCl$_3$) δ: 1.49-1.61 (2H, m), 1.77-1.90 (2H, m), 3.17-3.26 (2H, m), 3.47-3.55 (1H, m), 3.57-3.63 (2H, m), 3.64-3.73 (2H, m), 3.75-3.87 (4H, m), 3.96-4.05 (2H, m), 4.10-4.16 (1H, m), 4.73-4.77 (1H, m), 5.12 (2H, s), 6.26 (1H, t, J=73.4 Hz), 7.29-7.40 (5H, m).

MS (EI$^+$) m/z: 416 (M+H)$^+$ (10b) 4-(2-{[Trans-4-(difluoromethoxy)tetrahydrofuran-3-yl]oxy}ethoxy)piperidine

[Chemical formula 59]

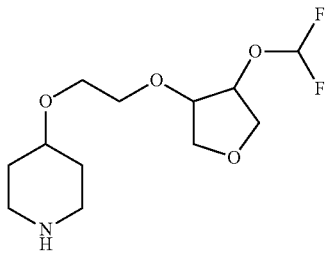

Using benzyl 4-(2-{[trans-4-(difluoromethoxy)tetrahydrofuran-3-yl]oxy}ethoxy)piperidine-1-carboxylate (1.88 g, 4.53 mmol) produced in Reference Example 10 (10a), the desired title compound (1.20 g, yield 94%) was obtained by the same method as in Reference Example 1 (1e).

$^1$H-NMR (CDCl$_3$) δ: 1.42-1.50 (2H, m), 1.82 (1H, br s), 1.89-1.95 (2H, m), 2.60-2.66 (2H, m), 3.06-3.12 (2H, m), 3.36-3.43 (1H, m), 3.59-3.62 (2H, m), 3.67-3.70 (2H, m), 3.78-3.85 (2H, m), 3.98-4.04 (2H, m), 4.12-4.15 (1H, m), 4.75-4.77 (1H, m), 6.27 (1H, t, J=73.6 Hz).

MS (FAB$^+$) m/z: 282 (M+H)$^+$

Reference Example 11

Cis-4-{2-[(4-methoxytetrahydrofuran-3-yl)oxy]ethoxy}piperidine

[Chemical formula 60]

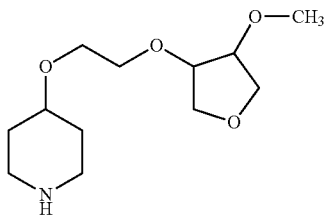

Using benzyl 4-(2-{[(4-methylphenyl)sulfonyl]oxy}ethoxy)piperidine-1-carboxylate (2.50 g, 5.77 mmol) produced in Reference Example 1 (1c) and 4-methoxytetrahydrofuran-3-ol (820 mg, 6.94 mmol), the desired title compound (1.20 g, yield 85%) was obtained by the same method as in Reference Examples 1 (1d) and 1 (1e).

$^1$H-NMR (CDCl$_3$) δ: 1.40-1.52 (2H, m), 1.88-1.98 (2H, m), 2.59-2.68 (2H, m), 3.05-3.13 (2H, m), 3.38-3.44 (1H, m), 3.45 (3H, s), 3.64-3.99 (9H, m), 4.08-4.16 (1H, m).

Reference Example 12

Piperidin-4-ylmethyl methyl(tetrahydro-2H-pyran-4-yl)carbamate (12a) Benzyl 4-({[methyl(tetrahydro-2H-pyran-4-yl)carbamoyl]oxy}methyl)piperidine-1-carboxylate

[Chemical formula 61]

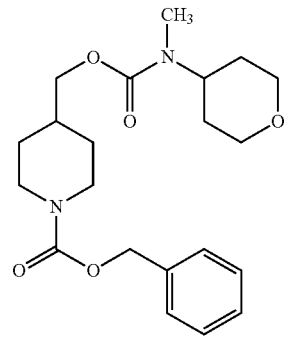

Benzyl 4-(hydroxymethyl)piperidine-1-carboxylate (2.14 g, 8.57 mmol) was dissolved in dichloromethane (26 mL), to which pyridine (1.04 mL, 12.9 mmol) and p-nitrophenyl chloroformate (2.07 g, 12.9 mmol) were added, followed by stirring at room temperature for 35 minutes under a nitrogen atmosphere. Subsequently, N-methyltetrahydro-2H-pyran-4-amine hydrochloride (1.30 g, 8.57 mmol) and triethylamine (3.59 mL, 25.7 mmol) were added, followed by further stirring for 4.5 hours. Water was added to the resulting reaction liquid, and the resulting mixture was extracted with dichloromethane. The resulting organic layer was dried over sodium sulfate and the solvent was distilled off under reduced pressure. The residue thus obtained was purified by silica gel column chromatography (hexane:ethyl acetate, 100:0-50:50, V/V) to give the desired title compound (2.22 g, yield 66%).

$^1$H-NMR (CDCl$_3$) δ: 1.17-1.28 (2H, br m), 1.53-1.60 (3H, m), 1.66-1.89 (5H, br m), 2.73-2.86 (5H, br m), 3.39-3.52 (2H, m), 3.94-3.99 (2H, m), 4.00-4.04 (2H, m), 4.16-4.29 (3H, br m), 5.13 (2H, s), 7.30-7.37 (5H, m).

MS (FAB$^+$) m/z: 391 (M+H)$^+$ (12b) Piperidin-4-ylmethyl methyl(tetrahydro-2H-pyran-4-yl)carbamate

[Chemical formula 62]

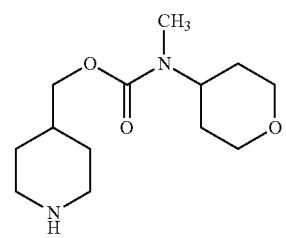

Using benzyl 4-({[methyl(tetrahydro-2H-pyran-4-yl)carbamoyl]oxy}methyl)piperidine-1-carboxylate (2.76 g, 8.62 mmol) produced in Reference Example 12 (12a), the desired title compound (1.54 g, yield 96%) was obtained by the same method as in Reference Example 1 (1e).

$^1$H-NMR (CDCl$_3$) δ: 1.17-1.31 (2H, m), 1.55-1.61 (2H, m), 1.62-1.98 (7H, m), 2.59-2.65 (2H, m), 2.77-2.82 (3H, br m), 3.09-3.13 (2H, m), 3.42-3.50 (2H, m), 3.93-3.96 (2H, m), 4.00-4.04 (2H, m).

MS (FAB$^+$) m/z: 257 (M+H)$^+$

Reference Example 13

2-(Tetrahydro-2H-pyran-4-yloxy)ethyl piperidine-1-carboxylate (13a) 1,4,8-Trioxaspiro[4.5]decane

[Chemical formula 63]

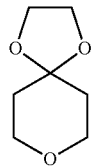

Tetrahydro-4H-pyran (6.00 g, 60.0 mmol) was dissolved in benzene (120 mL), to which ethylene glycol (11.2 g, 180 mmol) and p-toluenesulfonic acid monohydrate (1.14 g, 6.00 mmol) were added. Using a Dean-Stark tube, the resulting mixture was refluxed for two hours while removing water generated. To the resulting reaction liquid, a saturated aqueous solution of sodium bicarbonate was added, followed by extraction with ethyl acetate. The resulting organic layer was washed with saturated brine, and dried over sodium sulfate. The solvent was distilled off under reduced pressure. The residue thus obtained was purified by basic silica gel column chromatography (hexane:ethyl acetate, 100:0-0:100, V/V) to give the desired title compound (7.79 g, yield 90%).

$^1$H-NMR (CDCl$_3$) δ: 1.74 (4H, t, J=5.5 Hz), 3.74-3.80 (4H, m), 3.98 (4H, s).

(13b) 2-(Tetrahydro-2H-pyran-4-yloxy)ethanol

[Chemical formla 64]

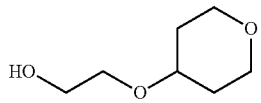

1,4,8-Trioxaspiro[4.5]decane (0.43 g, 3.0 mmol) produced in Reference Example 13 (13a) was dissolved in tetrahydrofuran (1.0 mL), and the resulting mixture was cooled to −50° C. Subsequently, a 1.0M solution of borane-tetrahydrofuran complex in tetrahydrofuran (3.6 mL) and trimethylsilyl trifluoromethanesulfonate (33 mg, 0.15 mmol) were added. The resulting mixture was warmed to room temperature, followed by stirring for 18 hours. A small amount of water was added, and then the resulting mixture was purified by basic silica gel column chromatography (hexane:ethyl acetate, 100:0-0:100, V/V) to give the desired title compound (0.39 g, yield 88%).

$^1$H-NMR (CDCl$_3$) δ: 1.53-1.65 (2H, m), 1.87-1.95 (2H, m), 2.01 (1H, t, J=6.3 Hz), 3.40-3.48 (2H, m), 3.50-3.57 (1H, m), 3.57-3.61 (2H, m), 3.71-3.77 (2H, m), 3.92-3.99 (2H, m).

(13c) Benzyl 2-(tetrahydro-2H-pyran-4-yloxy)ethyl piperazine-1,4-dicarboxylate

[Chemical formula 65]

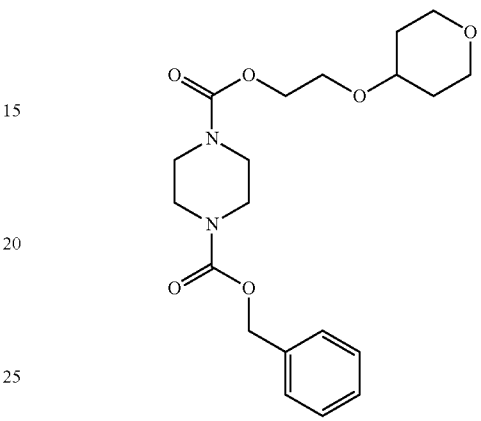

Using 2-(tetrahydro-2H-pyran-4-yloxy)ethanol (1.46 g, 10.0 mmol) produced in Reference Example 13 (13a) and benzyl 1-piperazine carboxylate (2.68 g, 13.0 mmol), the desired title compound (3.42 g, yield 87%) was obtained by the same method as in Reference Example 12 (12a).

$^1$H-NMR (CDCl$_3$) δ: 1.51-1.64 (2H, m), 1.85-1.93 (2H, m), 3.39-3.55 (11H, m), 3.68 (2H, t, J=5.0 Hz), 3.90-3.97 (2H, m), 4.25 (2H, t, J=5.0 Hz), 5.15 (2H, s), 7.30-7.42 (5H, m).

MS (EI$^+$) m/z: 393 (M+H)$^+$ (13d) 2-(Tetrahydro-2H-pyran-4-yloxy)ethyl piperidine-1-carboxylate

[Chemical formula 66]

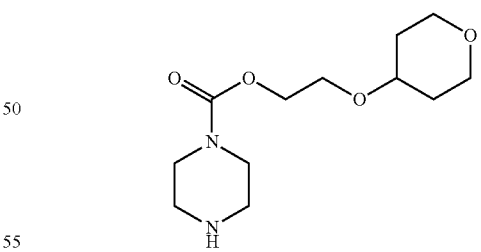

Using benzyl 2-(tetrahydro-2H-pyran-4-yloxy)ethyl piperidine-1,4-dicarboxylate (3.50 g, 8.92 mmol) produced in Reference Example 11 (11c), the desired title compound (2.26 g, yield 98%) was obtained by the same method as in Reference Example 1 (1e).

$^1$H-NMR (CDCl$_3$) δ: 1.56-1.63 (2H, m), 1.87-1.92 (2H, m), 2.80-2.85 (4H, br m), 3.41-3.47 (6H, m), 3.50-3.55 (1H, m), 3.68 (2H, t, J=4.9 Hz), 3.92-3.96 (2H, m), 4.24 (2H, t, J=4.9 Hz).

MS (FAB$^+$) m/z: 259 (M+H)$^+$

Reference Example 14

1,4:3,6-Dianhydro-2-O-[2-({1-[2-(ethoxycarbonyl)-1,6-naphthyridin-8-yl]piperidin-4-yl}oxy)ethyl]-5-O-methylhexitol (14a) 1,4:3,6-Dianhydro-2-O-[2-({1-[(benzyloxy)carbonyl]piperidin-4-yl}oxy)ethyl]-5-O-methyl-D-mannitol

[Chemical formula 67]

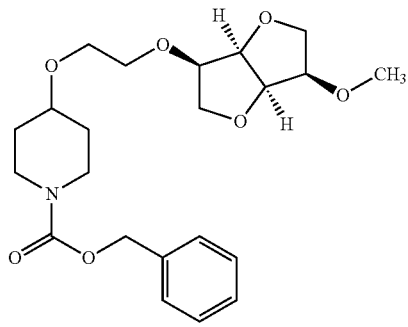

Using benzyl 4-(2-{[(4-methylphenyl)sulfonyl]oxy}ethoxy)piperidine-1-carboxylate (6.80 g, 15.7 mmol) produced in Reference Example 1 (1c) and 1,4:3,6-dianhydro-2-O-methyl-D-mannitol (2.10 g, 13.1 mmol), the desired title compound (3.6 g, yield 65%) was obtained by the same method as in Reference Example 1 (1d).

$^1$H-NMR (CDCl$_3$) δ: 1.49-1.61 (2H, m), 1.77-1.89 (2H, m), 3.15-3.25 (2H, m), 3.46 (3H, s), 3.48-3.56 (1H, m), 3.61-3.73 (5H, m), 3.75-3.86 (3H, m), 3.91-3.98 (1H, m), 4.01-4.17 (3H, m), 4.54-4.60 (2H, m), 5.12 (2H, s), 7.29-7.40 (5H, m).

(14b) 1,4:3,6-Dianhydro-2-O-methyl-5-O-[2-(piperidin-4-yloxy)ethyl]-D-mannitol

[Chemical formula 68]

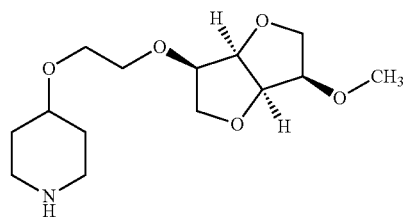

Using benzyl 1,4:3,6-dianhydro-2-O—[2-({1-[(benzyloxy)carbonyl]piperidin-4-yl}oxy)ethyl]-5-O-methyl-D-mannitol (3.60 g, 5.77 mmol) produced in Reference Example 14 (14a), the desired title compound (2.4 g, yield 98%) was obtained by the same method as in Reference Example 1 (1e). This compound was used in the subsequent reaction without isolation.

(14c) 1,4:3,6-Dianhydro-2-O-[2-({1-[2-(ethoxycarbonyl)-1,6-naphthyridin-8-yl]piperidin-4-yl}oxy)ethyl]-5-O-methyl-D-mannitol

[Chemical formula 69]

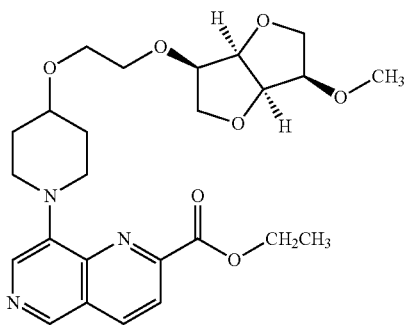

Using 1,4:3,6-dianhydro-2-O-methyl-5-O-[2-(piperidin-4-yloxy)ethyl]-D-mannitol (2.0 g, 6.96 mmol) produced in Reference Example 14 (14b), the desired title compound (683 mg, yield 65%) was obtained by the same method as in Example 1 (1a).

$^1$H-NMR (CDCl$_3$) δ: 1.49 (3H, t, J=7.1 Hz), 1.93-2.04 (2H, m), 2.13-2.22 (2H, m), 3.25-3.33 (2H, m), 3.47 (3H, s), 3.61-3.76 (6H, m), 3.81-4.00 (4H, m), 4.04-4.22 (3H, m), 4.49 (2H, q, J=7.1 Hz), 4.56-4.63 (2H, m), 8.25 (1H, d, J=8.5 Hz), 8.33 (1H, s), 8.37 (1H, d, J=8.5 Hz), 8.90 (1H, s).

Examples 25 to 117 shown below were produced in accordance with the aforementioned production method A, B, or C. In the following tables, "Ex. No." refers to the number of the Example, "Structure" refers to the structural formula of the compound of the Example, "Data" refers to the physical and chemical data of the compound of the Example, and "Mthd" specifies the production method A, B, or C by which the compound of the Example was produced.

TABLE 1

| Ex. No. | Structure | Data | Mthd |
|---|---|---|---|
| 25 | ![structure] | $^1$H-NMR (DMSO-D$_6$) δ: 1.02 (3H, d, J = 6.3 Hz), 1.47-1.55 (2H, m), 1.57-1.65 (1H, m), 1.76-1.81 (2H, m), 2.86-2.92 (2H, m), 3.93-3.98 (2H, m), 7.78 (1H, br s), 8.02 (1H, br s), 8.23 (1H, d, J = 8.3 Hz), 8.30 (1H, s), 8.67 (1H, d, J = 8.3 Hz), 8.99 (1H, s). MS (FAB$^+$) m/z: 271 (M + H)$^+$ | B |

TABLE 1-continued

| Ex. No. | Structure | Data | Mthd |
|---|---|---|---|
| 26 | 8-(3-methylpiperidin-1-yl)-1,6-naphthyridine-2-carboxamide | $^1$H-NMR (DMSO-D$_6$) δ: 0.96 (3H, d, J = 6.9 Hz), 1.11-1.19 (1H, m), 1.79-1.89 (3H, m), 1.93-2.02 (1H, m), 2.56-2.62 (1H, m), 2.84-2.90 (1H, m), 3.84-3.91 (2H, m), 7.76 (1H, br s), 8.03 (1H, br s), 8.23 (1H, d, J = 8.6 Hz), 8.29 (1H, s), 8.67 (1H, d, J = 8.6 Hz), 8.98 (1H, s). MS (FAB$^+$) m/z: 271 (M + H)$^+$ | B |
| 27 | 8-(4-hydroxypiperidin-1-yl)-1,6-naphthyridine-2-carboxamide | $^1$H-NMR (DMSO-D$_6$) δ: 1.65-1.77 (2H, m), 1.93-2.03 (2H, m), 3.06-3.15 (2H, m), 3.70-3.85 (3H, m), 4.74 (1H, br s), 7.78 (1H, br s), 8.01 (1H, br s), 8.23 (1H, d, J = 8.4 Hz), 8.30 (1H, s), 8.67 (1H, d, J = 8.4 Hz), 8.98 (1H, s). MS (FAB$^+$) m/z: 273 (M + H)$^+$ | B |
| 28 | 8-(4-phenylpiperazin-1-yl)-1,6-naphthyridine-2-carboxamide | $^1$H-NMR (CDCl$_3$) δ: 3.50-3.55 (4H, m), 3.65-3.71 (4H, m), 5.81 (1H, br s), 6.91-6.96 (1H, m), 7.02-7.07 (2H, m), 7.30-7.37 (2H, m), 7.89 (1H, br s), 8.38-8.49 (3H, m), 9.03 (1H, s). MS (EI$^+$) m/z: 334 (M + H)$^+$ | A |
| 29 | 8-(4-methoxypiperidin-1-yl)-1,6-naphthyridine-2-carboxamide | $^1$H-NMR (DMSO-D$_6$) δ: 1.73-1.80 (2H, m), 2.05-2.15 (2H, m), 3.11-3.22 (2H, m), 3.32 (3H, s), 3.40-3.48 (1H, m), 3.72-3.81 (2H, m), 7.81 (1H, br s), 7.98 (1H, br s), 8.23 (1H, d, J = 8.4 Hz), 8.31 (1H, s), 8.67 (1H, d, J = 8.4 Hz), 9.00 (1H, s). MS (FAB$^+$) m/z: 287 (M + H)$^+$ | B |

TABLE 1-continued

| Ex. No. | Structure | Data | Mthd |
|---|---|---|---|
| 30 | (4-fluorophenyl-piperazinyl 1,6-naphthyridine-2-carboxamide) | $^1$H-NMR (DMSO-D$_6$) δ: 3.36-3.42 (4H, m), 3.57-3.64 (4H, m), 7.01-7.13 (4H, m), 7.82 (1H, br s), 7.97 (1H, br s), 8.25 (1H, d, J = 8.4 Hz), 8.35 (1H, s), 8.69 (1H, d, J = 8.4 Hz), 9.05 (1H, s). MS (FAB$^+$) m/z: 352 (M + H)$^+$. | B |

TABLE 2

| Ex. No. | Structure | Data | Mthd |
|---|---|---|---|
| 31 | (3-methoxypiperidinyl 1,6-naphthyridine-2-carboxamide) | $^1$H-NMR (CDCl$_3$) δ: 1.77-1.87 (2H, m), 1.97-2.07 (1H, m), 2.08-2.19 (1H, m), 3.33-3.45 (3H, m), 3.48 (3H, s), 3.66-3.72 (1H, m), 3.99-4.06 (1H, m), 5.70 (1H, s), 8.32 (1H, s), 8.38 (1H, d, J = 8.2 Hz), 8.42 (1H, d, J = 8.2 Hz), 8.60 (1H, s), 8.93 (1H, s). MS (EI$^+$) m/z: 287 (M + H)$^+$ | B |
| 32 | (3-fluorophenyl-piperazinyl 1,6-naphthyridine-2-carboxamide) | $^1$H-NMR (CDCl$_3$) δ: 3.50-3.55 (4H, m), 3.65-3.69 (4H, m), 5.70 (1H, s), 6.58-6.63 (1H, m), 6.68-6.73 (1H, m), 6.77-6.81 (1H, m), 7.23-7.28 (1H, m), 7.85 (1H, s), 8.41 (1H, s), 8.44 (1H, d, J = 8.2 Hz), 8.48 (1H, d, J = 8.2 Hz), 9.02 (1H, s). MS (EI$^+$) m/z: 352 (M + H)$^+$ | A |
| 33 | (phenyl-diazepanyl 1,6-naphthyridine-2-carboxamide) | $^1$H-NMR (DMSO-D$_6$) δ: 2.11-2.19 (2H, m), 3.56-3.62 (2H, m), 3.77-3.84 (4H, m), 3.98-4.04 (2H, m), 6.52-6.58 (1H, m), 6.75-6.80 (2H, m), 7.10-7.17 (2H, m), 7.69 (1H, br s), 7.97 (1H, br s), 8.17 (1H, d, J = 8.5 Hz), 8.29 (1H, s), 8.58 (1H, d, J = 8.5 Hz), 8.76 (1H, s). MS (FAB$^+$) m/z: 348 (M + H)$^+$ | A |

TABLE 2-continued

| | | | |
|---|---|---|---|
| 34 | (pyrrol-1-yl isoquinoline-6-carboxamide structure) | ¹H-NMR (DMSO-D₆) δ: 6.38-6.44 (2H, m), 7.21-7.28 (2H, m), 7.71 (1H, br s), 8.15 (1H, d, J = 8.6 Hz), 8.29-8.33 (2H, m), 8.36 (1H, d, J = 8.6 Hz), 8.59 (1H, s), 9.43 (1H, s).<br>MS (FAB⁺) m/z: 238 (M + H)⁺. | C |
| 35 | (morpholino isoquinoline-6-carboxamide structure) | ¹H-NMR (CDCl₃) δ: 3.17-3.23 (4H, m), 3.99-4.03 (4H, m), 5.73 (1H, br s), 6.22 (1H, br s), 7.96 (1H, d, J = 8.6 Hz), 8.06 (1H, d, J = 8.6 Hz), 8.30 (1H, s), 8.61 (1H, s), 9.06 (1H, s).<br>MS (EI⁺) m/z: 258 (M + H)⁺ | C |
| 36 | (pyrrolidin-1-yl isoquinoline-6-carboxamide structure) | ¹H-NMR (CDCl₃) δ: 2.03-2.10 (4H, m), 3.55-3.62 (4H, m), 5.74 (1H, br s), 6.21 (1H, br s), 7.86 (1H, d, J = 8.6 Hz), 7.96 (1H, d, J = 8.6 Hz), 8.08 (1H, s), 8.77 (1H, s), 8.78 (1H, s).<br>MS (EI⁺) m/z: 242 (M + H)⁺ | C |

TABLE 3

| | | | |
|---|---|---|---|
| 37 | (4-(methoxymethyl)piperidin-1-yl isoquinoline-6-carboxamide structure) | | ¹H-NMR (DMSO-D₆) δ: 1.51-1.65 (2H, m), 1.72-1.88 (3H, m), 2.79-2.88 (2H, m), 3.29-3.36 (2H, m), 3.30 (3H, s), 3.37-3.46 (2H, m), 7.62 (1H, br s), 8.05 (1H, d, J = 8.5 Hz), 8.14 (1H, d, J = 8.5 Hz), 8.22 (1H, s), 8.29 (1H, br s), 8.49 (1H, s), 9.03 (1H, s).<br>MS (FAB⁺) m/z: 300 (M + H)⁺ | C |
| 38 | (3-ethoxypiperidin-1-yl isoquinoline-6-carboxamide structure) | | ¹H-NMR (DMSO-D₆) δ: 1.14 (3H, t, J = 7.0 Hz), 1.36-1.48 (1H, m), 1.75-1.95 (2H, m), 2.03-2.12 (1H, m), 2.76-2.88 (2H, m), 3.22-3.27 (1H, m), 3.41-3.49 (1H, m), 3.56 (2H, q, J = 7.0 Hz), 3.65-3.73 (1H, m), 7.60 (1H, br s), 8.05 (1H, d, J = 8.5 Hz), 8.15 (1H, d, J = 8.5 Hz), 8.23 (1H, s), 8.24 (1H, br s), 8.54 (1H, s), 9.04 (1H, s). MS (FAB⁺) m/z: 300 (M + H)⁺ | C |
| 39 | (chiral 3-(methoxymethyl)piperidin-1-yl isoquinoline-6-carboxamide structure) | Chiral | ¹H-NMR (DMSO-D₆) δ: 1.16-1.30 (1H, m), 1.77-1.91 (3H, m), 2.13-2.25 (1H, m), 2.61-2.70 (1H, m), 2.80-2.88 (1H, m), 3.25 (3H, s), 3.28-3.39 (4H, m), 7.62 (1H, br s), 8.05 (1H, d, J = 8.3 Hz), 8.15 (1H, d, J = 8.5 Hz), 8.21 (1H, s), 8.26 (1H, br s), 8.51 (1H, s), 9.03 1H, s). MS (FAB⁺) m/z: 300 (M + H)⁺ | C |

TABLE 3-continued

| | | | | |
|---|---|---|---|---|
| 40 | *(structure: 3-(methoxymethyl)piperidin-1-yl attached to isoquinoline-6-carboxamide)* | Chiral | ¹H-NMR (DMSO-D₆) δ: 1.16-1.31 (1H, m), 1.76-1.90 (3H, m), 2.13-2.26 (1H, m), 2.60-2.71 (1H, m), 2.78-2.90 (1H, m), 3.25 (3H, s), 3.27-3.40 (4H, m), 7.62 (1H, br s), 8.04 (1H, d, J = 8.5 Hz), 8.15 (1H, d, J = 8.5 Hz), 8.21 (1H, s), 8.25 (1H, br s), 8.51 (1H, s), 9.03 (1H, s). MS (FAB⁺) m/z: 300 (M + H)⁺ | C |
| 41 | *(structure: 3-(2-methoxyethyl)piperidin-1-yl attached to isoquinoline-6-carboxamide)* | | ¹H-NMR (DMSO-D₆) δ: 1.09-1.22 (1H, m), 1.46-1.58 (2H, m), 1.79-1.94 (3H, m), 1.94-2.06 (1H, m), 2.53-2.58 (1H, m), 2.74-2.85 (1H, m), 3.21 (3H, s), 3.33-3.44 (4H, m), 7.61 (1H, br s), 8.04 (1H, d, J = 8.5 Hz), 8.14 (1H, d, J = 8.5 Hz), 8.21 (1H, s), 8.25 (1H, br s), 8.51 (1H, s), 9.03 (1H, s). MS (FAB⁺) m/z: 314 (M + H)⁺ | C |
| 42 | *(structure: 4-phenylpiperidin-1-yl attached to isoquinoline-6-carboxamide)* | | ¹H-NMR (CDCl₃) δ: 2.03-2.21 (4H, m), 2.73-2.83 (1H, m), 2.99-3.09 (2H, m), 3.54-3.63 (2H, m), 5.87 (1H, br s), 6.25 (1H, br s), 7.32-7.41 (5H, m), 7.97 (1H, d, J = 8.5 Hz), 8.04 (1H, d, J = 8.5 Hz), 8.32 (1H, s), 8.60 (1H, s), 9.02 (1H, s). MS (EI⁺) m/z: 332 (M + H)⁺ | C |

TABLE 4

| | | | |
|---|---|---|---|
| 43 | *(structure: 4,4-difluoropiperidin-1-yl attached to isoquinoline-6-carboxamide)* | ¹H-NMR (CDCl₃) δ: 2.25-2.39 (4H, m), 3.31 (4H, m), 5.87 (1H, br s), 6.23 (1H, br s), 7.95 (1H, d, J = 8.5 Hz), 8.06 (1H, d, J = 8.5 Hz), 8.32 (1H, s), 8.57 (1H, d, J = 0.7 Hz), 9.06 (1H, s). MS (EI⁺) m/z: 292 (M + H)⁺ | C |
| 44 | *(structure: 4-(trifluoromethyl)piperidin-1-yl attached to isoquinoline-6-carboxamide)* | ¹H-NMR (CDCl₃) δ: 1.93-2.13 (4H, m), 2.22-2.34 (1H, m), 2.86-2.95 (2H, m), 3.48-3.58 (2H, m), 5.91 (1H, br s), 6.26 (1H, br s), 7.97 (1H, d, J = 8.5 Hz), 8.05 (1H, d, J = 8.5 Hz), 8.52 (1H, d, J = 0.7 Hz), 9.04 (1H, s). MS (EI⁺) m/z: 324 (M + H)⁺ | C |

TABLE 4-continued
| 45 | 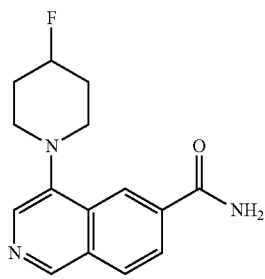 [SMILES: NC(=O)c1ccc2cncc(N3CCC(F)CC3)c2c1] | ¹H-NMR (CDCl₃) δ: 2.10-2.30 (4H, m), 3.10-3.19 (2H, m), 3.31-3.40 (2H, m), 4.84-5.04 (1H, m), 5.82 (1H, br s), 6.23 (1H, br s), 7.95 (1H, d, J = 8.5 Hz), 8.04 (1H, d, J = 8.5 Hz), 8.56 (1H, s), 9.03 (1H, s). MS (EI⁺) m/z: 274 (M + H)⁺ | C |
| --- | --- | --- | --- |
| 46 | 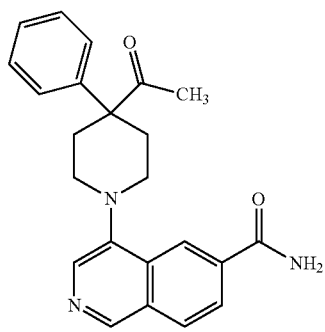 [SMILES: CC(=O)C1(c2ccccc2)CCN(c2cncc3ccc(C(N)=O)cc23)CC1] | ¹H-NMR (CDCl₃) δ: 2.00 (3H, s), 2.35-2.44 (2H, m), 2.69-2.77 (2H, m), 3.10-3.19 (2H, m), 3.31-3.38 (2H, m), 5.85 (1H, br s), 6.30 (1H, br s), 7.30-7.35 (1H, m), 7.38-7.43 (4H, m), 7.96 (1H, d, J = 8.5 Hz), 8.02 (1H, d, J = 8.5 Hz), 8.23 (1H, s), 8.53 (1H, s), 9.00 (1H, s). MS (EI⁺) m/z: 374 (M + H)⁺ | C |
| 47 | 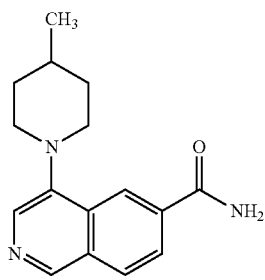 [SMILES: CC1CCN(c2cncc3ccc(C(N)=O)cc23)CC1] | ¹H-NMR (CDCl₃) δ: 1.07 (3H, d, J = 5.9 Hz), 1.52-1.67 (3H, m), 1.81-1.88 (2H, m), 2.83-2.91 (2H, m), 3.39-3.45 (2H, m), 5.88 (1H, br s), 6.24 (1H, br s), 7.96 (1H, d, J = 8.5 Hz), 8.01 (1H, d, J = 8.5 Hz), 8.54 (1H, s), 8.98 (1H, s). MS (EI⁺) m/z: 270 (M + H)⁺ | C |
| 48 | 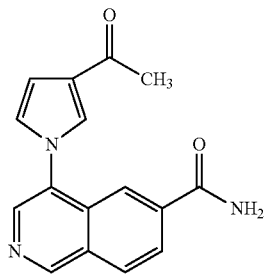 [SMILES: CC(=O)c1ccn(-c2cncc3ccc(C(N)=O)cc23)c1] | ¹H-NMR (DMSO-D₆) δ: 2.42 (3H, s), 6.77-6.81 (1H, m), 7.30-7.34 (1H, m), 7.69 (1H, br s), 8.08 (1H, s), 8.20 (1H, d, J = 8.5 Hz), 8.21 (1H, s), 8.33 (1H, s), 8.40 (1H, d, J = 8.5 Hz), 8.68 (1H, s), 9.51 (1H, s). MS (EI⁺) m/z: 279 (M)+ | C |

TABLE 5
| 49 | 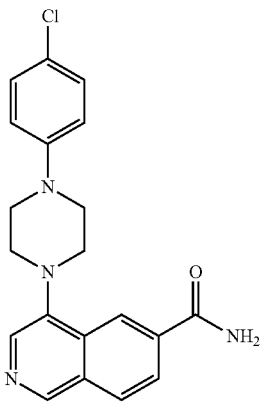 [SMILES: NC(=O)c1ccc2cncc(N3CCN(c4ccc(Cl)cc4)CC3)c2c1] | ¹H-NMR (DMSO-D₆) δ: 3.26-3.32 (4H, m), 3.43-3.49 (4H, m), 7.07 (2H, d, J = 8.9 Hz), 7.29 (2H, d, J = 8.9 Hz), 7.63 (1H, br s), 8.08 (1H, d, J = 8.5 Hz), 8.19 (1H, d, J = 8.5 Hz), 8.30 (1H, s), 8.32 (1H, br s), 8.57 (1H, s), 9.10 (1H, s). MS (FAB⁺) m/z: 367 (M + H)⁺ | C |
| --- | --- | --- | --- |
| 50 | 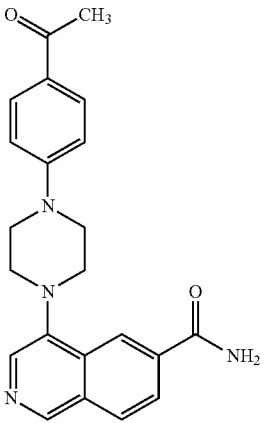 [SMILES: CC(=O)c1ccc(N2CCN(c3cncc4ccc(C(N)=O)cc34)CC2)cc1] | ¹H-NMR (DMSO-D₆) δ: 2.48 (3H, s), 3.26-3.32 (4H, m), 3.64-3.69 (4H, m), 7.11 (2H, d, J = 9.2 Hz), 7.67 (1H, br s), 7.87 (2H, d, J = 9.2 Hz), 8.09 (1H, d, J = 8.7 Hz), 8.20 (1H, d, J = 8.7 Hz), 8.31 (1H, s), 8.35 (1H, br s), 8.59 (1H, s), 9.11 (1H, s). MS (FAB⁺) m/z: 375 (M + H)⁺ | C |
| 51 | 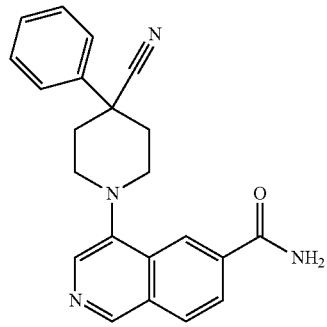 [SMILES: N#CC1(c2ccccc2)CCN(c2cncc3ccc(C(N)=O)cc23)CC1] | ¹H-NMR (CDCl₃) δ: 2.29-2.40 (2H, m), 2.42-2.54 (2H, m), 3.40-3.52 (2H, m), 3.53-3.63 (2H, m), 5.89 (1H, br s), 6.28 (1H, br s), 7.37-7.43 (1H, m), 7.45-7.51 (2H, m), 7.58-7.65 (2H, m), 7.93 (1H, d, J = 8.5 Hz), 8.07 (1H, d, J = 8.5 Hz), 8.41 (1H, s), 8.61 (1H, s), 9.08 (1H, s). MS (EI⁺) m/z: 357 (M + H)⁺ | C |
| 52 | 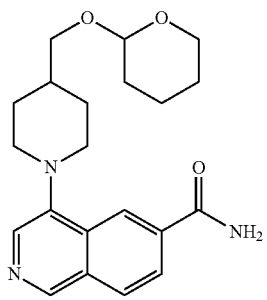 [SMILES: NC(=O)c1ccc2cncc(N3CCC(COC4CCCCO4)CC3)c2c1] | ¹H-NMR (DMSO-D₆) δ: 1.43-1.69 (7H, m), 1.70-1.94 (2H, m), 2.80-2.88 (2H, m), 3.26-3.34 (2H, m), 3.36-3.50 (4H, m), 3.59-3.64 (1H, m), 3.75-3.81 (1H, m), 4.61 (1H, t, J = 3.4 Hz), 7.63 (1H, br s), 8.05 (1H, d, J = 8.5 Hz), 8.15 (1H, d, J = 8.5 Hz), 8.22 (1H, s), 8.30 (1H, br s), 8.49 (1H, s), 9.03 (1H, s). MS (FAB⁺) m/z: 370 (M + H)⁺ | C |

TABLE 5-continued
| 53 | 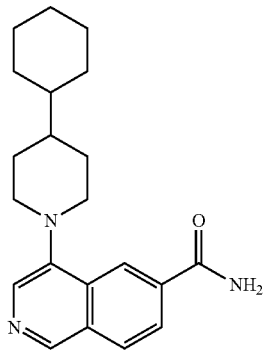 [SMILES: NC(=O)c1ccc2cncc(N3CCC(C4CCCCC4)CC3)c2c1] | ¹H-NMR (DMSO-D₆) δ: 0.95-1.09 (2H, m), 1.11-1.32 (4H, m), 1.52-1.69 (3H, m), 1.70-1.88 (5H, m), 2.77 (2H, m), 3.35-3.49 (4H, m), 7.63 (1H, s), 8.04 (1H, d, J = 8.5 Hz), 8.14 (1H, d, J = 8.5 Hz), 8.20 (1H, s), 8.29 (1H, s), 8.49 (1H, s), 9.02 (1H, s). MS (EI⁺) m/z: 338 (M + H)⁺ | C |
| --- | --- | --- | --- |
| 54 | 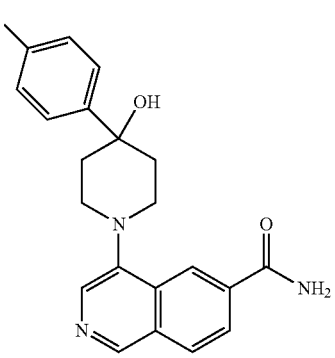 | ¹H-NMR (DMSO-D₆) δ: 1.77-1.86 (2H, m), 2.29-2.40 (2H, m), 3.25-3.37 (4H, m), 5.21 (1H, s), 7.44 (2H, d, J = 8.3 Hz), 7.64 (1H, s), 7.65 (2H, d, J = 8.3 Hz), 8.07 (1H, d, J = 8.5 Hz), 8.16 (1H, d, J = 8.5 Hz), 8.30 (1H, s), 8.33 (1H, s), 8.57 (1H, s), 9.05 (1H, s). MS (EI⁺) m/z: 382 (M + H)⁺ | C |
TABLE 6
| 55 | 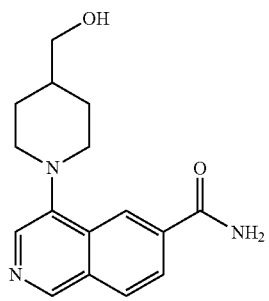 [SMILES: NC(=O)c1ccc2cncc(N3CCC(CO)CC3)c2c1] | ¹H-NMR (DMSO-D₆) δ: 1.48-1.65 (3H, m), 1.82-1.88 (2H, m), 2.78-2.85 (2H, m), 3.38-3.45 (4H, m), 4.57 (1H, t, J = 5.3 Hz), 7.64 (1H, br s), 8.05 (1H, d, J = 8.3 Hz), 8.15 (1H, d, J = 8.3 Hz), 8.22 (1H, s), 8.30 (1H, br s), 8.50 (1H, s), 9.03 (1H, s). MS (FAB⁺) m/z: 286 (M + H)⁺ | C |
| --- | --- | --- | --- |
| 56 | 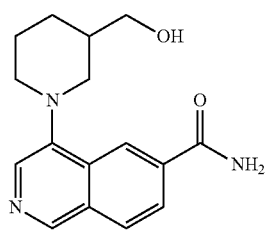 [SMILES: NC(=O)c1ccc2cncc(N3CCCC(CO)C3)c2c1] | ¹H-NMR (DMSO-D₆) δ: 1.19-1.27 (1H, m), 1.79-1.85 (3H, m), 1.95-2.02 (1H, m), 2.71-2.77 (1H, m), 2.82-2.88 (1H, m), 3.28-3.33 (2H, m), 3.43-3.49 (2H, m), 4.67 (1H, t, J = 5.2 Hz), 7.63 (1H, br s), 8.06 (1H, d, J = 8.6 Hz), 8.15 (1H, d, J = 8.6 Hz), 8.21 (1H, s), 8.29 (1H, br s), 8.53 (1H, s), 9.03 (1H, s). MS (FAB⁺) m/z: 286 (M + H)⁺ | C |

TABLE 6-continued
| | | | |
|---|---|---|---|
| 57 | 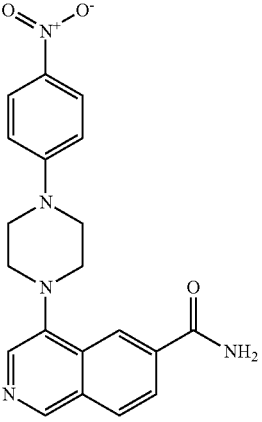 [SMILES: NC(=O)c1ccc2cncc(N3CCN(c4ccc([N+](=O)[O-])cc4)CC3)c2c1] | $^1$H-NMR (DMSO-D$_6$) δ: 3.27-3.32 (4H, m), 3.76-3.81 (4H, m), 7.16 (2H, d, J = 9.6 Hz), 7.68 (1H, s), 8.10 (1H, d, J = 8.3 Hz), 8.12 (2H, d, J = 9.6 Hz), 8.20 (1H, d, J = 8.3 Hz), 8.30 (1H, s), 8.36 (1H, br s), 8.60 (1H, s), 9.11 (1H, s). MS (FAB$^+$) m/z: 378 (M + H)$^+$ | C |
| 58 | 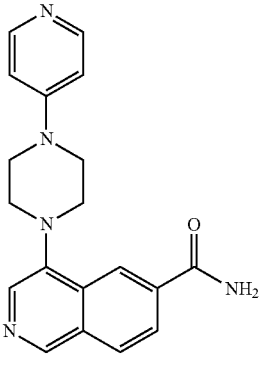 [SMILES: NC(=O)c1ccc2cncc(N3CCN(c4ccncc4)CC3)c2c1] | $^1$H-NMR (DMSO-D$_6$) δ: 3.24-3.29 (4H, m), 3.61-3.66 (4H, m), 6.92-6.96 (2H, m), 7.67 (1H, br s), 8.09 (1H, d, J = 8.7 Hz), 8.19 (1H, d, J = 8.7 Hz), 8.21-8.24 (2H, m), 8.30 (1H, s), 8.35 (1H, br s), 8.59 (1H, s), 9.11 (1H, s). MS (EI$^+$) m/z: 333 (M)$^+$ | C |
| 59 | 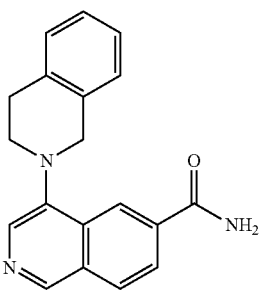 [SMILES: NC(=O)c1ccc2cncc(N3CCc4ccccc4C3)c2c1] | $^1$H-NMR (DMSO-D$_6$) δ: 3.09-3.14 (2H, m), 3.45-3.50 (2H, m), 4.40 (2H, s), 7.17-7.28 (4H, m), 7.61 (1H, br s), 8.08 (1H, d, J = 8.5 Hz), 8.19 (1H, d, J = 8.5 Hz), 8.32 (1H, br s), 8.33 (1H, s), 8.58 (1H, s), 9.08 (1H, s). MS (EI$^+$) m/z: 304 (M + H)$^+$ | C |
| 60 | 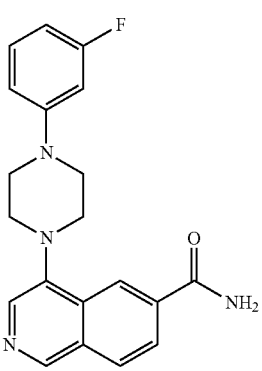 [SMILES: NC(=O)c1ccc2cncc(N3CCN(c4cccc(F)c4)CC3)c2c1] | $^1$H-NMR (DMSO-D$_6$) δ: 3.26-3.31 (4H, m), 3.48-3.53 (4H, m), 6.57-6.63 (1H, m), 6.83-6.90 (2H, m), 7.24-7.30 (1H, m), 7.65 (1H, br s), 8.09 (1H, d, J = 8.3 Hz), 8.19 (1H, d, J = 8.3 Hz), 8.30 (1H, s), 8.33 (1H, br s), 8.58 (1H, s), 9.10 (1H, s). MS (FAB$^+$) m/z: 351 (M + H)$^+$ | C |

TABLE 7

| | | | |
|---|---|---|---|
| 61 | (4-methylphenyl-piperazinyl isoquinoline-6-carboxamide structure) | ¹H-NMR (DMSO-D₆) δ: 2.23 (3H, s), 3.26-3.31 (4H, m), 3.37-3.42 (4H, m), 6.96 (2H, d, J = 8.5 Hz), 7.08 (2H, d, J = 8.5 Hz), 7.64 (1H, br s), 8.08 (1H, d, J = 8.7 Hz), 8.18 (1H, d, J = 8.7 Hz), 8.30 (1H, s), 8.32 (1H, br s), 8.57 (1H, s), 9.09 (1H, s). MS (FAB⁺) m/z: 347 (M + H)⁺ | C |
| 62 | (4-cyanophenyl-piperazinyl isoquinoline-6-carboxamide structure) | ¹H-NMR (DMSO-D₆) δ: 3.25-3.30 (4H, m), 3.64-3.69 (4H, m), 7.15 (2H, d, J = 8.9 Hz), 7.65 (2H, d, J = 8.9 Hz), 7.66 (1H, br s), 8.09 (1H, d, J = 8.5 Hz), 8.19 (1H, d, J = 8.5 Hz), 8.30 (1H, s), 8.34 (1H, br s), 8.59 (1H, s), 9.10 (1H, s). MS (FAB⁺) m/z: 358 (M + H)⁺ | C |
| 63 | (phenyl-homopiperazinyl isoquinoline-6-carboxamide structure) | ¹H-NMR (DMSO-D₆) δ: 2.18-2.23 (2H, m), 3.17-3.21 (2H, m), 3.43-3.47 (2H, m), 3.71-3.75 (2H, m), 3.78-3.82 (2H, m), 6.60 (1H, t, J = 7.3 Hz), 6.81 (2H, d, J = 8.3 Hz), 7.18 (2H, dd, J = 8.3, 7.3 Hz), 7.65 (1H, br s), 8.06 (1H, d, J = 8.5 Hz), 8.15 (1H, d, J = 8.5 Hz), 8.27 (1H, br s), 8.27 (1H, s), 8.63 (1H, s), 9.01 (1H, s). MS (FAB⁺) m/z: 347 (M + H)⁺ | C |
| 64 | (4-phenoxypiperidinyl isoquinoline-6-carboxamide structure) | ¹H-NMR (CDCl₃) δ: 2.07-2.19 (2H, m), 2.21-2.34 (2H, m), 3.06-3.18 (2H, m), 3.39-3.51 (2H, m), 4.53-4.64 (1H, m), 6.32 (1H, br s), 6.51 (1H, br s), 6.94-7.04 (3H, m), 7.26-7.36 (2H, m), 7.94-8.06 (2H, m), 8.30 (1H, s), 8.57 (1H, s), 9.00 (1H, s). MS (EI⁺) m/z: 348 (M + H)⁺ | C |

TABLE 7-continued

| 65 | [tetrahydropyran-piperidine-isoquinoline-carboxamide structure] | ¹H-NMR (CDCl₃) δ: 1.26-1.48 (4H, m), 1.56-1.67 (2H, m), 1.68-1.77 (2H, m), 1.88-1.98 (2H, m), 2.79-2.92 (2H, m), 3.36-3.46 (2H, m), 3.47-3.54 (2H, m), 4.00-4.09 (2H, m), 5.80 (1H, br s), 6.25 (1H, br s), 7.95 (2H, d, J = 8.5 Hz), 8.03 (2H, d, J = 8.5 Hz), 8.25 (1H, s), 8.55 (1H, s), 9.00 (1H, s). MS (EI⁺) m/z: 340 (M + H)⁺ | C |
| 66 | [3-methylpyrrole-isoquinoline-carboxamide structure] | ¹H-NMR (DMSO-D₆) δ: 2.16 (3H, s), 6.24-6.26 (1H, m), 6.99-7.01 (1H, br m), 7.11-7.13 (1H, m), 7.69 (1H, br s), 8.15 (1H, d, J = 8.7 Hz), 8.31 (1H, br s), 8.34 (1H, d, J = 8.7 Hz), 8.36 (1H, s), 8.54 (1H, s), 9.40 (1H, s). MS (EI⁺) m/z: 251 (M)⁺ | C |

TABLE 8

| 67 | [decahydroisoquinoline-isoquinoline-carboxamide structure] | ¹H-NMR (DMSO-D₆) δ: 0.94-1.07 (1H, m), 1.07-1.18 (2H, m), 1.24-1.38 (2H, m), 1.48-1.65 (3H, m), 1.65-1.79 (4H, m), 2.53-2.58 (1H, m), 2.78-2.87 (1H, m), 3.19-3.26 (1H, m), 3.37-3.45 (1H, m), 7.61 (1H, br s), 8.03 (1H, d, J = 8.5 Hz), 8.13 (1H, d, J = 8.5 Hz), 8.20 (1H, s), 8.27 (1H, br s), 8.49 (1H, s), 9.01 (1H, s). MS (FAB⁺) m/z: 310 (M + H)⁺. | C |
| 68 | [tetrahydrofuran-methoxy-piperidine-isoquinoline-carboxamide structure] HCl | ¹H-NMR (DMSO-D₆) δ: 1.53-1.63 (1H, m), 1.74-1.95 (5H, m), 2.04-2.14 (2H, m), 2.98-3.08 (2H, m), 3.35-3.40 (3H, m), 3.58-3.65 (3H, m), 3.72-3.77 (1H, m), 3.91-3.97 (1H, m), 7.80 (1H, br s), 8.22-8.25 (2H, m), 8.41 (1H, d, J = 9.3 Hz), 8.47 (1H, br s), 8.57 (1H, s), 9.35 (1H, s). MS (FAB⁺) m/z: 356 (M + H)⁺. | C |

TABLE 8-continued
| | | | |
|---|---|---|---|
| 69 | 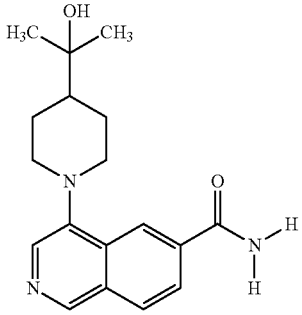 [SMILES: CC(C)(O)C1CCN(c2cncc3ccc(C(N)=O)cc23)CC1] | ¹H-NMR (DMSO-D₆) δ: 1.14 (6H, s), 1.35-1.44 (1H, m), 1.55-1.69 (2H, m), 1.82-1.91 (2H, m), 2.70-2.80 (2H, m), 3.43-3.51 (2H, m), 4.20 (1H, s), 7.62 (1H, br s), 8.04 (1H, d, J = 8.5 Hz), 8.14 (1H, d, J = 8.5 Hz), 8.21 (1H, s), 8.29 (1H, br s), 8.49 (1H, s), 9.02 (1H, s). MS (FAB⁺) m/z: 314 (M + H)⁺. | C |
| 70 | 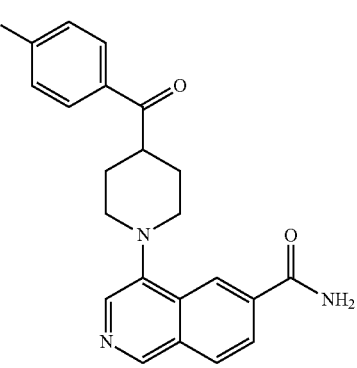 | ¹H-NMR (DMSO-D₆) δ: 1.94-2.02 (4H, m), 2.98-3.08 (2H, m), 3.43-3.50 (2H, m), 3.63-3.73 (1H, m), 7.39 (2H, t, J = 8.8 Hz), 7.61 (1H, br s), 8.05 (1H, d, J = 8.5 Hz), 8.11-8.17 (3H, m), 8.25 (1H, s), 8.31 (1H, br s), 8.50 (1H, s), 9.05 (1H, s). MS (FAB⁺) m/z: 378 (M + H)⁺. | C |
| 71 | 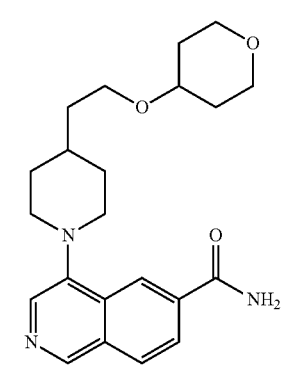 [SMILES: NC(=O)c1ccc2cncc(N3CCC(CCOC4CCOCC4)CC3)c2c1] | ¹H-NMR (DMSO-D₆) δ: 1.35-1.44 (2H, m), 1.53-1.61 (5H, m), 1.86 (4H, d, J = 11.5 Hz), 2.82 (2H, t, J = 11.2 Hz), 3.29-3.42 (4H, m), 3.44-3.51 (1H, m), 3.53 (2H, t, J = 6.0 Hz), 3.78-3.83 (2H, m), 7.64 (1H, br s), 8.05 (1H, d, J = 8.3 Hz), 8.14 (1H, d, J = 8.3 Hz), 8.21 (1H, s), 8.30 (1H, br s), 8.50 (1H, s), 9.02 (1H, s). MS (FAB⁺) m/z: 384 (M + H)⁺ | C |
| 72 | 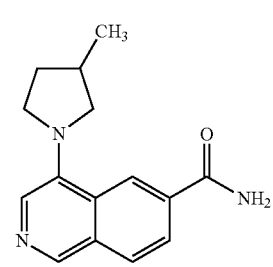 | ¹H-NMR (DMSO-D₆) δ: 1.15 (3H, d, J = 6.6 Hz), 1.66-1.69 (1H, m), 2.18-2.19 (1H, m), 2.43-2.51 (2H, m), 3.40-3.42 (1H, m), 3.76-3.87 (2H, m), 7.81-7.83 (2H, m), 8.26 (1H, d, J = 8.5 Hz), 8.37 (1H, d, J = 8.8 Hz), 8.41 (1H, br s), 8.92 (1H, s), 9.01 (1H, s). MS (FAB⁺) m/z 256 (M + H)⁺ | C |

TABLE 9

| 73 | 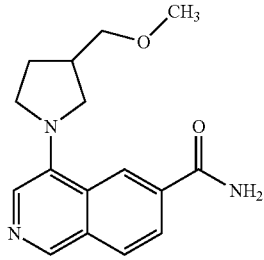 [SMILES: COCC1CCN(c2cncc3ccc(C(N)=O)cc23)C1] | ¹H-NMR (DMSO-D₆) δ: 1.73-1.76 (1H, m), 2.10-2.13 (1H, m), 2.58-2.65 (1H, m), 3.30 (3H, s), 3.35-3.36 (1H, m), 3.43 (2H, d, J = 7.1 Hz), 3.48-3.61 (3H, m), 7.59 (1H, s), 8.01 (1H, s), 8.02 (1H, d, J = 8.5 Hz), 8.06 (1H, d, J = 8.5 Hz), 8.25 (1H, s), 8.67 (1H, s), 8.79 (1H, s). MS (FAB⁺) m/z 286 (M + H)⁺ | C |
|---|---|---|---|
| 74 | 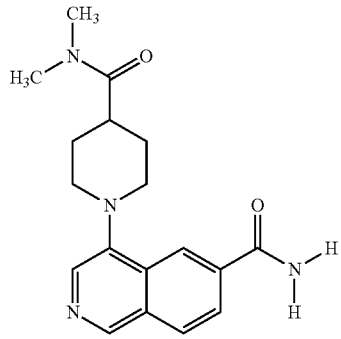 [SMILES: CN(C)C(=O)C1CCN(c2cncc3ccc(C(N)=O)cc23)CC1] | ¹H-NMR (DMSO-D₆) δ: 1.78-1.85 (2H, m), 1.91-2.04 (2H, m), 2.86 (3H, s), 2.82-2.88 (1H, m), 2.88-2.96 (2H, m), 3.08 (3H, s), 3.39-3.47 (2H, m), 7.64 (1H, br s), 8.06 (1H, d, J = 8.5 Hz), 8.15 (1H, d, J = 8.5 Hz), 8.21 (1H, s), 8.34 (1H, br s), 8.52 (1H, s), 9.04 (1H, s). MS (FAB⁺) m/z: 327 (M + H)⁺. | C |
| 75 | 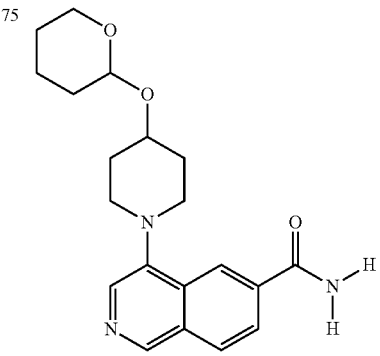 | ¹H-NMR (DMSO-D₆) δ: 1.42-1.57 (4H, m), 1.61-1.72 (1H, m), 1.73-1.86 (2H, m), 1.88-1.96 (1H, m), 2.04-2.14 (2H, m), 2.91-3.02 (2H, m), 3.34-3.41 (2H, m), 3.44-3.51 (1H, m), 3.80-3.89 (2H, m), 4.80-4.82 (1H, m), 7.64 (1H, br s), 8.06 (1H, d, J = 8.7 Hz), 8.15 (1H, d, J = 8.7 Hz), 8.23 (1H, s), 8.32 (1H, br s), 8.51 (1H, s), 9.04 (1H, s). MS (FAB⁺) m/z: 356 (M + H)⁺. | C |
| 76 | 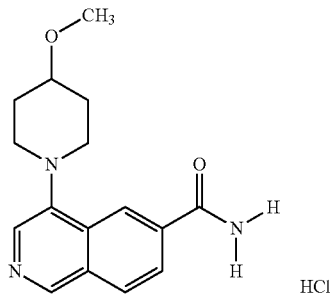 [SMILES: COC1CCN(c2cncc3ccc(C(N)=O)cc23)CC1 ; Cl] | ¹H-NMR (DMSO-D₆) δ: 1.76-1.87 (2H, m), 2.07-2.16 (2H, m), 3.00-3.09 (2H, m), 3.33 (3H, s), 3.45-3.51 (3H, m), 7.81 (1H, br s), 8.24 (1H, d, J = 8.7 Hz), 8.26 (1H, s), 8.42 (1H, d, J = 8.7 Hz), 8.48 (1H, br s), 8.58 (1H, s), 9.36 (1H, s). MS (FAB⁺) m/z: 286 (M + H)⁺. | C |
| 77 | 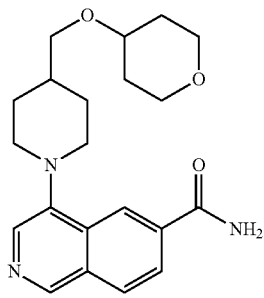 | ¹H-NMR (DMSO-D₆) δ: 1.38-1.47 (2H, m), 1.52-1.62 (2H, m), 1.69-1.80 (1H, br m), 1.88 (4H, d, J = 12.8 Hz), 2.83 (2H, t, J = 11.2 Hz), 3.39-3.44 (6H, m), 3.46-3.53 (1H, m), 3.79-3.84 (2H, m), 7.64 (1H, br s), 8.05 (1H, d, J = 8.3 Hz), 8.15 (1H, d, J = 8.3 Hz), 8.22 (1H, s), 8.30 (1H, br s), 8.49 (1H, s), 9.03 (1H, s). MS (FAB⁺) m/z: 370 (M + H)⁺ | C |

TABLE 9-continued
| 78 | 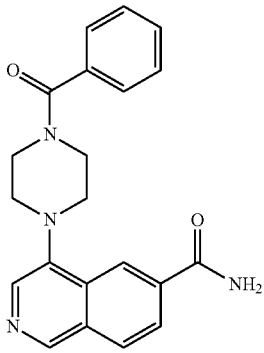 [SMILES: NC(=O)c1ccc2cncc(N3CCN(C(=O)c4ccccc4)CC3)c2c1] | ¹H-NMR (DMSO-D₆) δ: 3.09-3.26 (4H, br m), 3.58-4.06 (4H, br m), 7.49 (5H, s), 7.67 (1H, br s), 8.07 (1H, d, J = 8.7 Hz), 8.18 (1H, d, J = 8.7 Hz), 8.28 (1H, s), 8.33 (1H, br s), 8.54 (1H, s), 9.10 (1H, s). MS (FAB⁺) m/z: 361 (M + H)⁺ | C |
TABLE 10
| 79 | 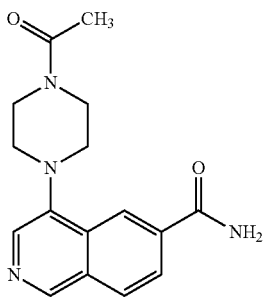 [SMILES: CC(=O)N1CCN(c2cncc3ccc(C(N)=O)cc23)CC1] | 1H-NMR (DMSO-D₆) δ: 2.09 (3H, s), 3.06-3.10 (2H, m), 3.12-3.16 (2H, m), 3.72-3.78 (4H, m), 7.67 (1H, br s), 8.08 (1H, d, J = 8.7 Hz), 8.19 (1H, d, J = 8.7 Hz), 8.25 (1H, s), 8.35 (1H, br s), 8.55 (1H, s), 9.09 (1H, s). MS (FAB⁺) m/z: 299 (M + H)⁺ | C |
| 80 | 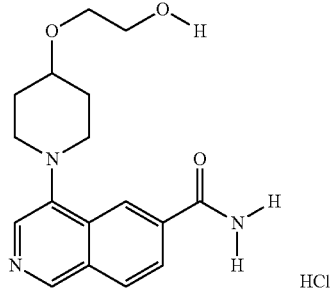 [SMILES: NC(=O)c1ccc2cncc(N3CCC(OCCO)CC3)c2c1 ; Cl] | ¹H-NMR (DMSO-D₆) δ: 1.74-1.88 (2H, m), 2.05-2.15 (2H, m), 3.00-3.09 (2H, m), 3.50-3.65 (7H, m), 7.84 (1H, br s), 8.26 (1H, s), 8.26 (1H, d, J = 8.8 Hz), 8.46 (1H, d, J = 8.8 Hz), 8.50 (1H, br s), 8.58 (1H, s), 9.41 (1H, s). MS (FAB⁺) m/z: 316 (M + H)⁺. | C |
| 81 | 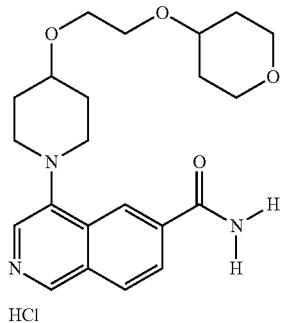 [SMILES: NC(=O)c1ccc2cncc(N3CCC(OCCOC4CCOCC4)CC3)c2c1 ; Cl] | ¹H-NMR (DMSO-D₆) δ: 1.34-1.46 (2H, m), 1.79-1.90 (4H, m), 2.06-2.16 (2H, m), 3.02-3.10 (2H, m), 3.30-3.37 (2H, m), 3.38-3.46 (2H, m), 3.49-3.56 (1H, m), 3.57-3.67 (5H, m), 3.76-3.84 (2H, m), 7.85 (1H, br s), 8.27 (1H, s), 8.27 (1H, d, J = 10.0 Hz), 8.47 (1H, d, J = 10.0 Hz), 8.51 (1H, br s), 8.59 (1H, s), 9.43 (1H, s). MS (FAB⁺) m/z: 400 (M + H)⁺. | C |

TABLE 10-continued
| | | | |
|---|---|---|---|
| 82 | 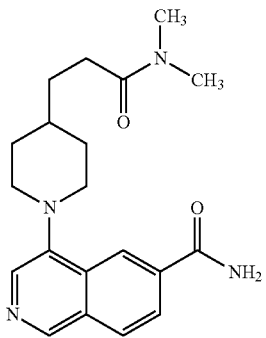 [SMILES: CN(C)C(=O)CCC1CCN(c2cncc3ccc(C(N)=O)cc23)CC1] | ¹H-NMR (DMSO-D₆) δ: 1.46-1.61 (5H, m), 1.84-1.91 (2H, m), 2.35-2.42 (2H, m), 2.77-2.85 (7H, m), 2.99 (3H, s), 3.45-3.52 (2H, m), 7.64 (1H, br s), 8.05 (1H, d, J = 8.0 Hz), 8.15 (1H, d, J = 8.0 Hz), 8.21 (1H, s), 8.31 (1H, br s), 8.50 (1H, s), 9.03 (1H, s). MS (FAB⁺) m/z: 355 (M + H)⁺ | C |
| 83 | 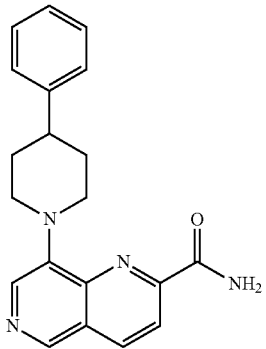 [SMILES: NC(=O)c1ccc2cncc(N3CCC(c4ccccc4)CC3)c2n1] | ¹H-NMR (DMSO-D₆) δ: 1.91-1.99 (2H, m), 2.03-2.13 (2H, m), 2.74-2.84 (1H, m), 2.97-3.07 (2H, m), 4.10-4.13 (2H, m), 7.20-7.25 (1H, m), 7.32-7.39 (4H, m), 7.88 (1H, br s), 7.99 (1H, br s), 8.25 (1H, d, J = 8.5 Hz), 8.36 (1H, s), 8.69 (1H, d, J = 8.5 Hz), 9.02 (1H, s). MS (FAB⁺) m/z: 333 (M + H)⁺ | A |
| 84 | 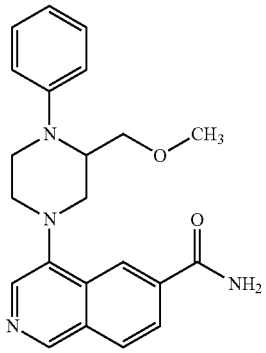 [SMILES: COCC1CN(c2cncc3ccc(C(N)=O)cc23)CCN1c1ccccc1] | ¹H-NMR (DMSO-D₆) δ: 3.05-3.15 (2H, m), 3.29 (3H, s), 3.30-3.36 (2H, m), 3.45-3.49 (1H, m), 3.57-3.62 (2H, m), 4.17-4.24 (2H, m), 6.78 (1H, t, J = 7.2 Hz), 7.02 (2H, d, J = 8.3 Hz), 7.27 (2H, dd, J = 8.3, 7.2 Hz), 7.69 (1H, br s), 8.06 (1H, d, J = 8.5 Hz), 8.20 (1H, br s), 8.20 (1H, d, J = 8.5 Hz), 8.34 (1H, s), 8.59 (1H, s), 9.11 (1H, s). MS (FAB) m/z: 377 (M + H)⁺ | C |
TABLE 11
| | | | |
|---|---|---|---|
| 85 | 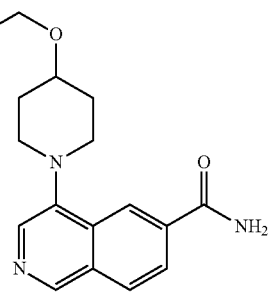 | ¹H-NMR (DMSO-D₆) δ: 1.78-1.89 (2H, m), 2.05-2.16 (2H, m), 2.99-3.09 (2H, m), 3.34-3.44 (2H, m), 3.45-3.53 (4H, m), 3.55-3.66 (5H, m), 7.82 (1H, br s), 8.21-8.28 (2H, m), 8.43 (1H, d, J = 8.5 Hz), 8.48 (1H, br s), 8.58 (1H, s), 9.38 (1H, s). MS (FAB⁺) m/z: 360 (M + H)⁺. | C |

TABLE 11-continued

| 86 | 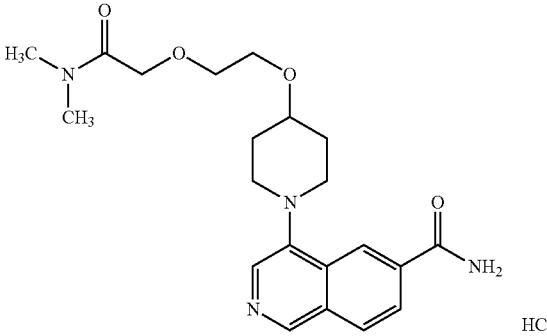 HCl | $^1$H-NMR (DMSO-D$_6$) δ: 1.77-1.89 (2H, m), 2.06-2.16 (2H, m), 2.82 (3H, s), 2.93 (3H, s), 3.00-3.10 (2H, m), 3.35-3.45 (2H, m), 3.58-3.67 (5H, m), 4.17 (2H, s), 7.82 (1H, br s), 8.22-8.28 (2H, m), 8.43 (1H, d, J = 8.8 Hz), 8.49 (1H, br s), 8.58 (1H, s), 9.38 (1H, s). MS (FAB$^+$) m/z: 401 (M + H)$^+$. | C |
| --- | --- | --- | --- |
| 87 | 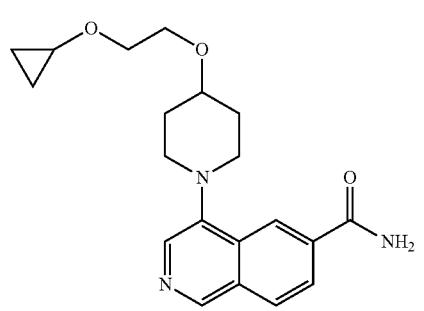 [SMILES: NC(=O)c1ccc2cncc(N3CCC(OCCOC4CC4)CC3)c2c1] | $^1$H-NMR (DMSO-D$_6$) δ: 0.40-0.52 (4H, m), 1.77-1.85 (2H, m), 2.03-2.13 (2H, m), 2.89-2.99 (2H, m), 3.26-3.38 (3H, m), 3.51-3.65 (5H, m), 7.62 (1H, br s), 8.05 (1H, d, J = 8.5 Hz), 8.15 (1H, d, J = 8.5 Hz), 8.22 (1H, br s), 8.31 (1H, s), 8.50 (1H, s), 9.03 (1H, s). MS (FAB$^+$) m/z: 356 (M + H)$^+$ | C |
| 88 | 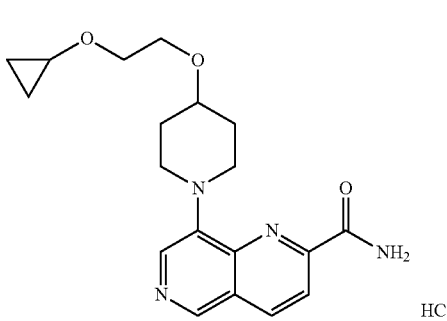 HCl | $^1$H-NMR (DMSO-D$_6$) δ: 0.39-0.51 (4H, m), 1.73-1.87 (2H, m), 2.05-2.17 (2H, m), 3.28-3.35 (1H, m), 3.37-3.49 (2H, m), 3.56-3.68 (5H, m), 3.92-4.04 (2H, m), 7.98 (1H, br s), 8.18 (1H, s), 8.39 (1H, br s), 8.42 (1H, d, J = 8.7 Hz), 8.96 (1H, d, J = 8.7 Hz), 9.37 (1H, s). MS (FAB$^+$) m/z: 357 (M + H)$^+$ | A |
| 89 | 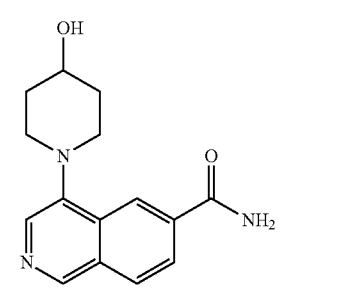 [SMILES: NC(=O)c1ccc2cncc(N3CCC(O)CC3)c2c1] | $^1$H-NMR (DMSO-D$_6$) δ: 1.70-1.82 (2H, m), 1.93-2.02 (2H, m), 2.87-2.97 (2H, m), 3.27-3.38 (2H, m), 3.66-3.79 (1H, m), 4.77 (1H, d, J = 4.2 Hz), 7.61 (1H, br s), 8.04 (1H, d, J = 8.5 Hz), 8.14 (1H, d, J = 8.5 Hz), 8.22 (1H, s), 8.30 (1H, br s), 8.50 (1H, s), 9.02 (1H, s). MS (FAB$^+$) m/z: 272 (M + H)$^+$ | C |
| 90 | 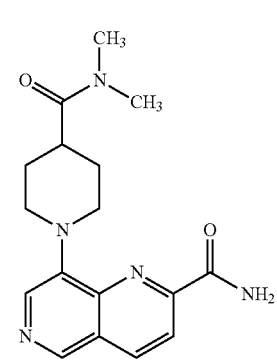 [SMILES: CN(C)C(=O)C1CCN(c2cncc3ccc(C(N)=O)nc23)CC1] | $^1$H-NMR (DMSO-D$_6$) δ: 1.77-1.86 (2H, m), 1.86-1.98 (2H, m), 2.85 (3H, s), 2.88-2.91 (1H, m), 2.95-3.04 (2H, m), 3.08 (3H, s), 3.32 (2H, s), 4.01-4.04 (2H, m), 7.79 (1H, br s), 8.02 (1H, br s), 8.23 (1H, d, J = 8.3 Hz), 8.31 (1H, s), 8.68 (1H, d, J = 8.5 Hz), 9.00 (1H, s). MS (FAB$^+$) m/z 328 (M + H)$^+$ | A |

TABLE 12
| | | | |
|---|---|---|---|
| 91 | 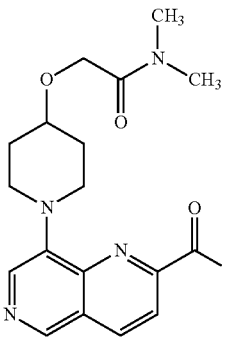 | ¹H-NMR (DMSO-D₆) δ: 1.78-1.87 (2H, m), 2.10-2.12 (2H, m), 2.83 (3H, s), 2.97 (3H, s), 3.28-3.37 (2H, m), 3.66-3.68 (1H, m), 3.88-3.90 (2H, m), 4.22 (2H, s), 7.91 (1H, br s), 8.13 (1H, br s), 8.36-8.37 (2H, m), 8.85 (1H, d, J = 8.6 Hz), 9.23 (1H, s). MS (FAB⁺) m/z 358 (M + H)⁺ | A |
| 92 | 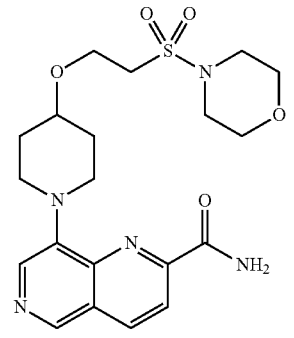 [SMILES: NC(=O)c1ccc2cncc(N3CCC(OCCS(=O)(=O)N4CCOCC4)CC3)c2n1] | ¹H-NMR (DMSO-D₆) δ: 1.77-1.83 (2H, m), 2.11-2.13 (2H, m), 3.14-3.16 (2H, m), 3.18-3.19 (4H, m), 3.39 (2H, t, J = 6.0 Hz), 3.61-3.69 (5H, m), 3.79-3.80 (2H, m), 3.83 (2H, t, J = 6.0 Hz), 7.83 (1H, br s), 8.01 (1H, br s), 8.23 (1H, d, J = 8.6 Hz), 8.32 (1H, s), 8.68 (1H, d, J = 8.6 Hz), 9.00 (1H, s). MS (FAB⁺) m/z 450 (M + H)⁺ | A |
| 93 | 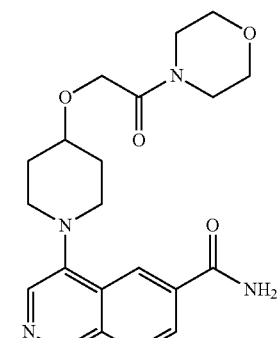 | ¹H-NMR (DMSO-D₆) δ: 1.87-1.89 (2H, m), 2.11-2.13 (2H, m), 3.04-3.06 (2H, m), 3.41-3.45 (6H, m), 3.58-3.60 (4H, m), 3.67-3.67 (1H, m), 4.26 (2H, s), 7.82 (1H, s), 8.23-8.29 (2H, m), 8.44 (1H, d, J = 8.8 Hz), 8.49 (1H, s), 8.58 (1H, s), 9.39 (1H, s). MS (FAB⁺) m/z 399 (M + H)⁺ | C |
| 94 | 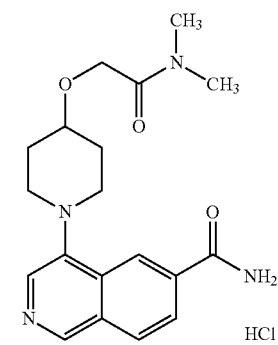 [SMILES: CN(C)C(=O)COC1CCN(c2cncc3ccc(C(N)=O)cc23)CC1 ; Cl] | ¹H-NMR (DMSO-D₆) δ: 1.77-1.95 (2H, m), 2.07-2.20 (2H, m), 2.84 (3H, s), 2.98 (3H, s), 2.99-3.09 (2H, m), 3.35-3.45 (2H, m), 3.61-3.71 (1H, m), 4.23 (2H, s), 7.81 (1H, br s), 8.24 (1H, d, J = 8.7 Hz), 8.26 (1H, s), 8.42 (1H, d, J = 8.7 Hz), 8.48 (1H, br s), 8.58 (1H, s), 9.37 (1H, s). MS (FAB⁺) m/z 357 (M + H)⁺ | C |

TABLE 12-continued
| 95 | 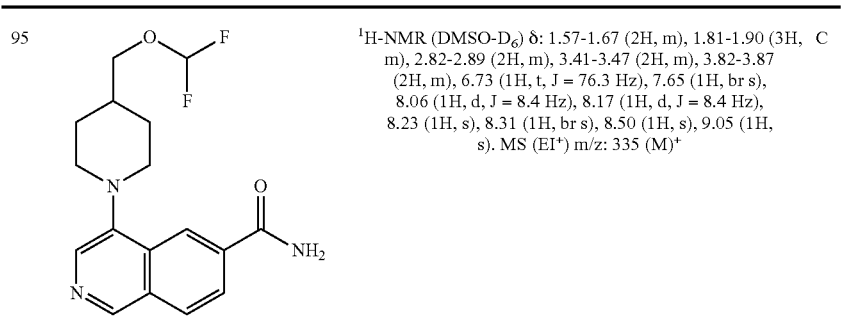 | ¹H-NMR (DMSO-D₆) δ: 1.57-1.67 (2H, m), 1.81-1.90 (3H, m), 2.82-2.89 (2H, m), 3.41-3.47 (2H, m), 3.82-3.87 (2H, m), 6.73 (1H, t, J = 76.3 Hz), 7.65 (1H, br s), 8.06 (1H, d, J = 8.4 Hz), 8.17 (1H, d, J = 8.4 Hz), 8.23 (1H, s), 8.31 (1H, br s), 8.50 (1H, s), 9.05 (1H, s). MS (EI⁺) m/z: 335 (M)⁺ | C |
| --- | --- | --- | --- |
| 96 | 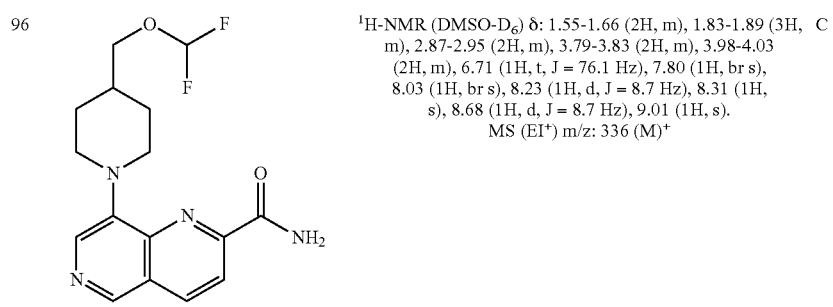 | ¹H-NMR (DMSO-D₆) δ: 1.55-1.66 (2H, m), 1.83-1.89 (3H, m), 2.87-2.95 (2H, m), 3.79-3.83 (2H, m), 3.98-4.03 (2H, m), 6.71 (1H, t, J = 76.1 Hz), 7.80 (1H, br s), 8.03 (1H, br s), 8.23 (1H, d, J = 8.7 Hz), 8.31 (1H, s), 8.68 (1H, d, J = 8.7 Hz), 9.01 (1H, s). MS (EI⁺) m/z: 336 (M)⁺ | C |
TABLE 13
| 97 | 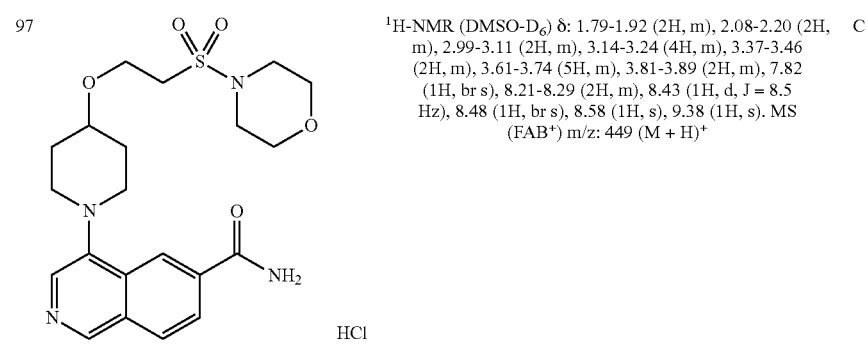 | ¹H-NMR (DMSO-D₆) δ: 1.79-1.92 (2H, m), 2.08-2.20 (2H, m), 2.99-3.11 (2H, m), 3.14-3.24 (4H, m), 3.37-3.46 (2H, m), 3.61-3.74 (5H, m), 3.81-3.89 (2H, m), 7.82 (1H, br s), 8.21-8.29 (2H, m), 8.43 (1H, d, J = 8.5 Hz), 8.48 (1H, br s), 8.58 (1H, s), 9.38 (1H, s). MS (FAB⁺) m/z: 449 (M + H)⁺ | C |
| --- | --- | --- | --- |
| 98 | 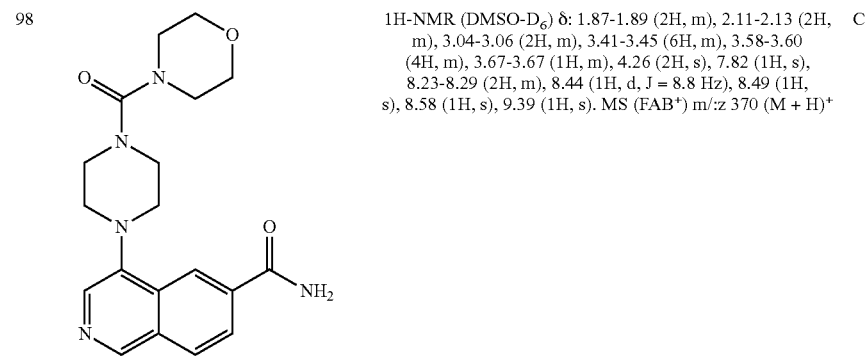 | 1H-NMR (DMSO-D₆) δ: 1.87-1.89 (2H, m), 2.11-2.13 (2H, m), 3.04-3.06 (2H, m), 3.41-3.45 (6H, m), 3.58-3.60 (4H, m), 3.67-3.67 (1H, m), 4.26 (2H, s), 7.82 (1H, s), 8.23-8.29 (2H, m), 8.44 (1H, d, J = 8.8 Hz), 8.49 (1H, s), 8.58 (1H, s), 9.39 (1H, s). MS (FAB⁺) m/:z 370 (M + H)⁺ | C |

TABLE 13-continued
| | | | |
|---|---|---|---|
| 99 | 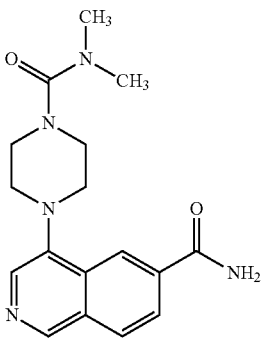 [SMILES: CN(C)C(=O)N1CCN(c2cncc3ccc(C(N)=O)cc23)CC1] | ¹H-NMR (DMSO-D₆) δ: 2.81 (6H, s), 3.09-3.16 (4H, m), 3.38-3.47 (4H, m), 7.64 (1H, br s), 8.07 (1H, d, J = 8.4 Hz), 8.17 (1H, d, J = 8.3 Hz), 8.25 (1H, s), 8.32 (1H, br s), 8.53 (1H, s), 9.08 (1H, s). MS (FAB⁺) m/z: 328 (M + H)⁺ | C |
| 100 | 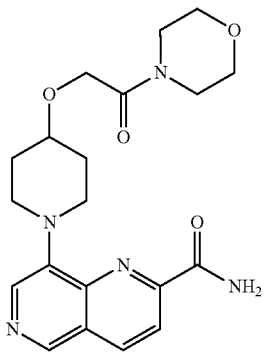 [SMILES: NC(=O)c1ccc2cncc(N3CCC(OCC(=O)N4CCOCC4)CC3)c2n1] | ¹H-NMR (DMSO-D₆) δ: 1.74-1.87 (2H, m), 2.06-2.17 (2H, m), 3.10-3.21 (2H, m), 3.42-3.50 (4H, m), 3.53-3.68 (6H, m), 3.73-3.82 (2H, m), 4.23 (2H, s), 7.81 (1H, br s), 8.00 (1H, br s), 8.23 (1H, d, J = 8.5 Hz), 8.32 (1H, s), 8.67 (1H, d, J = 8.5 Hz), 9.00 (1H, s). MS (FAB⁺) m/z: 400 (M + H)⁺ | A |
| 101 | 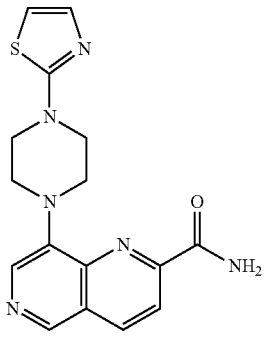 [SMILES: NC(=O)c1ccc2cncc(N3CCN(c4nccs4)CC3)c2n1] | ¹H-NMR (DMSO-D₆) δ: 3.58-3.61 (4H, m), 3.70-3.74 (4H, m), 6.90 (1H, d, J = 3.4 Hz), 7.22 (1H, d, J = 3.4 Hz), 7.92 (1H, br s), 7.98 (1H, br s), 8.27 (1H, d, J = 8.6 Hz), 8.37 (1H, s), 8.72 (1H, d, J = 8.6 Hz), 9.08 (1H, s). | A |
| 102 | 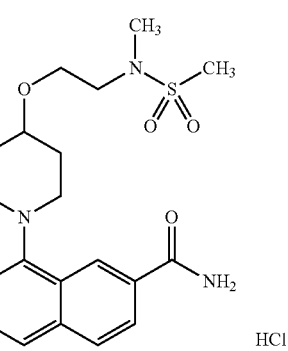 HCl | ¹H-NMR (DMSO-D₆) δ: 1.79-1.90 (2H, m), 2.08-2.18 (2H, m), 2.86 (3H, s), 2.92 (3H, s), 3.01-3.10 (2H, m), 3.30 (2H, t, J = 5.6 Hz), 3.36-3.45 (2H, m), 3.60-3.65 (1H, m), 3.66 (2H, t, J = 5.6 Hz), 7.80 (1H, br s), 8.24 (1H, d, J = 8.6 Hz), 8.26 (1H, s), 8.42 (1H, d, J = 8.6 Hz), 8.47 (1H, br s), 8.58 (1H, s), 9.36 (1H, s). MS (FAB⁺) m/z: 407 (M + H)⁺ | C |

TABLE 14

| # | Structure | NMR / MS | Grade |
|---|---|---|---|
| 103 | (piperidine-CH2-OCHF2 attached to isoquinoline-6-carboxamide) | ¹H-NMR (DMSO-D₆) δ: 1.25-1.33 (1H, m), 1.83-1.91 (3H, m), 2.20-2.27 (1H, m), 2.69-2.75 (1H, m), 2.81-2.87 (1H, m), 3.28-3.40 (2H, m), 3.83-3.90 (2H, m), 6.68 (1H, t, J = 76.2 Hz), 7.63 (1H, br s), 8.06 (1H, d, J = 8.0 Hz), 8.16 (1H, (d, J = 8.0 Hz), 8.23 (1H, s), 8.28 (1H, br s), 8.50 (1H, s), 9.06 (1H, s). MS (FAB⁺) m/z: 336 (M + H)⁺ | C |
| 104 | (piperidine-CH2-OCHF2 attached to 1,6-naphthyridine-2-carboxamide) | ¹H-NMR (DMSO-D₆) δ: 1.23-1.32 (1H, m), 1.78-1.90 (3H, m), 2.21-2.29 (1H, m), 2.70-2.75 (1H, m), 2.96-3.02 (1H, m), 3.73-3.79 (2H, m), 3.86-3.90 (1H, m), 4.15-4.19 (1H, m), 6.67 (1H, t, J = 75.6 Hz), 7.77 (1H, br s), 8.05 (1H, br s), 8.25 (1H, d, J = 8.3 Hz), 8.30 (1H, s), 8.69 (1H, d, J = 8.3 Hz), 9.01 (1H, s). MS (FAB⁺) m/z: 337 (M + H)⁺ | A |
| 105 | (morpholine-CH2-OCH3 attached to isoquinoline-6-carboxamide) | ¹H-NMR (DMSO-D₆) δ: 2.76-2.81 (1H, m), 2.94-3.00 (1H, m), 3.25-3.30 (2H, m), 3.29 (3H, s), 3.41-3.48 (2H, m), 3.88-3.94 (1H, m), 3.97-4.03 (2H, m), 7.66 (1H, br s), 8.08 (1H, d, J = 8.6 Hz), 8.19 (1H, d, J = 8.6 Hz), 8.26 (1H, s), 8.34 (1H, br s), 8.54 (1H, s), 9.11 (1H, s). MS (FAB⁺) m/z: 302 (M + H)⁺ | C |
| 106 | (piperidine-O-CH2CH2-SO2-N(CH3)2 attached to isoquinoline-6-carboxamide) HCl | ¹H-NMR (DMSO-D₆) δ: 1.78-1.92 (2H, m), 2.06-2.21 (2H, m), 2.80 (6H, s), 2.98-3.12 (2H, m), 3.35 (2H, t, J = 6.0 Hz), 3.37-3.46 (2H, m), 3.63-3.73 (2H, m), 3.84 (2H, t, J = 6.0 Hz), 7.79 (1H, br s), 8.23 (1H, d, J = 8.6 Hz), 8.26 (1H, s), 8.41 (1H, d, J = 8.6 Hz), 8.46 (1H, br s), 8.57 (1H, s), 9.35 (1H, s). MS (FAB⁺) m/z: 407 (M + H)⁺ | C |
| 107 | (piperidine-O-CH2CH2-SO2-N(CH3)2 attached to 1,6-naphthyridine-2-carboxamide) | ¹H-NMR (DMSO-D₆) δ: 1.73-1.85 (2H, m), 2.05-2.16 (2H, m), 2.79 (6H, s), 3.11-3.21 (2H, m), 3.34 (2H, t, J = 6.1 Hz), 3.62-3.67 (1H, m), 3.75-3.81 (2H, m), 3.82 (2H, t, J = 6.1 Hz), 7.81 (1H, br s), 7.99 (1H, br s), 8.23 (1H, d, J = 8.4 Hz), 8.32 (1H, s), 8.67 (1H, d, J = 8.4 Hz), 9.00 (1H, s). MS (FAB⁺) m/z: 408 (M + H)⁺ | A |

TABLE 15

| | | | |
|---|---|---|---|
| 108 | *[structure: 4-methoxy-3-(methoxymethyl)piperidin-1-yl substituted 1,6-naphthyridine-2-carboxamide]* | ¹H-NMR (DMSO-D₆) δ: 1.56-1.68 (0.5H, m), 1.80-1.90 (0.5H, m), 1.94-2.03 (0.5H, m), 2.12-2.27 (1.0H, m), 2.31-2.41 (0.5H, m), 2.79-2.87 (0.5H, m), 3.01-3.10 (0.5H, m), 3.17-3.22 (0.5H, m), 3.26-3.33 (8.5H, m), 3.34-3.39 (1.0H, m), 3.42-3.44 (1.0H, m), 3.56-3.64 (1.5H, m), 3.68-3.76 (0.5H, m), 3.82-3.90 (0.5H, m), 4.36-4.45 (0.5H, m), 7.95 (0.5H, br s), 8.03 (1.0H, br s), 8.08 (0.5H, br s), 8.22-8.30 (2.0H, m), 8.66 (1.0H, d, J = 8.5 Hz), 8.98 (1.0H, s). MS (FAB⁺) m/z: 331 (M + H)⁺. | A |
| 109 | *[structure: 4-methoxy-3-(methoxymethyl)piperidin-1-yl substituted isoquinoline-6-carboxamide, HCl]* | ¹H-NMR (DMSO-D₆) δ: 1.71-1.83 (0.5H, m), 1.89-1.99 (0.5H, m), 2.01-2.10 (0.5H, m), 2.13-2.30 (1.0H, m), 2.36-2.47 (1.0H, m), 2.89-2.99 (1.0H, m), 3.10-3.17 (1.0H, m), 3.17-3.23 (1.0H, m), 3.27 (4.0H, m), 3.33 (3.0H, m), 3.45-3.61 (6.0H, m), 7.81 (1.0H, br s), 8.21-8.29 (2.0H, m), 8.37-8.48 (2.0H, m), 8.59 (1.0H, d, J = 6.3 Hz), 9.38 (1.0H, s). MS (FAB⁺) m/z: 330 (M + H)⁺ | C |
| 110 | *[structure: 4-((2-(tetrahydro-2H-pyran-4-yloxy)ethoxy)methyl)piperidin-1-yl substituted 1,6-naphthyridine-2-carboxamide]* | ¹H-NMR (DMSO-D₆) δ: 1.34-1.44 (2H, m), 1.49-1.60 (2H, m), 1.75-1.88 (5H, m), 2.86-2.93 (2H, m), 3.29-3.39 (4H, m), 3.47-3.59 (5H, m), 3.77-3.83 (2H, m), 3.96-4.01 (2H, m), 7.77 (1H, br s), 8.02 (1H, br s), 8.23 (1H, d, J = 8.5 Hz), 8.30 (1H, s), 8.67 (1H, d, J = 8.5 Hz), 8.99 (1H, s). MS (FAB⁺) m/z: 415 (M + H)⁺ | A |
| 111 | *[structure: 4-(2-isopropoxyethoxy)piperidin-1-yl substituted 1,6-naphthyridine-2-carboxamide, HCl]* | ¹H-NMR (DMSO-D₆) δ: 1.09 (6H, d, J = 6.1 Hz), 1.74-1.87 (2H, m), 2.05-2.16 (2H, m), 3.37-3.46 (2H, m), 3.51 (2H, t, J = 4.9 Hz), 3.56-3.62 (3H, m), 3.62-3.69 (1H, m), 3.93-4.01 (2H, m), 7.98 (1H, br s), 8.17 (1H, s), 8.39 (1H, br s), 8.42 (1H, d, J = 8.5 Hz), 8.95 (1H, d, J = 8.5 Hz), 9.36 (1H, s). MS (FAB⁺) m/z: 359 (M + H)⁺ | A |
| 112 | *[structure: 4-(methoxymethyl)piperidin-1-yl substituted 1,6-naphthyridine-2-carboxamide]* | ¹H-NMR (DMSO-D₆) δ: 1.48-1.64 (2H, m), 1.74-1.90 (3H, m), 2.85-2.96 (2H, m), 3.24-3.37 (5H, m), 3.92-4.05 (2H, m), 7.77 (1H, br s), 8.01 (1H, br s), 8.23 (1H, d, J = 8.5 Hz), 8.30 (1H, s), 8.67 (1H, d, J = 8.5 Hz), 8.99 (1H, s). MS (FAB⁺) m/z: 301 (M + H)⁺ | A |

TABLE 16
| | | | |
|---|---|---|---|
| 113 | 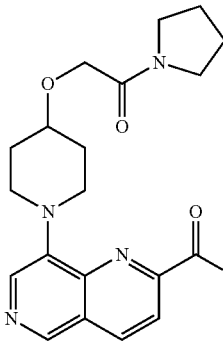 | ¹H-NMR (DMSO-D₆) δ: 1.73-1.90 (6H, m), 2.10-2.13 (2H, m), 3.14-3.17 (2H, m), 3.30-3.32 (2H, m), 3.42-3.44 (2H, m), 3.63-3.65 (1H, m), 3.77-3.79 (2H, m), 7.81 (1H, br s), 7.99 (1H, br s), 8.23 (1H, d, J = 8.4 Hz), 8.32 (1H, s), 8.67 (1H, d, J = 8.4 Hz), 9.00 (1H, s). MS (FAB⁺) m/z: 384 (M + H)⁺ | A |
| 114 | 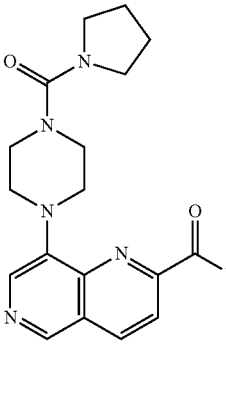 | ¹H-NMR (DMSO-D₆) δ: 1.74-1.81 (4H, m), 3.30-3.35 (4H, m), 3.44-3.50 (8H, m), 7.84 (1H, br s), 7.99 (1H, br s), 8.25 (1H, d, J = 8.6 Hz), 8.32 (1H, s), 8.69 (1H, d, J = 8.6 Hz), 9.04 (1H, s). MS (FAB⁺) m/z: 355 (M + H)⁺ | A |
| 115 | 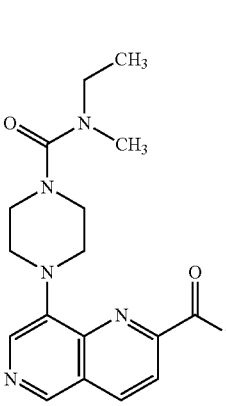 | ¹H-NMR (DMSO-D₆) δ: 1.09 (3H, t, J = 7.1 Hz), 2.80 (3H, s), 3.18 (2H, q, J = 7.1 Hz), 3.39-3.48 (8H, m), 7.84 (1H, br s), 7.98 (1H, br s), 8.25 (1H, d, J = 8.6 Hz), 8.32 (1H, s), 8.69 (1H, d, J = 8.6 Hz), 9.04 (1H, s). MS (FAB⁺) m/z: 343 (M + H)⁺ | A |
| 116 | 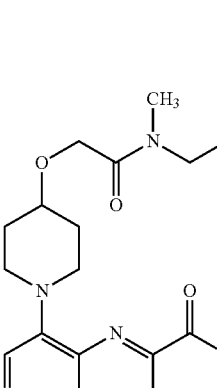 | ¹H-NMR (DMSO-D₆) δ: 1.02 (1.5H, t, J = 7.1 Hz), 1.13 (1.5H, t, J = 7.1 Hz), 1.75-1.87 (2.0H, m), 2.04-2.17 (2.0H, m), 2.80 (1.5H, s), 2.95 (1.5H, s), 3.11-3.21 (2.0H, m), 3.25-3.40 (2.0H, m), 3.57-3.70 (1.0H, m), 3.72-3.83 (2.0H, m), 4.19 (1.0H, s), 4.21 (1.0H, s), 7.81 (1.0H, br s), 7.99 (1.0H, br s), 8.23 (1.0H, d, J = 8.4 Hz), 8.32 (1.0H, s), 8.67 (1.0H, d, J = 8.4 Hz), 9.00 (1.0H, s). MS (FAB⁺) m/z: 372 (M + H)⁺ | A |

TABLE 16-continued
| 117 | 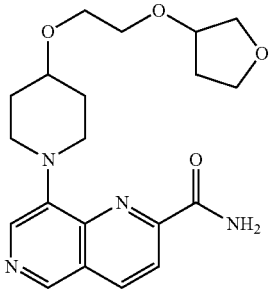 [SMILES: NC(=O)c1ccc2cncc(N3CCC(OCCOC4CCOC4)CC3)c2n1] | ¹H-NMR (DMSO-D₆) δ: 1.73-1.81 (2H, m), 1.85-1.99 (2H, m), 2.05-2.11 (2H, m), 3.11-3.17 (2H, m), 3.50-3.62 (5H, m), 3.64-3.69 (3H, m), 3.70-3.80 (3H, m), 4.14-4.17 (1H, m), 7.82 (1H, br s), 8.00 (1H, br s), 8.23 (1H, d, J = 8.6 Hz), 8.31 (1H, s), 8.67 (1H, d, J = 8.6 Hz), 9.00 (1H, s). MS (FAB⁺) m/z: 387 (M + H)⁺ | A |
| 118 | 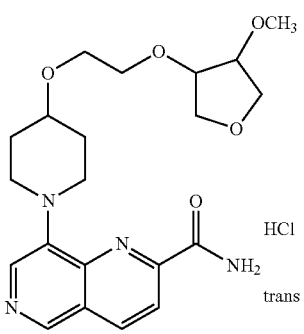 HCl trans | ¹H-NMR (DMSO-D₆) δ: 1.76-1.85 (2H, m), 2.07-2.15 (2H, m), 3.29 (3H, s), 3.39-3.46 (2H, m), 3.58-3.69 (7H, m), 3.75-3.80 (2H, m), 3.84-3.87 (1H, m), 3.93-4.03 (3H, m), 7.99 (1H, br s), 8.18 (1H, s), 8.39 (1H, br s), 8.42 (1H, d, J = 8.6 Hz), 8.96 (1H, d, J = 8.6 Hz), 9.37 (1H, s). MS (FAB⁺) m/z: 417 (M + H)⁺ | A |
TABLE 17
| 119 | 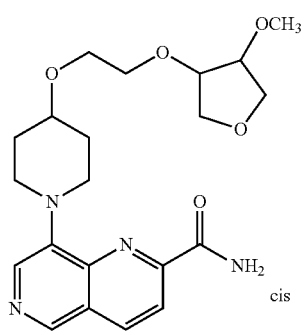 cis | ¹H-NMR (DMSO-D₆) δ: 1.70-1.83 (2H, m), 2.04-2.14 (2H, m), 3.10-3.20 (2H, m), 3.33 (3H, s), 3.56-3.69 (7H, m), 3.74-3.84 (4H, m), 3.87-3.93 (1H, m), 4.06-4.11 (1H, m), 7.81 (1H, br s), 8.00 (1H, br s), 8.23 (1H, d, J = 8.5 Hz), 8.31 (1H, s), 8.67 (1H, d, J = 8.5 Hz), 9.00 (1H, s). MS (FAB⁺) m/z: 417 (M + H)⁺ | A |
| 120 | 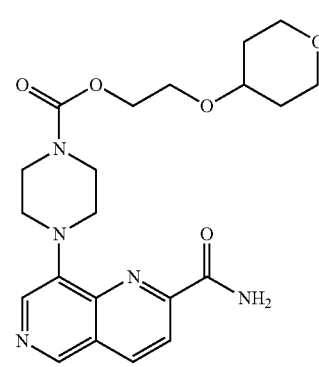 [SMILES: NC(=O)c1ccc2cncc(N3CCN(C(=O)OCCOC4CCOCC4)CC3)c2n1] | ¹H-NMR (DMSO-D₆) δ: 1.36-1.44 (2H, m), 1.82-1.87 (2H, m), 3.29-3.36 (2H, m), 3.41-3.47 (4H, m), 3.49-3.55 (1H, m), 3.63-3.73 (6H, m), 3.77-3.82 (2H, m), 4.14-4.18 (2H, m), 7.86 (1H, br s), 7.98 (1H, br s), 8.25 (1H, d, J = 8.0 Hz), 8.33 (1H, s), 8.70 (1H, d, J = 8.0 Hz), 9.06 (1H, s). MS (FAB⁺) m/z: 430 (M + H)⁺ | A |

TABLE 17-continued
| 121 | 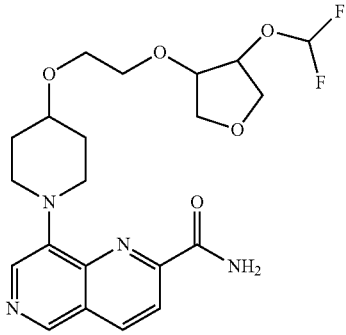 [SMILES: NC(=O)c1ccc2cncc(N3CCC(OCCOC4COCC4OC(F)F)CC3)c2n1] | ¹H-NMR (DMSO-D₆) δ: 1.73-1.82 (2H, m), 2.05-2.12 (2H, m), 3.11-3.19 (2H, m), 3.54-3.81 (9H, m), 3.86-3.91 (2H, m), 4.12-4.15 (1H, m), 4.71-4.74 (1H, m), 6.81 (1H, t, J = 75.2 Hz), 7.82 (1H, br s), 8.00 (1H, br s), 8.23 (1H, d, J = 8.7 Hz), 8.31 (1H, s), 8.67 (1H, d, J = 8.7 Hz), 9.00 (1H, s). MS (FAB⁺) m/z: 453 (M + H)⁺ | A |
|---|---|---|---|
| 122 | 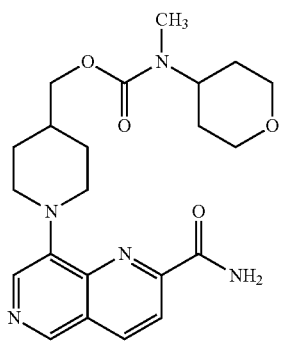 [SMILES: CN(C(=O)OCC1CCN(c2cncc3ccc(C(N)=O)nc23)CC1)C1CCOCC1] | ¹H-NMR (DMSO-D₆) δ: 1.46-1.76 (6H, m), 1.81-1.93 (3H, m), 2.76 (3H, s), 2.88-2.95 (2H, m), 3.30-3.37 (2H, m), 3.87-3.93 (2H, m), 3.95-4.13 (5H, m), 7.79 (1H, br s), 8.02 (1H, br s), 8.23 (1H, d, J = 8.6 Hz), 8.31 (1H, s), 8.68 (1H, d, J = 8.6 Hz), 9.00 (1H, s). MS (ESI⁺) m/z: 428 (M + H)⁺ | A |
| 123 | 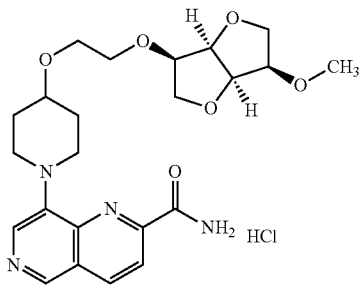 [SMILES: CO[C@@H]1CO[C@H]2[C@@H]1OC[C@H]2OCCOC1CCN(c2cncc3ccc(C(N)=O)nc23)CC1 ; Cl] | ¹H-NMR (DMSO-D₆) δ: 1.72-1.86 (2H, m), 2.04-2.15 (2H, m), 3.30 (3H, s), 3.32-3.48 (4H, m), 3.55-3.75 (5H, m), 3.85-3.97 (5H, m), 4.01-4.10 (1H, m), 4.51-4.56 (2H, m), 7.92 (1H, br s), 8.12 (1H, s), 8.36 (1H, br s), 8.37 (1H, d, J = 8.7 Hz), 8.87 (1H, d, J = 8.7 Hz), 9.25 (1H, s). MS (FAB⁺) m/z: 459 (M + H)⁺ | A |
| 124 | 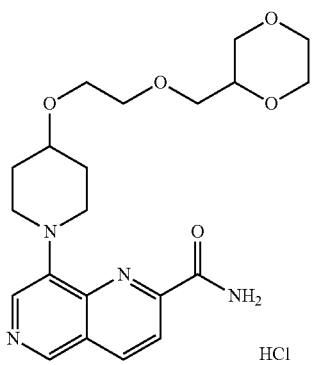 [SMILES: NC(=O)c1ccc2cncc(N3CCC(OCCOCC4COCCO4)CC3)c2n1 ; Cl] | ¹H-NMR (DMSO-D₆) δ: 1.73-1.86 (2H, m), 2.06-2.16 (2H, m), 3.23-3.31 (1H, m), 3.35-3.48 (5H, m), 3.52-3.75 (10H, m), 3.92-4.02 (2H, m), 7.99 (1H, br s), 8.18 (1H, s), 8.39 (1H, br s), 8.43 (1H, d, J = 8.7 Hz), 8.96 (1H, d, J = 8.7 Hz), 9.38 (1H, s). MS (FAB⁺) m/z: 417 (M + H)⁺ | A |

The invention claimed is:

1. A compound having the general formula (I-a) or a pharmacologically acceptable salt thereof:

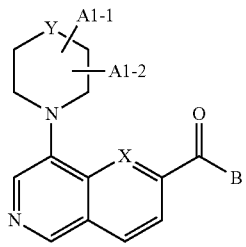

(I-a)

wherein each substituent is defined as follows:
A1-1 is a C1-C3 alkoxy group substituted with a group selected from A2, and A1-2 is a hydrogen atom
A2 is
a 3- to 10-membered heterocyclyloxy group optionally substituted with group(s) selected from A3,
A3:
a halogen atom, an amino group, a hydroxyl group, a cyano group, a C1-C6 alkyl group, a C1-C6 alkoxy group, a halogeno C1-C6 alkoxy group, a C1-C6 alkoxycarbonylamino group, a 3- to 10-membered heterocyclyl group, a 3- to 10-membered heterocyclyloxy group, a carbamoyl group, a di C1-C6 alkylcarbamoyl group, and a C1-C6 alkylsulfonyl group,
B represents any one substituent selected from the following group of substituents:
an amino group optionally substituted with group(s) selected from B1 and
a 3- to 10-membered heterocyclyl group optionally substituted with group(s) selected from B1,
B1:
a hydroxyl group, an amino group, a C1-C6 alkyl group, a C1-C6 alkoxy group, a hydroxy C1-C6 alkyl group,
X represents N, and
Y represents CH or $CH_2$.

2. The compound or the pharmacologically acceptable salt thereof according to claim 1, wherein A3 is the following group of substituents:
a halogen atom, an amino group, a hydroxyl group, a t-butoxycarbonylamino group, a C1-C6 alkyl group, a C1-C3 alkoxy group, a halogeno C1-C3 alkoxy group, a 3- to 10-membered heterocyclyl group, a 3- to 10-membered heterocyclyloxy group, a dimethylcarbamoyl group, a diethylcarbamoyl group, an ethylmethylcarbamoyl group, and a methylsulfonyl group.

3. The compound or the pharmacologically acceptable salt thereof according to claim 1, wherein A3 is the following group of substituents:
a halogen atom, an amino group, a hydroxyl group, a methyl group, a methoxy group, a difluoromethoxy group, a t-butoxycarbonylamino group, a 3- to 10-membered heterocyclyl group, a 3- to 10-membered heterocyclyloxy group, a dimethylcarbamoyl group, and a methylsulfonyl group.

4. The compound or the pharmacologically acceptable salt thereof according to claim 1, wherein A3 is the following group of substituents:
a 3- to 10-membered heterocyclyl group, a 3- to 10-membered heterocyclyloxy group, a methylsulfonyl group, a methoxy group, and a difluoromethoxy group.

5. The compound or the pharmacologically acceptable salt thereof according to claim 1, wherein Y is CH.

6. The compound or the pharmacologically acceptable salt thereof according to claim 1, wherein A1-1 is a group selected from the following group of substituents:
a 2-(tetrahydro-2H-pyran-4-yloxy)ethoxy group, a 2-[(3R)-tetrahydrofuran-3-yloxy]ethoxy group, a 2-[(3S)-tetrahydrofuran-3-yloxy]ethoxy group, a 2-(tetrahydrofuran-3-ylmethoxy)ethoxy group, a 2-[(4-methoxytetrahydrofuran-3-yl)oxy]ethoxy group, and a 2-(tetrahydro-2H-pryan-4-yloxy)ethoxycarbonyl group.

7. The compound or the pharmacologically acceptable salt thereof according to claim 1, wherein B is an amino group optionally substituted with C1-C6 alkyl group(s).

8. The compound or the pharmacologically acceptable salt thereof according to claim 1, wherein B is an amino group, a methylamino group, or an ethylamino group.

9. A compound selected from the following group of compounds or a pharmacologically acceptable salt thereof:
8-{4-[2-(tetrahydro-2H-pyran-4-yloxy)ethoxy]piperidin-1-yl}-1,6-naphthyridine-2-carboxamide,
N-ethyl-8-{4-[2-(tetrahydro-2H-pyran-4-yloxy)ethoxy]piperidin-1-yl}-1,6-naphthyridine-2-carboxamide,
8-(4-{2-[(3R)-tetrahydrofuran-3-yloxy]ethoxy}piperidin-1-yl)-1,6-naphthyridine-2-carboxamide,
N-ethyl-8-(4-{2-[(3R)-tetrahydrofuran-3-yloxy]ethoxy}piperidin-1-yl)-1,6-naphthyridine-2-carboxamide,
8-(4-{2-[(3S)-tetrahydrofuran-3-yloxy]ethoxy}piperidin-1-yl)-1,6-naphthyridine-2-carboxamide,
N-ethyl-8-(4-{2-[(3S)-tetrahydrofuran-3-yloxy]ethoxy}piperidin-1-yl)-1,6-naphthyridine-2-carboxamide,
8-{4-[2-(tetrahydrofuran-3-ylmethoxy)ethoxy]piperidin-1-yl}-1,6-naphthyridine-2-carboxamide,
N-ethyl-8-{4-[2-(tetrahydrofuran-3-ylmethoxy)ethoxy]piperidin-1-yl}-1,6-naphthyridine-2-carboxamide, and
trans-8-(4-{2-[(4-methoxytetrahydrofuran-3-yl)oxy]ethoxy}piperidin-1-yl)-1,6-naphthyridine-2-carboxamide.

10. A pharmaceutical composition comprising the compound or the pharmacologically acceptable salt thereof according to claim 1 as an active ingredient.

11. A method for improving bone metabolism, comprising administering an effective amount of the pharmaceutical composition according to claim 10 to a mammal.

12. A method for treating osteoporosis, comprising administering an effective amount of the pharmaceutical composition according to claim 10 to a mammal.

* * * * *